(12) United States Patent
Whitlock et al.

(10) Patent No.: US 10,017,731 B2
(45) Date of Patent: *Jul. 10, 2018

(54) AMMONIA OXIDIZING BACTERIA FOR TREATMENT OF ECZEMA

(71) Applicant: AOBIOME LLC, Cambridge, MA (US)

(72) Inventors: David R. Whitlock, Cambridge, MA (US); Spiros Jamas, Cambridge, MA (US); Larry Weiss, San Francisco, CA (US)

(73) Assignee: AOBIOME LLC, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/649,323

(22) Filed: Jul. 13, 2017

(65) Prior Publication Data

US 2018/0016544 A1   Jan. 18, 2018

Related U.S. Application Data

(63) Continuation of application No. 14/882,284, filed on Oct. 13, 2015, now Pat. No. 9,738,870, which is a continuation-in-part of application No. PCT/US2015/025909, filed on Apr. 15, 2015.

(60) Provisional application No. 62/053,588, filed on Sep. 22, 2014, provisional application No. 62/012,811, filed on Jun. 16, 2014, provisional application No. 62/002,084, filed on May 22, 2014, provisional application No. 62/189,105, filed on Jul. 6, 2015, provisional application No. 62/188,343, filed on Jul. 2, 2015.

(30) Foreign Application Priority Data

Apr. 15, 2014 (GR) .............................. 20140100217
Mar. 13, 2015 (GR) .............................. 20150100115

(51) Int. Cl.
| | | |
|---|---|---|
| A61K 35/66 | (2015.01) | |
| C12N 1/20 | (2006.01) | |
| A61K 9/00 | (2006.01) | |
| A61K 48/00 | (2006.01) | |
| A61Q 19/00 | (2006.01) | |
| A61K 35/74 | (2015.01) | |
| C07K 14/195 | (2006.01) | |
| C12R 1/01 | (2006.01) | |
| A61L 15/36 | (2006.01) | |
| C12Q 1/689 | (2018.01) | |
| C12N 1/00 | (2006.01) | |
| A01N 63/00 | (2006.01) | |
| A61K 8/99 | (2017.01) | |
| A61K 35/744 | (2015.01) | |
| A61K 35/745 | (2015.01) | |
| A61K 35/747 | (2015.01) | |
| A61Q 17/04 | (2006.01) | |
| C12Q 1/02 | (2006.01) | |
| A61Q 15/00 | (2006.01) | |
| A61Q 19/02 | (2006.01) | |
| A61Q 19/04 | (2006.01) | |

(52) U.S. Cl.
CPC .............. C12N 1/20 (2013.01); A01N 63/00 (2013.01); A61K 8/99 (2013.01); A61K 9/0014 (2013.01); A61K 35/74 (2013.01); A61K 35/744 (2013.01); A61K 35/745 (2013.01); A61K 35/747 (2013.01); A61K 48/00 (2013.01); A61L 15/36 (2013.01); A61Q 15/00 (2013.01); A61Q 17/04 (2013.01); A61Q 19/00 (2013.01); C07K 14/195 (2013.01); C12N 1/00 (2013.01); C12Q 1/02 (2013.01); C12Q 1/689 (2013.01); C12R 1/01 (2013.01); A61Q 19/02 (2013.01); A61Q 19/04 (2013.01)

(58) Field of Classification Search
CPC . C12N 1/01; C12N 1/20; A61K 35/66; A61K 35/74; A01N 63/00
See application file for complete search history.

(56) References Cited

U.S. PATENT DOCUMENTS

| | | |
|---|---|---|
| 3,984,575 A | 10/1976 | Farr |
| 4,147,807 A | 4/1979 | Gryczka et al. |
| 4,335,107 A | 6/1982 | Snoeyenbos et al. |
| 4,689,226 A | 8/1987 | Nurmi et al. |
| 4,720,344 A | 1/1988 | Ganczarczyk et al. |
| 5,139,792 A | 8/1992 | Ware et al. |
| 5,176,911 A | 1/1993 | Tosi et al. |
| 5,278,192 A | 1/1994 | Fung et al. |

(Continued)

FOREIGN PATENT DOCUMENTS

| | | |
|---|---|---|
| EP | 0761607 A1 | 3/1997 |
| EP | 0780419 A1 | 6/1997 |

(Continued)

OTHER PUBLICATIONS

Air Products 2004, MSDS, Version 1.4, Revision Date Apr. 4, 2004, pp. 1-6.
atcc.orglcommonlcatalog/wordSearch/results.cfm, total of 4 pages, (2006).
Bock et al., "Oxidation of Inorganic Nitrogen Compounds as Energy Source," In: The Prokaryotes. A Handbook on the Biology of Bacteria: Ecophysiology, Isolation, Identification, Applications. Edited by Balows et al. Springer-Verlag. Second Edition. 1992, vol. 1. Chapter 17, pp. 414-417.

(Continued)

*Primary Examiner* — Ruth A Davis
(74) *Attorney, Agent, or Firm* — Lando & Anastasi, LLP

(57) ABSTRACT

A method for treating a skin disorder, e.g., acne, e.g. acne vulgaris, in a subject is provided. The method comprises administering, e.g., applying, e.g., topically administering, ammonia oxidizing bacteria, e.g., a preparation comprising ammonia oxidizing bacteria, to a surface of the subject. Preparations comprising ammonia oxidizing bacteria for treating such skin disorder, e.g., acne, e.g. acne vulgaris in a subject are also provided.

15 Claims, 4 Drawing Sheets

(56) References Cited

U.S. PATENT DOCUMENTS

| | | |
|---|---|---|
| 5,314,542 A | 5/1994 | Cassidy et al. |
| 5,322,686 A | 6/1994 | Grahn et al. |
| 5,380,758 A | 1/1995 | Stamler et al. |
| 5,385,940 A | 1/1995 | Moskowitz |
| 5,396,882 A | 3/1995 | Zapol |
| 5,427,797 A | 6/1995 | Frostell et al. |
| 5,451,400 A | 9/1995 | Stern et al. |
| 5,519,020 A | 5/1996 | Smith et al. |
| 5,534,253 A | 7/1996 | Casas et al. |
| 5,570,683 A | 11/1996 | Zapol |
| 5,574,068 A | 11/1996 | Stamler et al. |
| 5,595,753 A | 1/1997 | Hechtman |
| 5,604,127 A | 2/1997 | Nisbet et al. |
| 5,632,981 A | 5/1997 | Saavedra et al. |
| 5,645,839 A | 7/1997 | Chobanian et al. |
| 5,646,181 A | 7/1997 | Fung et al. |
| 5,648,101 A | 7/1997 | Tawashi |
| 5,648,393 A | 7/1997 | Stamler et al. |
| 5,650,447 A | 7/1997 | Keefer et al. |
| 5,665,077 A | 9/1997 | Rosen et al. |
| 5,693,676 A | 12/1997 | Gorfine |
| 5,713,349 A | 2/1998 | Keaney |
| 5,714,511 A | 2/1998 | Saavedra et al. |
| 5,721,278 A | 2/1998 | Garfield et al. |
| 5,725,492 A | 3/1998 | Igo et al. |
| 5,728,705 A | 3/1998 | Lawson et al. |
| 5,765,548 A | 6/1998 | Perry |
| 5,767,160 A | 6/1998 | Kaesemeyer |
| 5,789,447 A | 8/1998 | Wink, Jr. et al. |
| 5,800,385 A | 9/1998 | Demopulos et al. |
| 5,801,203 A | 9/1998 | Lipton |
| 5,807,546 A | 9/1998 | Stern et al. |
| 5,814,656 A | 9/1998 | Saavedra et al. |
| 5,814,666 A | 9/1998 | Green et al. |
| 5,821,112 A | 10/1998 | Botto et al. |
| 5,824,669 A | 10/1998 | Garvey et al. |
| 5,834,030 A | 11/1998 | Bolton |
| 5,839,433 A | 11/1998 | Higenbottam et al. |
| 5,849,180 A | 12/1998 | Sumino et al. |
| 5,849,192 A | 12/1998 | Jagush et al. |
| 5,858,017 A | 1/1999 | Demopulos et al. |
| 5,861,168 A | 1/1999 | Cooke et al. |
| 5,873,359 A | 2/1999 | Zapol et al. |
| 5,891,472 A | 4/1999 | Russell |
| 5,892,658 A | 4/1999 | Urda et al. |
| 5,900,433 A | 5/1999 | Igo et al. |
| 5,904,938 A | 5/1999 | Zapol et al. |
| 5,910,316 A | 6/1999 | Keefer et al. |
| 5,910,482 A | 6/1999 | Yallampalli et al. |
| 5,912,019 A | 6/1999 | Singh |
| 5,958,427 A | 9/1999 | Salzman et al. |
| 5,994,444 A | 11/1999 | Trescony et al. |
| 7,314,748 B1 | 1/2008 | Fredenburgh et al. |
| 2004/0014188 A1 | 1/2004 | Whitlock |
| 2005/0036996 A1 | 2/2005 | Roussel et al. |
| 2005/0244382 A9 | 11/2005 | Whitlock |

FOREIGN PATENT DOCUMENTS

| | | |
|---|---|---|
| EP | 0987000 A1 | 3/2000 |
| FR | 2682296 A1 | 4/1993 |
| GB | 2020174 A | 11/1979 |
| JP | 59-135845 A | 8/1984 |
| JP | S63227515 A | 9/1988 |
| JP | 02-121665 A | 5/1990 |
| JP | 02-169092 A | 6/1990 |
| JP | 03-289957 A | 12/1991 |
| JP | 09-075984 A | 3/1997 |
| WO | 09827991 A1 | 7/1998 |
| WO | 0213982 A1 | 2/2002 |
| WO | 03057380 A2 | 7/2003 |
| WO | 2005030147 A2 | 4/2005 |

OTHER PUBLICATIONS

Brochures for Ultra Bac from ABI, Inc., Cleveland, OH, undated.
Catalogue of Bacteria and Phages. 1989. American Type Culture Collection. p. 152, col. 2.
Head et al., 1993, The Phylogeny of Autotrophic Ammonia-Oxidizing Bacteria as Determined by Analysis of 16s Ribosomal RNA Gene Sequences. Journal of General Microbiology, vol. 139, pp. 1147-1153.
Ida et al., 2004, Identification of Genus Nitrosovibrio, Ammonia-Oxidizing Bacteria by Comparison of N-Terminal Amino Acid Sequences of Phosphoglycerate Kinase, Journal of Bioscience and Bioengineering, vol. 98, No. 5, pp. 380-383.
Norton et al., "Diversity of ammonia monooxygenase operon in autotrophic ammonia-oxidizing bacteria," Archives of Microbiology, vol. 177, No. 2, pp. 139-149 (Feb. 2002).
Stein et al., "Whole-genome analysis of the ammonia-oxidizing bacterium, Nitrosomonas eutrophra C91: implications for niche adaption," Environmental Microbiology, vol. 9, No. 12, pp. 2993-3007 (Dec. 2007).
Suwa et al., "Phylogenetic relationships of activated sludge isolates of ammonia oxidizers with different sensitivities to ammonium sulfate," Journal of General and Applied Microbiology, vol. 43, pp. 373-379 (Jan. 1, 1997).
MedicineNet, 1998, Definition of Vagina, p. 1 of 1. Last Editorial Review: Mar. 26, 1998: http://www.medicinenet.com/script/main/art.asp?articlekey=5951 Printed Nov. 27, 2009.

AMMONIA OXIDIZING BACTERIA FOR TREATMENT OF ECZEMA

CROSS-REFERENCE TO RELATED APPLICATIONS

This application is a continuation of U.S. patent application Ser. No. 14/882,284, filed Oct. 13, 2015, which claims priority to U.S. Provisional Application No. 62/188,343, filed Jul. 2, 2015, U.S. Provisional Application No. 62/189,105, filed Jul. 6, 2015, and is a continuation-in-part of International Patent Application No. PCT/US2015/025909, filed Apr. 15, 2015, which in turn claims priority to Greek Patent Application Number 20140100217, filed Apr. 15, 2014, U.S. Provisional Application No. 62/002,084, filed May 22, 2014, U.S. Provisional Application No. 62/012,811, filed Jun. 16, 2014, U.S. Provisional Application No. 62/053,588, filed Sep. 22, 2014, and Greek Patent Application Number 20150100115, filed Mar. 13, 2015, the content of each of which is incorporated herein by reference in its entirety for all purposes.

SEQUENCE LISTING

The instant application contains a Sequence Listing which has been submitted electronically in ASCII format and is hereby incorporated by reference in its entirety. Said ASCII copy, created on Jan. 25, 2016, is named N2060-700130_SL.txt and is 3,591,125 bytes in size.

BACKGROUND

Beneficial bacteria can be used to suppress the growth of pathogenic bacteria. Bacteria and other microorganisms are ubiquitous in the environment. The discovery of pathogenic bacteria and the germ theory of disease have had a tremendous effect on health and disease states. Bacteria are a normal part of the environment of all living things. In the gut, these bacteria are not pathogenic under normal conditions, and in fact improve health by rendering the normal intestinal contents less hospitable for disease causing organisms. Disease prevention is accomplished in a number of ways: nutrients are consumed, leaving less for pathogens; conditions are produced, such as pH and oxygen tension, which are not hospitable for pathogens; compounds are produced that are toxic to pathogens; pathogens are consumed as food by these microorganisms; less physical space remains available for pathogens; and specific binding sites are occupied leaving fewer binding sites available for pathogens. The presence of these desirable bacteria is seen as useful in preventing disease states.

There is a need in the art for improved beneficial bacteria that can suppress the growth of pathogenic bacteria, for example, with regard to the treatment of skin conditions, e.g., acne, e.g., acne vulgaris.

Acne is the most common skin disease and the top reported cause for dermatologist visitations, accounting for about one-fourth of U.S. dermatologists' patient volume. Traditionally thought of as a trivial, "normal" condition, acne has recently been medically redefined to be a chronic disease, one that can significantly impact an individual's quality of life with social, psychological and emotional impairments that are comparable to those reported by patients with epilepsy, asthma, diabetes or arthritis. In the United States alone, acne affects approximately 40 to 50 million people, 20-25% suffer from moderate-to-severe acne. U.S. sales of the Top 10 Branded acne therapeutics have a $3 billion run rate and are comprised of $1.5 billion in systemic retinoids, $700 million in oral antibiotics, $600 million in topic antibiotics and $240 million in topical retinoids. Globally, the prevalence of acne is approximately 80% among adolescents and 50% among young adults. Despite the significant spend on prescription and over the counter remedies, acne remains an area of significant unmet medical need as treatments are either marginally effective (topical antibiotics, topical retinoids, astringents) and/or associated with serious risks (oral retinoids). In addition to the need for a safe and effective product to prevent and treat inflammatory and non-inflammatory acne lesions, there is a substantial unmet need and commercial opportunity for a topical therapy that targets excess sebum production.

TABLE 1

| | Acne Severity | | | | |
| --- | --- | --- | --- | --- | --- |
| | Mild | Moderate | | | |
| | Comedonal blackheads/white heads | Mixed and papular/pustular | Nodular | | Severe Nodular/conglobate |
| First-line | Topical retinoid | Topical retinoid + topical antimicrobial | Oral antibiotic + topical retinoid +/− benzoyl peroxide | Oral antibiotic + topical retinoid +/− benzoyl peroxide | Oral isotretinoin[3] |
| Second-line/ Alternatives[1] | Alternative topical retinoid or azelaic acid or salicylic acid | Alternative topical retinoid; antimicrobial agent + alternative topical retinoid or azelaic acid | Alternative oral antibiotic + alternative topical retinoid +/− benzyoly peroxide | Oral isotretinoin or alternative oral antibiotic + alternative topical retinoid +/− benzoyl peroxide azelaic acid | High dose oral antibiotic + topical retinoid + benzoyl peroxide |

TABLE 1-continued

| | Acne Severity | | | | |
|---|---|---|---|---|---|
| | Mild | | Moderate | | |
| | Comedonal blackheads/white heads | Mixed and papular/pustular | Nodular | | Severe Nodular/conglobate |
| Alternatives for females[1,4] | See first-line options | See first-line options | Oral anti-androgen[5] + topical retinoid/ azelaic acid +/− topical antimicrobial | Oral anti-androgen[5] + topical retinoid/ azelaic acid +/− topical antimicrobial | High dose oral anti-androgen + topical retinoid +/− alternative topical antimicrobial |
| Maintenance therapy: | Topical retinoid | | Topical Retinoid +/− benzoyl peroxide | | |

Source: Global Data; adapted from AcneAcademy, 2010.
[1]consider physical removal of comedones;
2 - with small nodules (<.5 cm);
[3]second course in case of relapse;
[4]for pregnancy; options are limited;
[5]for further information refer to Gollnick et al., 2003.

An ideal target product may have one or more of the following properties: self-administered (e.g., once daily, e.g., twice daily); odorless, colorless and invisible; not associated with increased sensitivity to sunlight; safe, non-toxic if ingested/inhaled and well tolerated on the skin, adjacent mucous membranes and eyes; suitable for both treatment and maintenance therapy without the risk of fostering antibiotic resistance; and acts locally to (in order of priority): reduce the frequency of lesions (antibiotic, anti-inflammatory); reduce the duration of lesions (improved healing); reduce the inflammation of lesions (anti-inflammatory); potentially prevent or reduce aberrant pigmentation and scarring (improved healing); speed the healing of damaged skin (improved healing); reduce the production of excess sebum; and decrease the presence of pathogenic bacteria (antibiotic).

SUMMARY

The present disclosure provides for a method of treating a skin disorder, e.g., acne, e.g. acne vulgaris, of a subject. The method comprises administering, e.g., applying, e.g., topically administering, ammonia oxidizing bacteria, e.g., a preparation comprising ammonia oxidizing bacteria, to a surface of the subject.

In some embodiments, an amount and a frequency of administration, e.g., application, is sufficient to reduce the amount or concentration of pathogenic bacteria, e.g., *Propionibacterium acnes*, on the surface of the subject. In some instances the amount is a therapeutically effective dose of ammonia oxidizing bacteria. In some instances, the skin disorder is acne, e.g., acne vulgaris.

In some embodiments, administering provides for treatment of inflammatory lesions, e.g., papules, pustules, cysts/nodules. In some embodiments, administering provides for treatment of non-inflammatory lesions, e.g., open comedones, closed comedones. In some embodiments, administering provides for treatment or improvement of post-inflammatory hyperpigmentation/post inflammatory erythema (PIH/PIE) lesions. In some embodiments, administering provides for treatment or improvement of one or more of erythema, edema, scaling, stinging, burning, and itching. In some embodiments, administering provides for treatment or improvement of one or more of oily appearance, pore appearance, radiance, blotchiness, skin tone evenness, visual smoothness, and tactile smoothness. In some embodiments, administering provides for treatment or improvement in sebumeter measurements.

In some embodiments, administering comprises pre-treating the subject with ammonia oxidizing bacteria. In some embodiments, topically administering comprises topically administering prior to occurrence of the skin disorder. In some embodiments, topically administering comprises topically administering to the subject an effective dose of ammonia oxidizing bacteria. In some instances, the effective dose is about $0.1 \times 10^9$, $0.2 \times 10^9$, $0.3 \times 10^9$, $0.4 \times 10^9$, $0.5 \times 10^9$, $0.6 \times 10^9$, $0.7 \times 10^9$, $0.8 \times 10^9$, $0.9 \times 10^9$, $1.0 \times 10^9$, $1.2 \times 10^9$, $1.4 \times 10^9$, $1.5 \times 10^9$, $1.6 \times 10^9$, $1.8 \times 10^9$, $2.0 \times 10^9$, $2.2 \times 10^9$, $2.4 \times 10^9$, $2.6 \times 10^9$, $2.8 \times 10^9$, $3.0 \times 10^9$, $3.2 \times 10^9$, $3.4 \times 10^9$, $3.6 \times 10^9$, $3.8 \times 10^9$, $4.0 \times 10^9$, $4.2 \times 10^9$, $4.4 \times 10^9$, $4.6 \times 10^9$, $4.8 \times 10^9$, $5.0 \times 10^9$, $5.5 \times 10^9$, $6.0 \times 10^9$, $6.5 \times 10^9$, $7.0 \times 10^9$, $7.5 \times 10^9$, $8.0 \times 10^9$, $8.5 \times 10^9$, $9.0 \times 10^9$, $9.5 \times 10^9$, $10.0 \times 10^9$, $12 \times 10^9$, $14 \times 10^9$, $16 \times 10^9$, $18 \times 10^9$, $20 \times 10^9$, $25 \times 10^9$, $30 \times 10^9$, $40 \times 10^9$, $50 \times 10^9$ CFU.

In some embodiments, the skin disorder is at a target site of the subject and comprises one or more undesirable bacteria, e.g., pathogenic bacteria. In some instances, the target sight comprises *Propionibacterium acnes*.

In some embodiments, the method further comprises determining whether the subject is in need of treating the skin disorder, e.g., determining whether the subject it in need of treating acne, e.g., acne vulgaris. In some embodiments, the method further comprises selecting the subject in need of treating the skin disorder.

In some embodiments, the ammonia oxidizing bacteria, e.g., preparation comprising ammonia oxidizing bacteria may be in a form that may be capable of being aerosolized, sprayed or misted, i.e., in the form of a mist. In some embodiments, the ammonia oxidizing bacteria, e.g., preparation may be applied as an aerosol or mist, e.g., in an aqueous medium. In some embodiments, the ammonia oxidizing bacteria, e.g., preparation of ammonia oxidizing bacteria may be ammonia oxidizing bacteria in a buffer solution, e.g., aqueous buffer solution. In some instances, the buffer solution, e.g., aqueous buffer solution, comprises disodium phosphate and magnesium chloride, for example, 50 mM $Na_2HPO_4$ and 2 mM $MgCl_2$ in water. In some instances the buffer solution e.g., aqueous buffer solution, consists essentially of disodium phosphate and magnesium chloride, for example, 50 mM $Na_2HPO_4$ and 2 mM $MgCl_2$ in water. In some instances, the buffer solution, e.g., aqueous buffer solution, consists of disodium phosphate and magnesium chloride, for example, 50 mM $Na_2HPO_4$ and 2 mM $MgCl_2$ in water.

In some embodiments, the method further comprises selecting the subject on the basis of the subject being in need of a reduction of the amount or concentration of pathogenic bacteria, e.g., *Propionibacterium acnes*, on the surface of the subject. In some embodiments, the ammonia oxidizing bacteria is self-administered.

In some embodiments, the ammonia oxidizing bacteria applied to any one or more of the face, neck, and scalp of the subject.

In some embodiments, the preparation comprises at least one of ammonia, ammonium salts, and urea. In some instances, the preparation comprises a controlled release material, e.g., slow release material. In some instances, the preparation of ammonia oxidizing bacteria, further comprises an excipient, e.g., one of a pharmaceutically acceptable excipient or a cosmetically acceptable excipient. In some instances, the excipient, e.g., one of the pharmaceutically acceptable excipient and the cosmetically acceptable excipient, is a surfactant. In some instances, the preparation is substantially free of other organisms. In some instances, the preparation is disposed in a powder, cosmetic, cream, stick, aerosol, e.g., mist, salve, wipe, or bandage. In some instances, the preparation is provided as a powder, cosmetic, cream, stick, aerosol, e.g., mist, salve, wipe, or bandage. In some instances, the preparation comprises a moisturizing agent, deodorizing agent, cent, colorant, insect repellant, cleansing agent, or UV-blocking agent. In some instances the excipient, e.g., the pharmaceutically acceptable excipient or the cosmetically acceptable excipient, comprises an anti-adherent, binder, coat, disintegrant, filler, flavor, color, lubricant, glidant, sorbent preservative, or sweetener.

In some instances, the preparation comprising ammonia oxidizing bacteria comprises about $10^8$ to about $10^{14}$ CFU/L. In some instances, the preparation comprising ammonia oxidizing bacteria comprises about $10^8$ to about $10^{14}$ CFU/mL. In some instances, the preparation comprises between about $1 \times 10^9$ CFU/L to about $10 \times 10^9$ CFU/L. In some instances, the preparation comprises between about $1 \times 10^9$ CFU/mL to about $10 \times 10^9$ CFU/mL.

In some embodiments, the preparation comprising ammonia oxidizing bacteria comprises between about 50 milligrams (mg) and about 1000 mg of ammonia oxidizing bacteria. In some instances, the mass ratio of ammonia oxidizing bacteria to the excipient, e.g., the pharmaceutically acceptable excipient or the cosmetically acceptable excipient is in a range of about 0.1 grams to about 1 gram per liter.

In some embodiments, the ammonia oxidizing bacteria is selected from the group consisting of *Nitrosomonas, Nitrosococcus, Nitrosospira, Nitrosocystis, Nitrosolobus, Nitrosovibrio*, and combinations thereof. In some instances, the ammonia oxidizing bacteria is *Nitrosomonas eutropha* (*N. eutropha*). In some instances, the ammonia oxidizing bacteria is *N. eutropha* D23, having ATCC accession number PTA-121157.

In some embodiments, the preparation comprises an organism selected from the group consisting of *Lactobacillus, Streptococcus, Bifidobacter*, and combinations thereof.

In some embodiments, the method is provided to deliver a cosmetic product. In some embodiments, the method is provided to deliver a therapeutic product.

In some embodiments, the preparation is provided in a container, the preparation and the container having a weight of less than about 50, 100, 200, 300, 400, 500, 600, 700, 800, 900, 1000, 1500, or 2000 grams.

In some embodiments, the preparation is applied about 1, 2, 3, 4, 5, 6, 7, 8, 9, 10, 11, 12, 13, 14, 15, 16, 17, 18, 19, 20, 21, 22, 23, or 24 times per day. In some instances, the preparation is applied one time per day. In some instances, the preparation is applied two times per day.

In some embodiments, the preparation is applied for about 1-3, 3-5, 5-7, 7-9, 5-10, 10-14, 12-18, 12-21, 21-28, 28-35, 35-42, 42-49, 49-56, 46-63, 63-70, 70-77, 77-84, or 84-91 days. In some instances, the preparation is applied for about 7 days. In some instances, the preparation is applied for about 14 days. In some instances, the preparation is applied for about 21 days. In some instances, the preparation is applied for about 28 days.

In some embodiments, the method further comprises obtaining a sample from the surface of the skin. In some instances, the method further comprises isolating DNA of bacteria in the sample. In some instances, the method further comprises sequencing DNA of bacteria in the sample. In some instances, the bacteria is *Propionibacterium acnes*.

In some embodiments, administering the ammonia oxidizing bacteria provides for a decrease in *Propionibacterium acnes*. In some instances, the *Propionibacterium acnes* decreases, e.g., a concentration of *Propionibacterium acnes* decreases, after about 1, 2, 3, 4, 5, 6, 7, 8, 9, 10, 11, 12, 13, 14, 15, 16, 17, 18, 19, 20, 21, 22, 23, 24, 25, 26, 27, or 28 days.

In some embodiments, the method further comprises administering, e.g., self-administering, one or more of a shampoo, a conditioner, and a cleanser, e.g., a facial cleanser. In certain instances, any one or more of shampoo, conditioner, and facial cleanser is applied 1 time per day. In certain instances, the shampoo used was Lot 293178. In certain instances, the cleanser used was Lot 293162. In certain instances, at least one of a shampoo, conditioner, and soap was used subsequent to discontinuing of administration of the ammonia oxidizing bacteria. In certain instances, at least one of the shampoo, conditioner, and soap was used subsequent to discontinuation of the preparation of ammonia oxidizing bacteria.

In some embodiments, the subject was evaluated prior to beginning treatment, e.g., administering the ammonia oxidizing bacteria. In some embodiments, the subject was evaluated 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 days; or 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 weeks; or 2.3 years, 4, or 5 years after beginning treatment, e.g., administering the ammonia oxidizing bacteria.

In some embodiments, administering ammonia oxidizing bacteria, e.g., the preparation of ammonia oxidizing bacteria, provides for one or more of the following: reduces inflammation of lesions, reduces the frequency of lesions, and decreases the presence of pathogenic bacteria, e.g., *Propionibacterium acnes*. In some instances, administering the preparation provides for reduction of inflammation of lesions. In some instances, administering the preparation provides for reduction of inflammation of lesions in adults. In some instances, administering the preparation provides for reducing in the frequency of lesions. In some instances, administering the preparation provides for decreasing the presence of pathogenic bacteria, e.g., *Propionibacterium acnes*. In some instances, administering the preparation provides for an improvement in the subject's emotional assessment of their disease as measured by Skindex16 Quality-of-Life Survey. In some instances, administering the preparation provides for an improvement in one or more of the following: skin condition hurting in the subject, persistence/reoccurrence of skin condition in the subject, and appearance of skin condition in the subject. In some instances, administering the preparation provides for an improvement (decrease) in one or more of the following, according to clinical grading: grading scores for visual and tactile smoothness, and blotchiness.

In some embodiments, the subject is female. In other embodiments, the subject is male. In some instances, the subject is one of the following ethnicity/race: Asian, black or African American, Hispanic or Latino, white, or multiracial. In some instances, the subject is characterized as having at least one of the following skin types: normal, oily, and combination skin. In some instances, the subject is characterized as having one of the following Fitzpatrick skin types: I, II, III, IV, V. In some instances, the acne is characterized as adolescent acne. In some instances, the acne is characterized as adult acne. In some instances, the age of the subject is between about 12-15, 16-18, 19-28, or greater than 28.

In some embodiments, an acne treatment selected from the group consisting of: a topical retinoid, azaelaic acid, salicylic acid, a topical antimicrobial, an oral antibiotic, benzoyl peroxide, an oral anti-androgen, an oral isotretinoin, and combinations thereof is administered to the subject. In some embodiments, the acne treatment is administered for a period of time prior to commencing administration of the ammonia oxidizing bacteria. In some embodiments, the acne treatment is continued throughout a time period for administration of the ammonia oxidizing bacteria. In some embodiments, the acne treatment is administered for a period of time prior to commencing administration of ammonia oxidizing bacteria and is ceased prior to commencement of administration of the ammonia oxidizing bacteria. In some embodiments, the acne treatment is ceased during the administration of the ammonia oxidizing bacteria. In some embodiments, the acne treatment is continued throughout administration of the ammonia oxidizing bacteria. In some embodiments, the acne treatment is commenced subsequent to ceasing administration of ammonia oxidizing bacteria.

In some embodiments, administration occurs 30, 60, 90, 120, 150, 180 minutes before the subject cleanses or showers.

In some embodiments, a preparation comprising ammonia oxidizing bacteria, as recited above, or in any portion of this disclosure, for the treatment of a skin condition, e.g., acne, e.g., acne vulgaris is provided.

The disclosure contemplates all combinations of any one or more of the foregoing aspects and/or embodiments, as well as combinations with any one or more of the embodiments set forth in the detailed description and examples.

DETAILED DESCRIPTION

Figure 1:
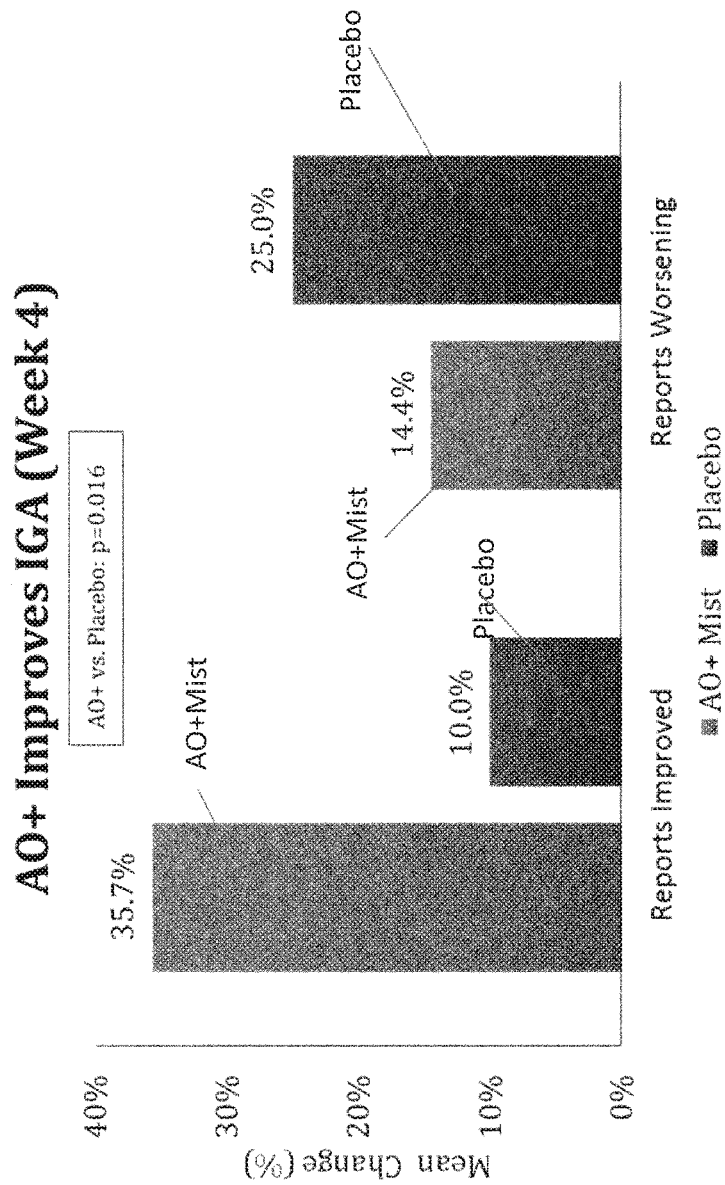
FIG. 1 shows the improvement of IGA using ammonia oxidizing bacteria (AO+Mist) at Week 4. Mean change (%) is plotted versus report of improvement and report of worsening in AO+Mist and Placebo.

The present disclosure provides for methods of treating skin conditions, e.g., acne, e.g., acne vulgaris. The methods comprise administering to a subject ammonia oxidizing bacteria, for example, a preparation comprising ammonia oxidizing bacteria.

Preparations, compositions, and formulations, e.g., including non-natural products, natural products, and fortified natural products, comprising, consisting essentially of, or consisting of ammonia oxidizing bacteria are contemplated for use in treatment of a skin condition, e.g., acne, e.g., acne vulgaris. Compositions for use in the treatment of a skin condition, e.g, acne vulgaris, e.g., acne in a subject are contemplated comprising ammonia oxidizing bacteria, e.g., a preparation comprising ammonia oxidizing bacteria.

Ammonia-oxidizing bacteria (AOB) of the genus *Nitrosomonas* are Gram-negative obligate autotrophic bacteria with a unique capacity to generate nitrite and nitric oxide exclusively from ammonia as an energy source. They are widely present both in soil and water environments and are essential components of environmental nitrification processes. Due to the roles of nitrite and nitric oxide on human skin as important components of several physiological functions, such as vasodilation, skin inflammation and wound healing, these bacteria may have beneficial properties for both healthy and immunopathological skin conditions. These bacteria are safe for use in humans because they are slow-growing, cannot grow on organic carbon sources, may be sensitive to soaps and antibiotics, and have never been associated with any disease or infection in animals or humans.

Ammonia oxidizing bacteria are ubiquitous Gram-negative obligate chemolithoautotrophic bacteria with a unique capacity to generate energy exclusively from the conversion of ammonia to nitrite.

In some embodiments, ammonia oxidizing bacteria catalyze the following reactions.

At a neutral pH, ammonia generated from ammonium around neutral pH conditions is the substrate of the initial reaction. The conversion of ammonia to nitrite takes place in two steps catalyzed respectively by ammonia monooxygenase (Amo) and hydroxylamine oxidoreductase (Hao), as follows:

$$NH_3 + 2H^+ + 2e^- + O_2 \rightarrow NH_2OH + H_2O \quad (A)$$

$$NH_2OH + H_2O \rightarrow NO_2^- + 4e^- + 5H^+ \quad (B)$$

In some instances, reaction B is reported as follows, to indicate nitrous acid ($HNO_2$) formation at low pH:

$$NH_2OH + H_2O \rightarrow HNO_2 + 4e^- + 4H^+$$

In certain embodiments, $NH_4^+$ and $NH_3$ may be used interchangeably throughout the disclosure.

The present disclosure provides for ammonia oxidizing bacteria, e.g., preparations comprising ammonia oxidizing bacteria that may:

Reduces inflammation of lesions (e.g., in an adult)
Reduce the frequency of lesions; and
Decrease the presence of pathogenic bacteria The ammonia oxidizing bacteria, e.g., preparations comprising ammonia oxidizing bacteria may also:

Reduce the duration of lesions
Prevent or reduce aberrant pigmentation and scarring
Shorten healing period of damaged skin; and
Reduce production of excess sebum (e.g., oily secretion of sebaceous glands).

The present disclosure provides for preparations comprising ammonia oxidizing bacteria for use in the treatment of a skin condition, e.g., acne, e.g., acne vulgaris, wherein the preparation may be one or more of the following: self-administered (e.g., 1-2 times daily), odorless, colorless, invisible, not associated with increased sensitivity to sunlight, safe, non-toxic, well tolerated on the skin (e.g., adjacent mucous membranes and eyes), suitable for children under 12, and suitable for both treatment and maintenance therapy without the risk of fostering antibiotic resistance.

Ammonia oxidizing bacteria, e.g., *N. eutropha*, for example *N. eutropha* referred to as "D23", also known as "B244" or "AOB D23-100" may have several of the above-described properties.

1. Definitions

An ammonia oxidizing bacterium refers to a bacterium capable of oxidizing ammonia or ammonium to nitrite at a rate, e.g., a substantial rate, e.g., a pre-determined rate. The rate, e.g., a pre-determined rate, may refer to the conversion of ammonium ions ($NH_4^+$) (e.g., at about 200 mM) to nitrite ($NO_2^-$) at a rate of at least 50, 75, 125, or 150 micromoles $NO_2^-$ per minute, e.g., about 100-150, 75-175, 75-125, 100-125, 125-150, or 125-175 micromoles/minute, e.g., about 125 micromoles $NO_2^-$ per minute. In embodiments, the rate, e.g., a pre-determined rate, may refer to the conversion of ammonium ions ($NH_4^+$) (e.g., at about 200 mM) to nitrite ($NO_2^-$) at a rate of at least 50, 75, 125, or 150 nanomoles $NO_2^-$ per minute per ml, e.g., about 100-150, 75-175, 75-125, 100-125, 125-150, or 125-175 nanomoles/minute/ml, e.g., about 125 nanomoles $NO_2^-$ per minute per ml for a continuous culture, for example having an OD of about 0.5.

Examples of ammonia oxidizing bacteria include *Nitrosomonas eutropha* strains, e.g., D23 and C91, and other bacteria in the genera *Nitrosomonas, Nitrosococcus, Nitrosospira, Nitrosocystis, Nitrosolobus*, and *Nitrosovibrio*. D23 *Nitrosomonas eutropha* strain refers to the strain, designated AOB D23-100, deposited with the American Tissue Culture Collection (ATCC) (10801 University Blvd., Manassas, Va., USA) on Apr. 8, 2014 having accession number PTA-121157. The nucleic acid sequence(s), e.g., genome sequence, of accession number PTA-121157 are hereby incorporated by reference in their entireties. In certain embodiments, the *N. eutropha* is a strain described in PCT Application No. PCT/US2015/025909, filed Apr. 15, 2015, herein incorporated by reference in its entirety. "AOB D23-100" may also be referred to as D23 or B244 throughout this disclosure.

Each and every nucleic acid sequence and amino acid sequence disclosed in PCT Application No. PCT/US2015/025909, filed Apr. 15, 2015, is herein incorporated by reference in its entirety. Any ammonia oxidizing bacteria disclosed in PCT Application No. PCT/US2015/025909, filed Apr. 15, 2015, is herein incorporated by reference in its entirety.

Optimized *Nitrosomonas eutropha* (*N. eutropha*), as that term is used herein, refers to an *N. eutropha* having an optimized growth rate; an optimized $NH_4^+$ oxidation rate; or optimized resistance to $NH_4^+$. In an embodiment it differs from naturally occurring *N. eutropha* by at least one nucleotide, e.g., a nucleotide in a gene selected from ammonia monooxygenase, hydroxylamine oxidoreductase, cytochrome c554, and cytochrome $c_M552$. The difference can arise, e.g., through selection of spontaneously arising mutation, induced mutation, or directed genetic engineering, of the *N. eutropha*. In an embodiment it differs from a naturally occurring *N. eutropha* in that it has a constellation of alleles, not present together in nature. These differences may provide for one or more of a treatment or prevention of a skin disorder, a treatment or prevention of a disease or condition associated with low nitrite levels, a treatment or prevention of body odor, a treatment to supply nitric oxide to a subject, and a treatment to inhibit microbial growth.

As used herein, "axenic" refers to a composition comprising an organism that is substantially free of other organisms. For example, an axenic culture of ammonia oxidizing bacteria is a culture that is substantially free of organisms other than ammonia oxidizing bacteria. For example, an axenic culture of *N. eutropha* is a culture that is substantially free of organisms other than *N. eutropha*. In some embodiments, "substantially free" denotes undetectable by a method used to detect other organisms, e.g., plating the culture and examining colony morphology, or PCR for a conserved gene such as 16S RNA. An axenic composition may comprise elements that are not organisms, e.g., it may comprise nutrients or excipients. Any embodiment, preparation, composition, or formulation of ammonia oxidizing bacteria discussed herein may comprise, consist essentially of, or consist of optionally axenic ammonia oxidizing bacteria.

Throughout this disclosure, formulation may refer to a composition or preparation.

As used herein, an "autotroph", e.g., an autotrophic bacterium, is any organism capable of self-nourishment by using inorganic materials as a source of nutrients and using photosynthesis or chemosynthesis as a source of energy. Autotrophic bacteria may synthesize organic compounds from carbon dioxide and ATP derived from other sources, oxidation of ammonia to nitrite, oxidation of hydrogen sulfide, and oxidation of $Fe^{2+}$ to $Fe^{3+}$ Autotrophic bacteria of the present disclosure are incapable of causing infection.

Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated. In some embodiments, the delivery of one treatment is still occurring when the delivery of the second begins, so that there is overlap. This is sometimes referred to herein as "simultaneous" or "concomitant" or "concurrent delivery". In other embodiments, the delivery of one treatment ends before the delivery of the other treatment begins. This is sometimes referred to herein as "successive" or "sequential delivery." In embodiments of either case, the treatment is more effective because of combined administration. For example, the second treatment is a more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive (i.e., synergistic). The delivery can be such that an effect of the first treatment delivered is still detectable when the second is delivered. In some embodiments, one or more treatment may be delivered prior to diagnosis of the patient with the disorder.

Complete *N. europaea* medium refers to the *N. europaea* growth medium described in Ensign et al., "In vitro activation of ammonia monooxygenase from *Nitrosomonas europaea* by copper." J Bacteriol. 1993 April; 175(7):1971-80.

To "culture" refers to a process of placing an amount of a desired bacterium under conditions that promote its growth, i.e., promoting cell division. The conditions can involve a specified culture medium, a set temperature range, and/or an agitation rate. Bacteria can be cultured in a liquid culture or on plates, e.g., agar plates.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

The terms "nucleic acid," "nucleic acid sequence," "nucleotide sequence," or "polynucleotide sequence," and "polynucleotide" are used interchangeably. They refer to a polymeric form of nucleotides of any length, e.g., deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a nonnatural arrangement.

As used herein, the term "optimized growth rate" refers to one or more of: a doubling time of less than about 4, 5, 6, 7, 8, 9, or 10 hours when cultured under batch conditions as described herein in Example 2; a doubling time of less than about 16, 18, 20, 22, 24, or 26 hours, when grown under chemostat conditions as described herein in Example 2; or growing from an OD600 of about 0.15 to at least about 0.3, 0.4, 0.5, 0.6, 0.7, or 0.8 over about 1 or 2 days. In an embodiment, optimized growth rate is one having a doubling time that it is at least 10, 20, 30, 40, or 50% shorter than that of a naturally occurring *N. eutropha*.

As used herein, "optimized $NH_4^+$ oxidation rate" refers to a rate of at least about 50, 75, 125, or 150 micromoles per minute of converting $NH_3$ or $NH_4^+$ into $NO_2^-$. For instance, the rate may be at least about 50, 75, 125, or 150 micromoles per minute of converting $NH_4^+$ (e.g., at about 200 mM) to $NO_2^-$. In an embodiment, an optimized $NH_4^+$ oxidation rate is one in which $NH_3$ or $NH_4^+$ is converted into $NO_2^-$, at least 10, 20, 30, 40, or 50% more rapidly than is seen with a naturally occurring *N. eutropha*.

Percent (%) amino acid sequence identity, with respect to the amino acid sequences here (e.g., proteins expressed by *N. eutropha* D23) is defined as the percentage of amino acid residues in a candidate sequence that are identical with the amino acid residues in the reference sequence, which may be a naturally-occurring *N. eutropha* sequence or an *N. eutropha* D23 sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the means of those skilled in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. For instance, the WU-BLAST-2 software may be used to determine amino acid sequence identity (Altschul et al, Methods in Enzymology 266, 460-480 (1996); http://blast.wustl/edu/blast/README.html). WU-BLAST-2 uses several search parameters, most of which are set to the default values. The adjustable parameters are set with the following values: overlap span=1, overlap fraction=0.125, world threshold (T)=I 1. HSP score (S) and HSP S2 parameters are dynamic values and are established by the program itself, depending upon the composition of the particular sequence, however, the minimum values may be adjusted as appropriate.

Amino acid substitutions can be the result of replacing one amino acid with another amino acid having similar structural and/or chemical properties, such as the replacement of a leucine with a serine, i.e., conservative amino acid replacements. Typical but not limiting conservative substitutions are the replacements, for one another, among the aliphatic amino acids Ala, Val, Leu and Ile; interchange of Ser and Thr containing hydroxy residues, interchange of the acidic residues Asp and Glu, interchange between the amide-containing residues Asn and Gln, interchange of the basic residues Lys and Arg, interchange of the aromatic residues Phe and Tyr, and interchange of the small-sized amino acids Ala, Ser, Thr, Met and Gly. Additional conservative substitutions include the replacement of an amino acid by another of similar spatial or steric configuration, for example the interchange of Asn for Asp, or Gln for Glu. Amino acid substitutions can also be the result of replacing one amino acid with another amino acid having dis-similar structural and/or chemical properties, i.e., non-conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in the in vivo or in vitro assays for, e.g., metabolizing urea or ammonia.

Percent (%) sequence identity with respect to the nucleic acid sequences here (e.g., the *N. eutropha* D23 genome and portions thereof) is defined as the percentage of nucleotides in a candidate sequence that are identical with the nucleotides in the reference sequence, which may be a naturally-occurring *N. eutropha* sequence or an *N. eutropha* D23 sequence, after aligning the sequences and introducing gaps, if necessary, to achieve the maximum percent sequence identity. Alignment for purposes of determining percent nucleotide sequence identity can be achieved in various ways that are within the means of those skilled in the art, for instance, using publicly available computer software such as BLAST. Those skilled in the art can determine appropriate parameters for measuring alignment, including any algorithms needed to achieve maximal alignment over the full length of the sequences being compared.

The terms "polypeptide", "peptide" and "protein" (if single chain) are used interchangeably herein to refer to amino acid polymers. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

As used herein, "optimized resistance to $NH_4^+$" refers to an ability to grow in conditions of greater than 50, 75, 100, 125, 150, 175, 200, 225, 250, 275, or 300 mM $NH_3$ or $NH_4^+$ for at least about 24 or 48 hours. In an embodiment, an optimized resistance to $NH_4^+$ refers to the ability to grow at least 10, 20, 30, 40, or 50% more rapidly, or at least 10, 20, 30, 40, or 50% longer, in the presence of a selected concentration of $NH_3$ or $NH_4^+$ than can a naturally occurring *N. eutropha*.

As used herein with respect to a comparison between nucleic acid or protein sequences, "similar" means having homology. A similar gene or protein may comprise, e.g., substitutions (such as conservative or non-conservative substitutions), insertions (e.g., of at least 1, 2, 3, 4, 5, 10, 15, 20, 25, 30 amino acids, and for example up to 2, 3, 4, 5, 10, 15, 20, 25, 30, or 50 amino acids, or any positive combination thereof, or the number of nucleotides necessary to encode said amino acids), or deletions (e.g., of at least 1, 2, 3, 4, 5, 10, 15, 20, 25, 30 amino acids, and for example up to 2, 3, 4, 5, 10, 15, 20, 25, 30, or 50 amino acids, or any positive combination thereof, or the number of nucleotides necessary to encode said amino acids), or any combination thereof. Each of substitutions, insertions, and deletions may be positioned at the N-terminus, C-terminus, or a central region of the protein or gene. In embodiments, a conservative substitution is one that does not alter the charge and/or polarity and/or approximate size and/or geometry at the substituted position.

As used herein, a "subject" may include an animal, a mammal, a human, a non-human animal, a livestock animal, or a companion animal. The term "subject" is intended to include human and non-human animals, for example, vertebrates, large animals, and primates. In certain embodiments, the subject is a mammalian subject, and in particular embodiments, the subject is a human subject. Although applications with humans are clearly foreseen, veterinary applications, for example, with non-human animals, are also envisaged herein. The term "non-human animals" of the disclosure includes all vertebrates, for example, non-mammals (such as birds, for example, chickens; amphibians; reptiles) and mammals, such as non-human primates, domesticated, and agriculturally useful animals, for example, sheep, dog, cat, cow, pig, rat, among others.

As used herein, "transgenic" means comprising one or more exogenous portions of DNA. The exogenous DNA is derived from another organism, e.g., another bacterium, a bacteriophage, an animal, or a plant.

As used herein, "treatment of a disease or condition" refers to reducing the severity or frequency of at least one symptom of that disease or condition, compared to a similar but untreated patient. Treatment can also refer to halting, slowing, or reversing the progression of a disease or condition, compared to a similar but untreated patient. Treatment may comprise addressing the root cause of the disease and/or one or more symptoms.

As used herein a "therapeutically effective amount" refers to a dose sufficient to prevent advancement, or to cause regression of a disease or condition, or which is capable of relieving a symptom of a disease or condition, or which is capable of achieving a desired result. A therapeutically effective dose can be measured, for example, as a number of bacteria or number of viable bacteria (e.g., in CFUs) or a mass of bacteria (e.g., in milligrams, grams, or kilograms), or a volume of bacteria (e.g., in $mm^3$).

As used herein, the term "viability" refers to the autotrophic bacteria's, e.g., ammonia oxidizing bacteria's, ability to oxidize ammonia, ammonium, or urea to nitrite at a pre-determined rate. In some embodiments, the rate refers to the conversion of ammonium ions ($NH_4^+$) (e.g., at about 200 mM) to nitrite ($NO_2^-$) at a rate of at least 50, 75, 125, or 150 micromoles $NO_2^-$ per minute, e.g., about 100-150, 75-175, 75-125, 100-125, 125-150, or 125-175 micromoles/minute, e.g., about 125 micromoles $NO_2^-$ per minute.

"Growth media" or "AOB media," as referred to herein comprises the following components of Table 2 or Table 3:

TABLE 2

| | Weight/Volume (in ~1.5 L) | Final Concentration (in ~1.5 L) |
|---|---|---|
| $(NH_4)_2SO_4$ (MW 132.14) | 4.95 g | 50 mM $NH_4^+$ |
| $KH_2PO_4$ (MW 136.1) | 0.616 g | 3.0 mM |
| 1M $MgSO_4$ | 1.137 ml | 0.76 mM |
| 1M $CaCl_2$ | 0.3 ml | 0.2 mM |
| 30 mM $FeCl_3$/50 mM EDTA | 0.5 ml | 10 μM/16.7 μM |
| 50 mM $CuSO_4$ | 30 μl | 1.0 μM |
| Add 1400 ml dd$H_2O$ to flask. Autoclave. Store at room temperature. After autoclaving add: | | |
| Phosphate Buffer | 100 ml | 32 mM $KH_2PO_4$/ 2.7 mM $NaH_2PO_4 \cdot H_2O$ |
| 5% $Na_2CO_3$ | 12 ml | 0.04% |

TABLE 3

| | Batch medium Weight/Volume (1 L) (Final concentration) | Feeding solution Weight/Volume (1 L) (Final concentration) |
|---|---|---|
| $(NH_4)_2SO_4$ (MW 132.14) | 3.3 g (50 mM $NH_4^+$) | 13.2 g (200 mM $NH_4^+$) |
| $KH_2PO_4$ (MW 136.1) | 1.23 g (9.0 mM) | 0.41 g (3.0 mM) |

TABLE 3-continued

| | Batch medium Weight/Volume (1 L) (Final concentration) | Feeding solution Weight/Volume (1 L) (Final concentration) |
|---|---|---|
| 1M MgSO$_4$ | 0.758 ml (0.76 mM) | 0.758 ml (0.76 mM) |
| 1M CaCl$_2$ | 0.2 ml (0.2 mM) | 0.2 ml (0.2 mM) |
| 30 mM FeCl$_3$/ 50 mM EDTA | 0.333 ml (10 μM/16.7 μM) | 0.333 ml (10 μM/16.7 μM) |
| 50 mM CuSO$_4$ | 20 μl (1.0 μM) | 20 μl (1.0 μM) |
| ddH$_2$O | 1000 ml | 1000 ml |

Autoclave each solution and store at room temperature.

In some embodiments, the states most relevant to the present disclosure are the state of growth, e.g., maximal growth, characterized by a pH of at least about 7.6, ammonia, trace minerals, oxygen and carbon dioxide. Another state may be characterized by a pH of about 7.4 or less and characterized by an absence of carbon dioxide. Under low carbon dioxide conditions, ammonia oxidizing bacteria, e.g., *N. eutropha*, continues to oxidize ammonia into nitrite and generates ATP, but lacking carbon dioxide, e.g., lacking sufficient carbon dioxide, to fix and generate protein, it instead generates polyphosphate, which it uses as an energy storage medium. This may allow the ammonia oxidizing bacteria to remain in a "storage state" for a period of time, e.g., a pre-determined period of time, for example, at least 1, 2, 3, 4, 5, 6, 7, days, 1, 2, 3, 4 weeks, 1, 2, 3, 4, 5, 6, 7, 8, 9, 10, 11, 12 months, 1, 2, 3, 4, or 5 years. In some embodiments, the ammonia oxidizing bacteria may remain in a storage state for at least about 6 months to about 1 year.

As used herein, "growth state" refers to autotrophic bacteria, e.g., ammonia oxidizing bacteria, in a state or in an environment, e.g., a media, e.g., a culture media, e.g., a growth media, that may have a pH of at least about 7.6. Levels of at least one of ammonia, ammonium ions, and urea may be between about 1 micromolar and 1000 millimolar. Levels of trace materials are between about 0.01 micromolar iron and 200 micromolar iron. Levels of oxygen are between about 5% and 100% oxygen saturation (e.g., of media). Levels of carbon dioxide are between about 20 ppm and 10% saturation (e.g., of media). In certain aspects, levels of at least one of ammonia, ammonium ions, and urea may be between about 10 micromolar and 100 millimolar. Levels of trace materials are between about 0.1 micromolar iron and 20 micromolar iron. Levels of oxygen are between about 5% and 100% oxygen saturation. Levels of carbon dioxide are between about 200 ppm and 5% saturation (e.g., of media).

As used herein, "polyphosphate loading state" refers to autotrophic bacteria, e.g., ammonia oxidizing bacteria, in a state or in an environment, e.g., a media, e.g., a culture media, e.g., a growth media, that may have a pH of about 7.4, or less. Levels of at least one of ammonia, ammonium ions, and urea are between about 1 micromolar and 2000 millimolar. Levels of trace materials are between 0.01 micromolar iron and 200 micromolar iron. Levels of oxygen are between about 0% and 100% O2 saturation (e.g., of media). Levels of carbon dioxide are between/less than about zero and 400 ppm, and phosphate levels greater than about 1 micromolar. In certain aspects, levels of at least one of ammonia, ammonium ions, and urea are between about 10 micromolar and 200 millimolar. Levels of trace materials are between 0.1 micromolar iron and 20 micromolar iron. Levels of oxygen are between about 5% and 100% O2 saturation. Levels of carbon dioxide are between/less than about zero and 200 ppm, and phosphate levels greater than about 10 micromolar.

The polyphosphate loading state may be induced for a period of time, e.g., a pre-determined period of time. The pre-determined period of time may the time period that allows sufficient polyphosphate accumulation in the ammonia oxidizing bacteria. This pre-determined period of time is the period of time suitable to provide for sufficient polyphosphate loading to allow for the ammonia oxidizing bacteria to be stored for an extended period of time. The pre-determined period of time may be at least partially based on a period of time of about 0.2-10 times, 0.3-5 times, 0.5-3 times, 0.5-1.5 times, or 0.5 to 1 times the doubling time for the ammonia oxidizing bacteria. The pre-determined period of time may be at least partially based on a period of time of about one doubling time for the ammonia oxidizing bacteria. In some embodiments, the pre-determined period of time is between about 8 hours and 12 hours. In some embodiments, the pre-determined period of time is about 10 hours. In some embodiments, the pre-determined period of time is about 24 hours.

A purpose of the polyphosphate loading state may be to provide AOB with sufficient ammonia, ammonium ions, and/or urea, and O$_2$ such that ATP can be produced, but to deny them CO$_2$ and carbonate such that they are unable to use that ATP to fix CO$_2$ and instead use that ATP to generate polyphosphate which may be stored by the bacteria.

As used herein, the term "storage state" refers to autotrophic bacteria, e.g., ammonia oxidizing bacteria, in a state or in an environment, e.g., a media, e.g., a culture media, e.g., a growth media, having a pH of about 7.4 or less (in some embodiments, the pH may be 7.6 or less). Levels of at least one of ammonia, ammonium ions, and urea are between about 1 and 1000 micromolar. Levels of trace materials are between about 0.1 and 100 micromolar. Levels of oxygen are between about 0 and 100% saturation (e.g., of media). Levels of carbon dioxide are between about 0 and 800 ppm. In certain aspects, levels of at least one of ammonia, ammonium ions, and urea are between about 10 and 100 micromolar. Levels of trace materials are between about 1 and 10 micromolar. Levels of oxygen are between about 0 and 100% saturation (e.g., of media). Levels of carbon dioxide are between about 0 and 400 ppm.

AOB are produced according to some embodiments of the present disclosure by generating AOB biomass during a growth state, then exposing the AOB to a polyphosphate loading state and then removing the media and resuspending the AOB in a buffer, e.g., a storage buffer (i.e., the storage state).

The ammonia oxidizing bacteria may remain in a "storage state" for a period of time, e.g., a pre-determined period of time, for example, at least 1, 2, 3, 4, 5, 6, 7, days, 1, 2, 3, 4 weeks, 1, 2, 3, 4, 5, 6, 7, 8, 9, 10, 11, 12 months, 1, 2, 3, 4, or 5 years. In some embodiments, the ammonia oxidizing bacteria may remain in a storage state for at least about 6 months to about 1 year. Upon revival, the viability of the ammonia oxidizing bacteria is at least about 50%, 60%, 70%, 80%, 90%, or 100% of the viability as of the ammonia oxidizing bacteria prior to storage e.g., in a growth state). In some embodiments, the preparation of ammonia oxidizing bacteria may be prepared, such that no more than 10%, 20%, 30%, 40%, 50%, 60%, or 70% of the ability to oxidize NH$_4^+$ is lost upon storage at selected conditions.

The time that it takes to revive the ammonia oxidizing bacteria from a storage state (or a polyphosphate loading state) may be a pre-determined period of time. For example, the pre-determined period of time may be less than about 75 hours, or less than about 72 hours. The pre-determined period of time may at least partially based on a period time of about 0.2-10 times, 0.3-5 times, 0.5-3 times, 0.5-1.5 times, or 0.5 to 1 times the doubling time for the ammonia oxidizing bacteria. The pre-determined period of time may be at least partially based on a period of time of about one doubling time for the ammonia oxidizing bacteria. The pre-determined period of time may be between about 8 hours and 12 hours. The pre-determined period of time may be about 10 hours. The pre-determined time may be less than about 75 hours, 72 hours, 70 hours, 68 hours, 65 hours, 60 hours, 55 hours, 50 hours, 45 hours, 40 hours, 35 hours, 30 hours, 25 hours, 20 hours, 15 hours, 10 hours, 5 hours, 4 hours, 3, hours, 2 hours, or 1 hour. The pre-determined period of time may be between about 5 minutes and 5 hours. The pre-determined period of time may be about 5-10 minutes, 10-15 minutes, 15-20 minutes, 20-25 minutes, 25-30 minutes, 30-45 minutes, 45-60 minutes, 60 minutes-1.5 hours, 1.5 hours-2 hours, 2 hours-2.5 hours, 2.5 hours-3 hours, 3 hours-3.5 hours, 3.5 hours-4 hours, 4 hours-4.5 hours, 4.5 hours-5 hours. In some embodiments, the pre-determined period of time may be about 2 hours. The pre-determined period of time, e.g., may be the time it may take to achieve revival of the ammonia oxidizing bacteria, e.g., achieve viability of the ammonia oxidizing bacteria as compared to the viability of the bacteria prior to storage (e.g., in a growth state), e.g., at least about 10%, 20%, 30%, 40%, 50%, 60%, 70%, 80%, 90%, 95%, 97%, 98%, 99%, or 100% viability.

"Activation," as used herein, is used relative to autotrophic bacteria, e.g., ammonia oxidizing bacteria. Activation refers to any action that may place the ammonia oxidizing bacteria in a potentially more active state, e.g., a growth state. Activation may relate to stimulation of autotrophic bacteria, e.g., ammonia oxidizing bacteria, to assist in some way in the conversion of at least one of ammonia, ammonium ions, and urea into nitrite, nitric oxide, or nitric oxide precursors. Activation may relate to helping establish a bacterial colony, e.g., to allow for the autotrophic bacteria, e.g., ammonia oxidizing bacteria, to compete with other existing bacteria. Activation may relate to providing an environment that may favor sustainability and/or growth of autotrophic bacteria, e.g., ammonia oxidizing bacteria. Activation may relate to accelerating availability of the autotrophic bacteria, e.g., ammonia oxidizing bacteria to an environment or a surface. "Activation" may provide for ammonia oxidizing bacteria to be in an "activated" or "growth state." "Activation" may take place with the use of an activator. The ammonia oxidizing bacteria may come into contact with the activator to provide an ammonia oxidizing bacteria in an "activated" or "growth" state. This may occur within or outside of a container, delivery device, or delivery system, e.g., within a first chamber, a second chamber, a mixing chamber, a third or additional chamber, or combinations thereof. The activator may be at least one of ammonia, ammonium ions, or urea. The activator may be an ammonium salt, e.g., ammonium chloride or ammonium sulfate. The concentration of the activator, e.g., ammonium salt, e.g., ammonium chloride or ammonium sulfate may be in a range of about 10 micromolar to about 100 millimolar. In certain aspects the concentration of the activator, e.g., ammonium salt, e.g., ammonium chloride or ammonium sulfate may be in a range of about 0.5 mM to about 50 mM. The activator may be in a solution, suspension, a powder, e.g., crystalline form, a media, a buffer, or disposed in or provide as a suitable carrier for maintaining the activator. The ammonia oxidizing bacteria may be in any suitable form for maintaining the AOB in a desired state, e.g., a storage state, e.g., an aqueous suspension, gel, or powder form. The at least one of ammonia, ammonium ions, or urea may be in a medium or a buffer to promote growth of ammonia oxidizing bacteria, e.g., an AOB media or a growth media. A time-release, or controlled release urea may be used as an activator.

"Actuation," as used herein, means that some action is being taken, e.g., a process is being started or something is being put into motion. In some embodiments, actuation may refer to the breaking of a barrier of a container, or the initiation of movement of one or more contents of a container, e.g., delivery of one or more contents of the container to outside of the container, e.g., to a surface or an environment.

A "barrier," as used herein, may mean any structure or configuration that may serve to obstruct passage or to maintain separation, e.g., between a first chamber and a second chamber of a container. The barrier may be in the form of a valve, e.g., a check valve, filtering material, film, wax, lipid, polymer, or controlled release material, e.g., slow release material. The barrier may be a material that upon actuation of a container, it may allow passage of contents from a first chamber into a second chamber, passage of contents from a second chamber into a first chamber, or both. The barrier may be disrupted upon actuation, e.g., through piercing, puncturing, stabbing, perforating, penetrating, splitting, opening or tearing the barrier. The barrier may be in a form of a valve, e.g., a check valve, a flexible or inflexible material that may not degrade upon contact with one or more contents of the container, or a flexible or inflexible material that may degrade upon contact with one or more contents of the container, a filter material. The barrier may be made of any material suitable for its purpose, e.g., a material that may serve to obstruct passage or to maintain separation, e.g., a polymeric material or metal material.

"Microbiome" refers to a population, e.g, one or more microorganisms that live on a surface of a subject, e.g., in the gut, mouth, skin, and/or elsewhere in a subject. The population may have one or more beneficial functions and/or benefits, relevant to supporting the life of a subject.

"Biome-friendly" refers to something, e.g, a product, e.g., a cosmetic product, e.g., a finished cosmetic product that may allow for minimal disruption of a microbiome of a subject. For example, biome-friendly refers to a product that may be applied to a subject that may allow the microbiome at the point of application to be maintained, minimally disrupted, and/or able to return to the microbiome after a period of time after application of the product. In embodiments, biome-friendly may refer to ammonia oxidizing bacteria-friendly, in that the product may allow for minimal disruption of the ammonia oxidizing bacteria of a subject.

In embodiments, "biome-friendly" may be referred to as "biome-compatible."

A "natural product" is or may comprise a product that may be at least partially derived from nature. It may be anything or comprise anything produced by a living organism, and may include organisms themselves. Natural products may include or comprise an entire organism, and part of an organism (e.g., a leaf of a plant), an extract from an organism, an organic compound from an organism, a purified organic compound from an organism. Natural products may be or comprise organic substances found and cells, including primary metabolites (amino acids, carbohydrates, and nucleic acids) and secondary metabolites (organic compounds found in a limited range of species, e.g., polyketides, fatty acids, terpenoids, steroids, phenylpropanoids, alkaloids, specialized amino acids and peptides, specialized carbohydrates). Natural products may be or comprise polymeric organic materials such as cellulose, lignin, and proteins.

Natural products may be or comprise products for commercial purposes, and may refer to cosmetics, dietary supplements, and foods produced from natural sources. Natural products may have pharmacological or biological activity that may be of therapeutic benefit, e.g., in treating disease or conditions. Natural products may be included in traditional medicines, treatments for cosmetological purposes, and spa treatments. A natural product referred to herein may comprise any one or more of the components described as a natural product to be incorporated into a preparation or formulation comprising one or more other components, e.g., excipients. The preparation or formulation referred to as a natural product may comprise a natural product defined herein and one or more additional components or ingredients. Any of the compositions, preparations, or formulations discussed throughout this disclosure may be or comprise one or more natural products.

In some embodiments, the natural product or the fortified natural product may comprise at least one of mud, water, food-derived products, plant-derived products, extracts, and oils. The natural product or the fortified natural product may be used in a spa treatment.

In some embodiments, the natural product or the fortified natural product may be incorporated into at least one of a powder, cream, lotion, wrap, scrub, eye mask, facial mask, body mask, aerosol, e.g., mist, spray, salve, wipe, stick, bandage, or soak.

In some embodiments, the natural product or fortified natural product may be provided as, or may be disposed in at least one of a baby product, e.g., a baby shampoo, a baby lotion, a baby oil, a baby powder, a baby cream; a bath preparation, e.g., a bath oil, a tablet, a salt, a bubble bath, a bath capsule; an eye makeup preparation, e.g., an eyebrow pencil, an eyeliner, an eye shadow, an eye lotion, an eye makeup remover, a mascara; a fragrance preparation, e.g., a colognes, a toilet water, a perfume, a powder (dusting and talcum), a sachet; hair preparations, e.g., hair conditioners, hair sprays, hair straighteners, permanent waves, rinses, shampoos, tonics, dressings, hair grooming aids, wave sets; hair coloring preparations, e.g., hair dyes and colors, hair tints, coloring hair rinses, coloring hair shampoos, hair lighteners with color, hair bleaches; makeup preparations, e.g., face powders, foundations, leg and body paints, lipstick, makeup bases, rouges, makeup fixatives; manicuring preparations, e.g., basecoats and undercoats, cuticle softeners, nail creams and lotions, nail extenders, nail polish and enamel, nail polish and enamel removers; oral hygiene products, e.g., dentrifices, mouthwashes and breath fresheners; bath soaps and detergents, deodorants, douches, feminine hygiene deodorants; shaving preparations, e.g., aftershave lotions, beard softeners, talcum, preshave lotions, shaving cream, shaving soap; skin care preparations, e.g., cleansing, depilatories, face and neck, body and hand, foot powders and sprays, moisturizing, night preparations, paste masks, skin fresheners; and suntan preparations, e.g., gels, creams, and liquids, and indoor tanning preparations.

As used herein, "presence" or "level" may refer to a qualitative or quantitative amount of a component, e.g., any one or more of an ammonia oxidizing bacteria, ammonia, ammonium ions, urea, nitrite, or nitric oxide. The presence or level may include a zero value or a lack of presence of a component.

As used herein, the term "surfactant", includes compounds that may lower the surface tension, or interfacial tension, between two liquids or between a liquid and a solid. Surfactants may act as detergents, wetting agents, emulsifiers, foaming agents, and dispersants. Surfactants may include one or more of the following, alone, or in combination with those listed, or other surfactants or surfactant-like compounds: cocamidopropyl betaine (ColaTeric COAB), polyethylene sorbitol ester (e.g., Tween 80), ethoxylated lauryl alcohol (RhodaSurf 6 NAT), sodium laureth sulfate/lauryl glucoside/cocamidopropyl betaine (Plantapon 611 L UP), sodium laureth sulfate (e.g., Rhoda-Pex ESB 70 NAT), alkyl polyglucoside (e.g., Plantaren 2000 N UP), sodium laureth sulfate (Plantaren 200), Dr. Bronner's Castile soap, Dr. Bronner's baby soap, Lauramine oxide (ColaLux Lo), sodium dodecyl sulfate (SDS), polysulfonate alkyl polyglucoside (PolySufanate 160 P), sodium lauryl sulfate (Stepanol-WA Extra K). and combinations thereof. Dr. Bronner's Castile soap and baby soap comprises water, organic coconut oil, potassium hydroxide, organic olive oil, organic fair deal hemp oil, organic jojoba oil, citric acid, and tocopherol.

Surfactants may include Sodium Laurylglucosides Hydroxypropylsulfonate (Suga® nate 160NC), lauramidopropyl betaine (Cola® Teric LMB); Cocamidopropyl hydroxysultaine (Cola® Teric CBS); disodium cocoamphodiacetate (Cola® Teric CDCX-LV); sodium laurylglucosides hydroxypropyl phosphate (Suga® Fax D12).

Surfactants may include sodium lauroyl methyl isethionate (Iselux® LQ-CLR-SB); sodium methyl cocoyl taurate (Pureact WS Conc.); Aqua (and) Sodium Lauroyl Methyl Isethionate (and) Cocamidopropyl Betaine (and) Sodium Cocoyl Isethionate (and) Sodium Methyl Oleoyl Taurate (Iselux® SFS-SB).

Other surfactants are contemplated by this disclosure.

2. Ammonia Oxidizing Bacteria (AOBs), *N. eutropha* Strain D23 and Other Ammonia Oxidizing Bacteria Autotrophic ammonia oxidizing bacteria, which may be referred to herein as AOBs or AOB, are obligate autotrophic bacteria as noted by Alan B. Hooper and A. Krummel at al. Alan B. Hooper, Biochemical Basis of Obligate Autotrophy in *Nitrosomonas europaea*, Journal of Bacteriology, February 1969, p. 776-779. Antje Krummel et al., Effect of Organic Matter on Growth and Cell Yield of Ammonia-Oxidizing Bacteria, Arch Microbiol (1982) 133: 50-54. These bacteria derive all metabolic energy only from the oxidation of ammonia to nitrite with nitric oxide (NO) as an intermediate product in their respiration chain and derive virtually all carbon by fixing carbon dioxide. They are incapable of utilizing carbon sources other than a few simple molecules.

Ammonia oxidizing bacteria (AOB) are widely found in the environment, and in the presence of ammonia, oxygen and trace metals will fix carbon dioxide and proliferate. AOB may be slow growing and toxic levels of ammonia may kill fish and other organisms before AOB can proliferate and reduce ammonia to non-toxic levels. Slow growth of AOB also may delay the health benefits of the NO and nitrite the AOB produce when applied to the skin.

Supplementing the aquarium, skin, or process with sufficient viable AOB grown and stored for that purpose is desired. AOB do not form spores, so storage in the dry state with high viability is difficult, and storage in the wet state leaves them metabolically active.

Decay of nitrifying capacity during storage of AOB for wastewater treatment has been studied, as for example (Munz G, Lubello C, Oleszkiewicz J A. Modeling the decay of ammonium oxidizing bacteria. Water Res. 2011 January; 45(2): 557-64. Oi: 10.1016/j.watres.2010.09.022.)

Growth, prolonged storage, and restoration of activity of *Nitrosomonas* is discussed by Cassidy et al. (U.S. Pat. No. 5,314,542) where they disclose growing *Nitrosomonas*, removing toxic waste products, storing in sterile water of appropriate salinity for periods of time up to one year, and then reviving by adding buffer ($CaCO_3$) and 200 ppm, of ammonium, which reviving takes 72 hours.

As obligate autotrophs, AOB synthesize protein via the fixing of $CO_2$ using the energy and reducing equivalents generated by the oxidation of ammonia to nitrite. Growth requires ammonia, oxygen, minerals and carbon dioxide.

*Nitrosomonas* may exist in several metabolic states, according to "Polyphosphate and Orthophosphate Content of *Nitrosomonas europaea* as a Function of Growth" by K. R. Terry and A. B. Hooper, Journal of Bacteriology, July 1970, p. 199-206, Vol. 103, No. I.

The AOBs contemplated in this disclosure may comprise mutations relative to wild-type AOBs. These mutations may, e.g., occur spontaneously, be introduced by random mutagenesis, or be introduced by targeted mutagenesis. For instance, the AOBs may lack one or more genes or regulatory DNA sequences that wild-type AOBs typically comprise. The AOBs may also comprise point mutations, substitutions, insertions, deletions, and/or rearrangements relative to the sequenced strain or a wild-type strain. The AOBs may be a purified preparation of optimized AOBs.

In certain embodiments, the AOBs are transgenic. For instance, it may comprise one or more genes or regulatory DNA sequences that wild-type ammonia oxidizing bacteria lacks. More particularly, the ammonia oxidizing bacteria may comprise, for instance, a reporter gene, a selective marker, a gene encoding an enzyme, or a promoter (including an inducible or repressible promoter). In some embodiments the additional gene or regulatory DNA sequence is integrated into the bacterial chromosome; in some embodiments the additional gene or regulatory DNA sequence is situated on a plasmid.

In some embodiments, the AOBs differ by at least one nucleotide from naturally occurring bacteria. For instance, the AOBs may differ from naturally occurring bacteria in a gene or protein that is part of a relevant pathway, e.g., an ammonia metabolism pathway, a urea metabolism pathway, or a pathway for producing nitric oxide or nitric oxide precursors. More particularly, the AOBs may comprise a mutation that elevates activity of the pathway, e.g., by increasing levels or activity of an element of that pathway.

The above-mentioned mutations can be introduced using any suitable technique. Numerous methods are known for introducing mutations into a given position. For instance, one could use site-directed mutagenesis, oligonucleotide-directed mutagenesis, or site-specific mutagenesis. Non-limiting examples of specific mutagenesis protocols are described in, e.g., Mutagenesis, pp. 13.1-13.105 (Sambrook and Russell, eds., Molecular Cloning A Laboratory Manual, Vol. 3, 3.sup.rd ed. 2001). In addition, non-limiting examples of well-characterized mutagenesis protocols available from commercial vendors include, without limitation, Altered Sites® II in vitro Mutagenesis Systems (Promega Corp., Madison, Wis.); Erase-a-Base® System (Promega, Madison, Wis.); GeneTailor™ Site-Directed Mutagenesis System (Invitrogen, Inc., Carlsbad, Calif.); QuikChange® II Site-Directed Mutagenesis Kits (Stratagene, La Jolla, Calif.); and Transformer™ Site-Directed Mutagenesis Kit (BD-Clontech, Mountain View, Calif.).

In certain embodiments of the disclosure, the ammonia oxidizing bacteria may be axenic. The preparation (formulation or composition) of ammonia oxidizing bacteria may comprise, consist essentially of, or consist of axenic ammonia oxidizing bacteria.

The ammonia oxidizing bacteria of this disclosure may be from a genus selected from the group consisting of *Nitrosomonas, Nitrosococcus, Nitrosospria, Nitrosocystis, Nitrosolobus, Nitrosovibrio*, and combinations thereof.

This disclosure provides, inter alia, *N. eutropha* strain D23, a unique, e.g., optimized strain of ammonia oxidizing bacteria that can increase production of nitric oxide and nitric oxide precursors on the surface of a subject, e.g., a human subject. This disclosure also provides methods of using the bacteria and articles comprising the bacteria.

In embodiments, the ammonia oxidizing bacteria, e.g., *N. eutropha* is non-naturally occurring. For instance, it may have accumulated desirable mutations during a period of selection. In other embodiments, desirable mutations may be introduced by an experimenter. In some embodiments, the *N. eutropha* may be a purified preparation, and may be an optimized *N. eutropha*.

In preferred embodiments, the *N. eutropha* strain is autotrophic and so incapable of causing infection. A preferred strain utilizes urea as well as ammonia, so that hydrolysis of the urea in sweat would not be necessary prior to absorption and utilization by the bacteria. Also, in order to grow at low pH, the bacteria may either absorb $NH_4^+$ ions or urea. The selected strain should also be capable of living on the external skin of a subject, e.g., a human, and be tolerant of conditions there.

Although this disclosure refers to *N. eutropha* strain D23 in detail, the preparations, methods, compositions, treatments, wearable articles, and articles of clothing may be used with one or more of: one or more other strains of *N. eutropha*, one or more other species of *Nitrosomonas*, and one or more other ammonia oxidizing bacteria.

In certain embodiments, the *N. eutropha* is the strain deposited with the American Tissue Culture Collection (ATCC) on Apr. 8, 2014, designated AOB D23-100 (25 vials) under accession number PTA-121157. D23 *Nitrosomonas eutropha* strain refers to the strain, designated AOB D23-100, deposited with the American Tissue Culture Collection (ATCC) (10801 University Blvd., Manassas, Va., USA) on Apr. 8, 2014 having accession number PTA-121157. The nucleic acid sequence(s), e.g., genome sequence, of accession number PTA-121157 are hereby incorporated by reference in their entireties. In certain embodiments, the *N. eutropha* is a strain described in PCT Application No. PCT/US2015/025909, filed Apr. 15, 2015, herein incorporated by reference in its entirety.

In certain embodiments, a bacterium with the above-mentioned sequence characteristics has one or more of (1) an optimized growth rate as measured by doubling time, (2) an optimized growth rate as measured by OD600, (3) an optimized $NH_4^+$ oxidation rate, (4) an optimized resistance to $NH_4^+$, and (4) an optimized resistance to $NO_2^-$. Particular sub-combinations of these properties are specified in the following paragraph.

In some embodiments, the ammonia oxidizing bacteria, e.g., the *N. eutropha* described herein has one or more of: (1) an optimized growth rate as measured by doubling time, (2) an optimized growth rate as measured by OD600, (3) an optimized $NH_4^+$ oxidation rate, (4) an optimized resistance to, $NH_4^+$, and (4) an optimized resistance to, $NO_2^-$. For instance, the bacterium may have properties (1) and (2); (2) and (3); (3) and (4); or (4) and (5) from the list at the beginning of this paragraph. As another example, the bacterium may have properties (1), (2), and (3); (1), (2), and (4);

(1), (2), and (5); (1), (3), and (4); (1), (3), and (5); (1), (4), and (5); (2), (3), and (4); (2), (3), and (5), or (3), (4), and (5) from the list at the beginning of this paragraph. As a further example, the bacterium may have properties (1), (2), (3), and (4); (1), (2), (3), and (5); (1), (2), (4), and (5); (1), (3), (4), and (5); or (2), (3), (4), and (5) from the list at the beginning of this paragraph. In some embodiments, the bacterium has properties (1), (2), (3), (4), and (5) from the list at the beginning of this paragraph.

This disclosure also provides an axenic composition of ammonia oxidizing bacteria, e.g., N. eutropha having one or more of: (1) an optimized growth rate as measured by doubling time, (2) an optimized growth rate as measured by OD600, (3) an optimized $NH_4^+$ oxidation rate, (4) an optimized resistance to, $NH_4^+$, and (4) an optimized resistance to, $NO_2^-$. For instance, the bacterium composition may have properties (1) and (2); (2) and (3); (3) and (4); or (4) and (5) from the list at the beginning of this paragraph. As another example, the bacterium composition may have properties (1), (2), and (3); (1), (2), and (4); (1), (2), and (5); (1), (3), and (4); (1), (3), and (5); (1), (4), and (5); (2), (3), and (4); (2), (3), and (5), or (3), (4), and (5) from the list at the beginning of this paragraph. As a further example, the bacterium composition may have properties (1), (2), (3), and (4); (1), (2), (3), and (5); (1), (2), (4), and (5); (1), (3), (4), and (5); or (2), (3), (4), and (5) from the list at the beginning of this paragraph. In some embodiments, the bacterium composition has properties (1), (2), (3), (4), and (5) from the list at the beginning of this paragraph.

N. eutropha strain D23, as deposited in the form of 25 vials on Apr. 8, 2014, in the ATCC patent depository, designated AOB D23-100, under accession number PTA-121157, comprises a circular genome having SEQ ID NO: 1 or its complement. Accordingly, in some embodiments, an N. eutropha strain described herein comprises a nucleic acid sequence, e.g., a genome, that is similar to SEQ ID NO: 1, or its complement, of PCT Application No. PCT/US2015/025909, filed Apr. 15, 2015.

In certain embodiments, the N. eutropha strain comprises a nucleic acid sequence, e.g., a genome, that hybridizes to SEQ ID NO: 1, of PCT Application No. PCT/US2015/025909, filed Apr. 15, 2015, or to the genome of the D23 strain deposited in the form of 25 vials with the ATCC patent depository on Apr. 8, 2014, designated AOB D23-100, under accession number PTA-121157, or their complements, under low stringency, medium stringency, high stringency, or very high stringency, or other hybridization condition described herein.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; 4) very high stringency hybridization conditions are 0.5M sodium phosphate, 7% SDS at 65° C., followed by one or more washes at 0.2×SSC, 1% SDS at 65° C. Very high stringency conditions (4) are suitable conditions and the ones that should be used unless otherwise specified.

The D23 strain is not believed to be a product of nature, but rather has acquired certain mutations and characteristics during an extended period of culture and selection in the laboratory. For instance, D23 has an ability to grow in conditions of greater than about 200 or 250 mM $NH_4^+$ for more than 24 hours.

In some embodiments, the N. eutropha disclosed herein differ from naturally occurring bacteria in the abundance of siderophores. For instance, the N. eutropha may have elevated or reduced levels of siderophores compared to N. eutropha C91. Generally, siderophores are secreted iron-chelating compounds that help bacteria scavenge iron from their environment. Some siderophores are peptides, and others are small organic molecules.

The AOBs, for example, N. eutropha contemplated in this disclosure may comprise mutations relative to wild-type N. eutropha and/or the N. eutropha sequences disclosed herein. These mutations may, e.g., occur spontaneously, be introduced by random mutagenesis, or be introduced by targeted mutagenesis. For instance, the ammonia oxidizing bacteria, e.g., N. eutropha may lack one or more genes or regulatory DNA sequences that wild-type N. eutropha typically comprises. The ammonia oxidizing bacteria, e.g., N. eutropha may also comprise point mutations, substitutions, insertions, deletions, and/or rearrangements relative to the sequenced strain or a wild-type strain. The ammonia oxidizing bacteria, e.g., N. eutropha may be a purified preparation of optimized ammonia oxidizing bacteria, e.g., N. eutropha.

In certain embodiments, the ammonia oxidizing bacteria, e.g., N. eutropha is transgenic. For instance, it may comprise one or more genes or regulatory DNA sequences that wild-type N. eutropha D23 lacks. More particularly, the ammonia oxidizing bacteria, e.g., N. eutropha may comprise, for instance, a reporter gene, a selective marker, a gene encoding an enzyme, or a promoter (including an inducible or repressible promoter). In some embodiments the additional gene or regulatory DNA sequence is integrated into the bacterial chromosome; in some embodiments the additional gene or regulatory DNA sequence is situated on a plasmid, for instance a plasmid related to a plasmid found in N. eutropha N91.

In some preferred embodiments, the ammonia oxidizing bacteria, e.g., N. eutropha differs by at least one nucleotide from naturally occurring bacteria. For instance, the ammonia oxidizing bacteria, e.g., N. eutropha may differ from naturally occurring bacteria in a gene or protein that is part of a relevant pathway, e.g., an ammonia metabolism pathway, a urea metabolism pathway, or a pathway for producing nitric oxide or nitric oxide precursors. More particularly, the ammonia oxidizing bacteria, e.g., N. eutropha may comprise a mutation that elevates activity of the pathway, e.g., by increasing levels or activity of an element of that pathway.

The above-mentioned mutations can be introduced using any suitable technique. Numerous methods are known for introducing mutations into a given position. For instance, one could use site-directed mutagenesis, oligonucleotide-directed mutagenesis, or site-specific mutagenesis. Non-limiting examples of specific mutagenesis protocols are described in, e.g., Mutagenesis, pp. 13.1-13.105 (Sambrook and Russell, eds., Molecular Cloning A Laboratory Manual, Vol. 3, 3.sup.rd ed. 2001). In addition, non-limiting examples of well-characterized mutagenesis protocols available from commercial vendors include, without limitation, Altered Sites® II in vitro Mutagenesis Systems (Promega Corp., Madison, Wis.); Erase-a-Base.RTM. System (Promega, Madison, Wis.); GeneTailor.TM. Site-Directed Mutagenesis System (Invitrogen, Inc., Carlsbad, Calif.); QuikChange® II Site-Directed Mutagenesis Kits (Stratagene, La Jolla, Calif.); and Transformer™ Site-Directed Mutagenesis Kit (BD-Clontech, Mountain View, Calif.).

In some embodiments, the preparation of ammonia oxidizing bacteria may comprise a concentration or amount of ammonia oxidizing bacteria in order to at least partially treat a condition or disease. The preparation of ammonia oxidizing bacteria may comprise a concentration or amount of ammonia oxidizing bacteria in order to alter, e.g., reduce or increase, an amount, concentration or proportion of a bacterium, or genus of bacteria, on a surface, e.g., a skin surface. The bacteria may be non-pathogenic or pathogenic, or potentially pathogenic.

In some embodiments, the preparation of ammonia oxidizing bacteria may comprise between about $10^8$ to about $10^{14}$ CFU/L. The preparation may comprise at least $10^8$, $10^9$, $10^{10}$, $10^{11}$, $2 \times 10^{11}$, $5 \times 10^{11}$, $10^{12}$, $2 \times 10^{12}$, $5 \times 10^{12}$, $10^{13}$, $2 \times 10^{13}$, $5 \times 10^{13}$, or $10^{14}$; or about $10^8$-$10^9$, $10^9$-$10^{10}$, $10^{11}$-$10^{11}$, $10^{11}$-$10^{12}$, $10^{12}$-$10^{13}$, or $10^{13}$-$10^{14}$ CFU/L.

In certain aspects, the preparation may comprise between about $1 \times 10^9$ CFU/L to about $10 \times 10^9$ CFU/L. In certain aspects, the preparation may comprise between about $1 \times 10^9$ CFU to about $10 \times 10^9$ CFU. In certain aspects, the preparation may comprise about $1 \times 10^9$ CFU/mL to $10 \times 10^9$ CFU/mL. In certain aspects, the preparation may comprise about $1 \times 10^9$ CFU/mL.

In some embodiments, the preparation of ammonia oxidizing bacteria may comprise between about 0.1 milligrams (mg) and about 1000 mg of ammonia oxidizing bacteria. In certain aspects, the preparation may comprise between about 50 mg and about 1000 mg of ammonia oxidizing bacteria. The preparation may comprise between about 0.1-0.5 mg, 0.2-0.7 mg, 0.5-1.0 mg, 0.5-2 mg, 0.5-5 mg, 2.5-5 mg, 2.5-7.0 mg, 5.0-10 mg, 7.5-15 mg, 10-15 mg, 15-20 mg, 15-25 mg, 20-30 mg, 25-50 mg, 25-75 mg, 50-75 mg, 50-100 mg, 75-100 mg, 100-200 mg, 200-300 mg, 300-400 mg, 400-500 mg, 500-600 mg, 600-700 mg, 700-800 mg, 800-900 mg, 900-1000 mg, 100-250 mg, 250-500 mg, 100-500 mg, 500-750 mg, 750-1000 mg, or 500-1000 mg.

In some embodiments, the preparation of ammonia oxidizing bacteria may comprise a mass ratio of ammonia oxidizing bacteria to an excipient, e.g., a pharmaceutically acceptable excipient or a cosmetically acceptable excipient in a range of about 0.1 grams per liter to about 1 gram per liter. The preparation may comprise a mass ratio of ammonia oxidizing bacteria to an excipient in a range of about 0.1-0.2, 0.2-0.3, 0.1-0.5, 0.2-0.7, 0.5-1.0, or 0.7-1.0 grams per liter.

In some embodiments, the preparation of ammonia oxidizing bacteria may comprise an ammonia oxidizing bacteria having a dose as described herein, in combination with ammonia, for example, an ammonia concentration of between about 0.01 mM to about 100 mM. For example, the ammonia concentration may be about 0.01, 0.05, 0.1, 0.2, 0.4, 0.5, 0.6, 0.8, 1.0, 1.2, 1.4, 1.6, 1.8, 2.0, 2.2, 2.4, 2.5, 2.6, 2.8, 3.0, 3.2, 3.4, 3.6, 3.8, 4.0, 4.2, 4.4, 4.5, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 10.0, 15.0, 20.0, 25.0, 30.0, 35.0, 40.0, 45.0, 50.0, 55.0, 60.0, 65.0, 70.0, 75.0, 80.0, 85.0, 90.0, 95.0, 100.0 mM. In some embodiments, the preparation of ammonia oxidizing bacteria may comprise, consist essentially of, or consist of ammonia oxidizing bacteria in an aqueous buffer solution comprising, consisting essentially of, or consisting of disodium phosphate and magnesium chloride, for example, 50 mM $Na_2HPO_4$ and 2 mM $MgCl_2$. In certain aspects, the preparation may comprise about $1 \times 10^9$ CFU/mL, 50 mM $Na_2HPO_4$, and 2 mM $MgCl_2$, in water.

In some embodiments, the preparation of ammonia oxidizing bacteria may comprise components that provide for pre-activation of the ammonia oxidizing bacteria. For example, pre-activation may involve having a preparation having ammonia oxidizing bacteria and ammonia.

In some embodiments, the preparation of ammonia oxidizing bacteria may be in a form that provides for activation upon delivery to a subject, e.g., coactivation. This would provide for delivery of ammonia oxidizing bacteria to an utilizing ammonia present on the subject prior to or simultaneously with delivery of the ammonia oxidizing bacteria. For example, the ammonia may be derived from the subject's own source of ammonia, or be applied, prior to or at the same time as the ammonia oxidizing bacteria. The ammonia may be provided in a separate container, or may be naturally derived from the subject.

The preparation may comprise a volume of between about 0.1 and about 100 fluid ounces, about 0.2 and about 50 fluid ounces, about 0.5 and about 25 fluid ounces, about 1.0 and about 10 fluid ounces, about 2.0 and about 7 fluid ounces, about 3 and about 5 fluid ounces. In some embodiments, the preparation may comprise a volume of about 3.4 fluid ounces.

The preparation may be provided in a container constructed to contain between about 0.1 and about 100 fluid ounces, about 0.2 and about 50 fluid ounces, about 0.5 and about 25 fluid ounces, about 1.0 and about 10 fluid ounces, about 2.0 and about 7 fluid ounces, about 3 and about 5 fluid ounces. In some embodiments, the preparation is a container constructed to contain about 3.4 fluid ounces. The container may be a one-chamber container, or any other container disclosed herein.

In some embodiments, the preparation of ammonia oxidizing bacteria may be in a growth state. A growth state may be provided by exposing ammonia oxidizing bacteria to an environment that may promote growth. The growth state may be a state, e.g., ammonia oxidizing bacteria in an environment that allows immediate availability of ammonia oxidizing bacteria to convert ammonium ions ($NH_4^+$) to nitrite ($NO_2^-$). The growth state may comprise providing ammonia oxidizing bacteria in an environment having a pH of greater than about 7.6. The growth state may also comprise providing ammonia oxidizing bacteria in an environment having ammonia, ammonium salts, and/or urea, trace minerals and sufficient oxygen and carbon dioxide, as described above in Section 1.

In some embodiments, the preparation of ammonia oxidizing bacteria may be in a polyphosphate loading state, wherein the state or the environment, e.g., a media, e.g., a culture media, e.g., a growth media, may have a pH of less than about 7.4. Levels of at least one of ammonia, ammonium ions, and urea may be between about 10 micromolar and 200 millimolar. Levels of trace materials may be between 0.1 micromolar iron and 20 micromolar iron. Levels of oxygen may be between about 5% and 100% oxygen saturation. Levels of carbon dioxide may be between/less than about zero and 200 ppm, and phosphate levels greater than about 10 micromolar. The purpose of the polyphosphate loading state is to provide AOB with ammonia and oxygen such that ATP can be produced, but to deny them carbon dioxide and carbonate such that they are unable to use that ATP to fix carbon dioxide and instead use that ATP to generate polyphosphate which may be stored.

In some embodiments, the preparation of ammonia oxidizing bacteria may be in a storage state. A storage state may be defined as ammonia oxidizing bacteria in an environment in which they may be stored to be later revived. The storage state may be a state, e.g., ammonia oxidizing bacteria in an environment that allows availability of ammonia oxidizing bacteria after being revived, e.g., after being place in an environment promoting a growth state for a pre-determined period of time.

The storage state may comprise providing ammonia oxidizing bacteria in an environment having a pH of less than about 7.4. The storage state may also comprise providing ammonia oxidizing bacteria in an environment having ammonia, ammonia salts, and/or urea, trace minerals, oxygen, and low concentrations of carbon dioxide, as described above in Section 1.

Storage may also be accomplished by storing at 4° C. for up to several months. The storage buffer in some embodiments may comprise 50 mM $Na_2HPO_4$-2 mM $MgCl_2$ (pH 7.6).

In some embodiments, ammonia oxidizing bacteria may be cyropreserved. A 1.25 ml of ammonia oxidizing bacteria mid-log culture may be added to a 2 ml cryotube and 0.75 ml of sterile 80% glycerol. Tubes may be shaken gently, and incubate at room temperature for 15 min to enable uptake of the cryoprotective agents by the cells. The tubes may be directly stored in a −80° C. freezer for freezing and storage.

For resuscitation of cultures, frozen stocks may be thawed on ice for 10-20 minutes, and then centrifuged at 8,000×g for 3 minutes at 4° C. The pellet may be washed by suspending it in 2 ml AOB medium followed by another centrifugation at 8,000×g for 3 minutes at 4° C. to reduce potential toxicity of the cryoprotective agents. The pellet may be resuspended in 2 ml of AOB medium, inoculated into 50 ml of AOB medium containing 50 mM $NH_4^+$, and incubated in dark at 30° C. by shaking at 200 rpm.

In some embodiments, the preparation of ammonia oxidizing bacteria may comprise ammonia oxidizing bacteria in a storage state and/or ammonia oxidizing bacteria in a polyphosphate loading state and/or ammonia oxidizing bacteria in a growth state.

Without wishing to be bound by theory, by maintaining ammonia oxidizing bacteria under conditions or in an environment of low carbon dioxide, with sufficient oxygen and ammonia, they may accumulate polyphosphate for a pre-determined period, e.g., for a period of about one doubling time, e.g., for about 8-12 hours, e.g., for about 10 hours. The ammonia oxidizing bacteria may accumulate sufficient polyphosphate to extend their storage viability, storage time, and accelerate their revival. This may occur with or without the addition of buffer and ammonia.

The presence of sufficient stored polyphosphate may allow the ammonia oxidizing bacteria the ATP resources to maintain metabolic activity even in the absence of ammonia and oxygen, and to survive insults that would otherwise be fatal.

The process of oxidation of ammonia to generate ATP has two steps. The first step is the oxidation of ammonia to hydroxylamine by ammonia monoxoygenase (Amo), followed by the conversion of hydroxylamine to nitrite by hydroxylamine oxidoreductase (Hao). Electrons from the second step (conversion of hydroxylamine to nitrite) are used to power the first step (oxidation of ammonia to hydroxylamine).

If an ammonia oxidizing bacteria does not have hydroxylamine to generate electrons for Amo, then hydroxylamine is not available for Hao. For example, acetylene irreversibly inhibits the enzyme crucial for the first step in the oxidation of ammonia to nitrite, the oxidation of ammonia to hydroxylamine. Once AOB are exposed to acetylene, Amo is irreversibly inhibited and new enzyme must be synthesized before hydroxylamine can be generated. In a normal consortium biofilm habitat, AOB may share and receive hydroxylamine form other AOB (even different strains with different susceptibilities to inhibitors) and so the biofilm tends to be more resistant to inhibitors such as acetylene than an individual organism. AOB can use stored polyphosphate to synthesize new Amo, even in the absence of hydroxylamine.

Any embodiment, preparation, composition, or formulation of ammonia oxidizing bacteria discussed herein may comprise, consist essentially of, or consist of optionally axenic ammonia oxidizing bacteria.

3. Compositions Comprising Ammonia Oxidizing Bacteria; Compositions Comprising *N. eutropha*, e.g., D23 *N. eutropha*

The present disclosure provides, inter alia, compositions comprising ammonia oxidizing bacteria, e.g., a preparation of ammonia oxidizing bacteria, or a purified preparation of ammonia oxidizing bacteria e.g., a natural product, or a fortified natural product.

The compositions disclosed herein throughout this disclosure may be provided to be used in treatment of a skin condition, e.g., acne, e.g., acne vulgaris.

The compositions comprising ammonia oxidizing bacteria, e.g., a preparation of ammonia oxidizing bacteria, or a purified preparation of ammonia oxidizing bacteria may be provided in a cosmetic product or a therapeutic product. The preparation may comprise, inter alia, at least one of ammonia, ammonium salts, and urea. The ammonia oxidizing bacteria may be any ammonia oxidizing bacteria, or combination of ammonia oxidizing bacteria, as disclosed herein.

The present disclosure provides, inter alia, compositions comprising *N. eutropha*, e.g., a purified preparation of an optimized *N. eutropha*. In some embodiments, the *N. eutropha* in the compositions has at least one property selected from an optimized growth rate, an optimized $NH_4^+$ oxidation rate, and an optimized resistance to $NH_4^+$.

In some aspects, the present disclosure provides compositions with a defined number of species. For instance, this disclosure provides a composition having *N. eutropha* and one other type of organism, and no other types of organism. In other examples, the composition has *N. eutropha* and 2, 3, 4, 5, 6, 7, 8, 9, or 10 other types of organism, and no other types of organism. The other type of organism in this composition may be, for instance, a bacterium, such as an ammonia-oxidizing bacterium. Suitable ammonia-oxidizing bacteria for this purpose include those in the genera *Nitrosomonas, Nitrosococcus, Nitrosospira, Nitrosocystis, Nitrosolobus*, or *Nitrosovibrio*.

In some embodiments, the composition comprising ammonia oxidizing bacteria, e.g., *N. eutropha* provides conditions that support ammonia oxidizing bacteria, e.g., *N. eutropha* viability. For instance, the composition may promote ammonia oxidizing bacteria, e.g., *N. eutropha* growth and metabolism or may promote a dormant state (e.g., freezing) from which viable ammonia oxidizing bacteria, e.g., *N. eutropha* can be recovered. When the composition promotes growth or metabolism, it may contain water and/or nutrients that ammonia oxidizing bacteria, e.g., *N. eutropha* consumes, e.g., as ammonium, ammonia, urea, oxygen, carbon dioxide, or trace minerals.

In some embodiments, one or more other organisms besides ammonia oxidizing bacteria may be included in the preparation of ammonia oxidizing bacteria. For example, an organism of the genus selected from the group consisting of *Lactobacillus, Streptococcus, Bifidobacter*, and combinations thereof, may be provided in the preparation of ammonia oxidizing bacteria. In some embodiments, the preparation may be substantially free of other organisms.

Preparations of ammonia oxidizing bacteria may comprise between about between about $10^8$ to about $10^{14}$ CFU/L. The preparation may comprise at least about $10^8$, $10^9$, $10^{10}$, $10^{11}$, $2 \times 10^{11}$, $5 \times 10^{11}$, $10^{12}$, $2 \times 10^{12}$, $5 \times 10^{12}$, $10^{13}$, $2 \times 10^{13}$, $5 \times 10^{13}$, or $10^{14}$; or about $10^8$-$10^9$, $10^9$-$10^{10}$, $10^{10}$-$10^{11}$, $10^{11}$-$10^{12}$, $10^{12}$-$10^{13}$, or $10^{13}$-$10^{14}$ CFU/L. Other preparations may comprise about $2 \times 10^9$, $4 \times 10^9$, or $8 \times 10^9$ CFU/L.

Preparations of ammonia oxidizing bacteria may comprise between about between about $10^8$ to about $10^{14}$ CFU/ml. The preparation may comprise at least about $10^8$, $10^9$, $10^{10}$, $10^{11}$, $2 \times 10^{11}$, $5 \times 10^{11}$, $10^{12}$, $2 \times 10^{12}$, $5 \times 10^{12}$, $10^{13}$, $2 \times 10^{13}$, $5 \times 10^{13}$, or $10^{14}$; or about $10^8$-$10^9$, $10^9$-$10^{10}$, $10^{10}$-$10^{11}$, $10^{11}$-$10^{12}$, $10^{12}$-$10^{13}$, or $10^{13}$-$10^{14}$ CFU/ml. Other preparations may comprise about $2 \times 10^9$, $4 \times 10^9$, or $8 \times 10^9$ CFU/mL.

In some embodiments, the preparation may comprise between about $1 \times 10^9$ to about $10 \times 10^9$ CFU/L. In some embodiments, the preparation may comprise about $3 \times 10^{10}$ CFU, e.g., $3 \times 10^{10}$ CFU per day. In some embodiments, the preparation may comprise about $1 \times 10^9$ to about $10 \times 10^9$ CFU, e.g., about $1 \times 10^9$ to about $10 \times 10^9$ CFU per day.

In some embodiments, the preparation of ammonia oxidizing bacteria may comprise between about 0.1 milligrams (mg) and about 1000 mg of ammonia oxidizing bacteria. In certain aspects, the preparation may comprise between about 50 mg and about 1000 mg of ammonia oxidizing bacteria. The preparation may comprise between about 0.1-0.5 mg, 0.2-0.7 mg, 0.5-1.0 mg, 0.5-2 mg, 0.5-5 mg, 2.5-5 mg, 2.5-7.0 mg, 5.0-10 mg, 7.5-15 mg, 10-15 mg, 15-20 mg, 15-25 mg, 20-30 mg, 25-50 mg, 25-75 mg, 50-75 mg, 50-100 mg, 75-100 mg, 100-200 mg, 200-300 mg, 300-400 mg, 400-500 mg, 500-600 mg, 600-700 mg, 700-800 mg, 800-900 mg, 900-1000 mg, 100-250 mg, 250-500 mg, 100-500 mg, 500-750 mg, 750-1000 mg, or 500-1000 mg.

In some embodiments, the preparation of ammonia oxidizing bacteria may comprise a mass ratio of ammonia oxidizing bacteria to an excipient, e.g., a pharmaceutically acceptable excipient or a cosmetically acceptable excipient in a range of about 0.1 grams per liter to about 1 gram per liter. The preparation may comprise a mass ratio of ammonia oxidizing bacteria to an excipient in a range of about 0.1-0.2, 0.2-0.3, 0.1-0.5, 0.2-0.7, 0.5-1.0, or 0.7-1.0 grams per liter.

In some embodiments, the preparation of ammonia oxidizing bacteria may be ammonia oxidizing bacteria in an aqueous buffer solution comprising, consisting essentially of, or consisting of disodium phosphate and magnesium chloride, for example, 50 mM $Na_2HPO_4$ and 2 mM $MgCl_2$. The ammonia oxidizing bacteria may be of any concentration disclosed herein, for example $1 \times 10^9$ CFU/ml. The preparation may be provided in a buffer at a pre-determined volume of, for example, between about 0.1 and about 100 fluid ounces, about 0.2 and about 50 fluid ounces, about 0.5 and about 25 fluid ounces, about 1.0 and about 10 fluid ounces, about 2.0 and about 7 fluid ounces, about 3 and about 5 fluid ounces. In some embodiments, the preparation may be provided in a container. The preparation may be provided in a container constructed to contain about 3.4 fluid ounces, or any other volume disclosed herein. The preparation may be in a form that may be capable of being aerosolized, sprayed or misted, i.e., in the form of a mist, e.g., in an AO+Mist product.

Advantageously, a formulation may have a pH that promotes AOB, e.g., *N. eutropha* viability, e.g., metabolic activity. Urea would hydrolyze to ammonia and would raise the pH to 7 to 8. AOB are very active at this pH range and would lower the pH to about 6 where the NH3 converts to ammonium and is unavailable. Lower pH levels, e.g. about pH 4, are also acceptable.

The ammonia oxidizing bacteria, e.g., *N. eutropha* may be combined with one or more pharmaceutically or cosmetically acceptable excipients. In some embodiments, "pharmaceutically acceptable excipient" refers to a pharmaceutically-acceptable material, composition, or vehicle, such as a liquid or solid filler, diluent, solvent, or encapsulating material. In some embodiments, each excipient is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, Remington: The Science and Practice of Pharmacy, 21st ed.; Lippincott Williams & Wilkins: Philadelphia, Pa., 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, Fla., 2009.

In some embodiments, a cosmetically acceptable excipient refers to a cosmetically acceptable material, composition, or vehicle, such as a liquid or solid filler, diluent, solvent, or encapsulating material. In some embodiments, each excipient is cosmetically acceptable in the sense of being compatible with the other ingredients of a cosmetic formulation, and suitable for use in contact with the tissue or organ of humans and animals without excessive toxicity, irritation, allergic response, immunogenicity, or other problems or complications, commensurate with a reasonable benefit/risk ratio.

While it is possible for the active ingredient, e.g., ammonia oxidizing bacteria, e.g., *N. eutropha*, to be administered alone, in many embodiments it present in a pharmaceutical formulation or composition. Accordingly, this disclosure provides a pharmaceutical formulation (preparation or composition) or a cosmetic formulation (preparation or composition) comprising ammonia oxidizing bacteria and a pharmaceutically acceptable excipient or a cosmetically acceptable excipient. Pharmaceutical compositions and cosmetic compositions may take the form of a formulation as described below.

The pharmaceutical and cosmetic formulations (e.g., preparations or compositions) described herein may include those suitable for oral (e.g., by way of, or for the purposes of depositing in the gastrointestinal tract), parenteral (including subcutaneous, intradermal, intramuscular, intravenous, and intraarticular), inhalation (including fine particle dusts or mists which may be generated by means of various types of metered doses, pressurized aerosols, nebulizers or insufflators, and including intranasally (nasal) or via the lungs (pulmonary)), rectal and topical (including dermal, transdermal, transmucosal, buccal, sublingual, and intraocular) administration, although the most suitable route may depend upon, for example, the condition and disorder of the recipient.

The formulations (e.g., preparations or compositions) may conveniently be presented in unit dosage form and may be prepared by any of the methods known in the art of pharmacy or cosmetology. Typically, methods include the step of bringing the active ingredient (e.g., ammonia oxidizing bacteria, e.g., *N. eutropha*) into association with a pharmaceutical or a comestic carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations may be presented as discrete units such as capsules, cachets or tablets, each containing a predetermined amount of, e.g., *N. eutropha*; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Various pharmaceutically acceptable carriers and their formulation are described in standard formulation treatises, e.g., Remington's Pharmaceutical Sciences by E. W. Martin. See also Wang, Y. J. and Hanson, M. A., Journal of Parenteral Science and Technology, Technical Report No. 10, Supp. 42:2 S, 1988.

The ammonia oxidizing bacteria, e.g., *N. eutropha* compositions can, for example, be administered in a form suitable for immediate release or extended release. Suitable examples of sustained-release systems include suitable polymeric materials, for example semi-permeable polymer matrices in the form of shaped articles, e.g., films, or microcapsules; suitable hydrophobic materials, for example as an emulsion in an acceptable oil; or ion exchange resins. Sustained-release systems may be administered orally; rectally; parenterally; intracisternally; intravaginally; intraperitoneally; topically, for example as a powder, ointment, gel, drop or transdermal patch; bucally; or as a spray.

Preparations for administration can be suitably formulated to give controlled release of ammonia oxidizing bacteria, e.g., *N. eutropha*. For example, the pharmaceutical compositions may be in the form of particles comprising one or more of biodegradable polymers, polysaccharide jellifying and/or bioadhesive polymers, or amphiphilic polymers. These compositions exhibit certain biocompatibility features which allow a controlled release of an active substance. See U.S. Pat. No. 5,700,486.

Exemplary compositions include suspensions which can contain, for example, microcrystalline cellulose for imparting bulk, alginic acid or sodium alginate as a suspending agent, methylcellulose as a viscosity enhancer, dicalcium phosphate, starch, magnesium stearate and/or lactose and/or other excipients, binders, extenders, disintegrants, diluents and lubricants, mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. The surfactant may be a zwitterionic surfactant, a non-ionic surfactant, or an anionic surfactant.

Excipients, such as surfactants that may be used with embodiments of the present disclosure may include one or more of cocamidopropyl betaine (ColaTeric COAB), polyethylene sorbitol ester (e.g., Tween 80), ethoxylated lauryl alcohol (RhodaSurf 6 NAT), sodium laureth sulfate/lauryl glucoside/cocamidopropyl betaine (Plantapon 611 L UP), sodium laureth sulfate (e.g., RhodaPex ESB 70 NAT), alkyl polyglucoside (e.g., Plantaren 2000 N UP), sodium laureth sulfate (Plantaren 200), Dr. Bronner's Castile soap, Dr. Bronner's Castile baby soap, Lauramine oxide (ColaLux Lo), sodium dodecyl sulfate (SDS), polysulfonate alkyl polyglucoside (PolySufanate 160 P), sodium lauryl sulfate (Stepanol-WA Extra K). and combinations thereof. Dr. Bronner's Castile soap and Dr. Bronner's baby soap comprises water, organic coconut oil, potassium hydroxide, organic olive oil, organic fair deal hemp oil, organic jojoba oil, citric acid, and tocopherol.

In some embodiments, surfactants may be used with ammonia oxidizing bacteria in amounts that allow nitrite production to occur. In some embodiments, the preparation may have less than about 0.0001% to about 10% of surfactant. In some embodiments, the preparation may have between about 0.1% and about 10% surfactant. In some embodiments, the concentration of surfactant used may be between about 0.0001% and about 10%. In some embodiments, the preparation may be substantially free of surfactant.

In some embodiments, the formulation, e.g., preparation, may include other components that may enhance effectiveness of ammonia oxidizing bacteria, maintain or enhance viability of ammonia oxidizing bacteria, or enhance a treatment or indication.

In some embodiments, a chelator may be included in the preparation. A chelator may be a compound that may bind with another compound, e.g., a metal. The chelator may provide assistance in removing an unwanted compound from an environment, or may act in a protective manner to reduce or eliminate contact of a particular compound with an environment, e.g., ammonia oxidizing bacteria, e.g. a preparation of ammonia oxidizing bacteria, e.g., an excipient. In some embodiments, the preparation may be substantially free of chelator.

Formulations may also contain anti-oxidants, buffers, bacteriostats that prevent the growth of undesired bacteria, solutes, and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of a sterile liquid carrier, for example saline or water-for-injection, immediately prior to use. Extemporaneous solutions and suspensions may be prepared from powders, granules and tablets of the kind previously described. Exemplary compositions include solutions or suspensions which can contain, for example, suitable non-toxic, pharmaceutically acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor. An aqueous carrier may be, for example, an isotonic buffer solution at a pH of from about 3.0 to about 8.0, a pH of from about 3.5 to about 7.4, for example from 3.5 to 6.0, for example from 3.5 to about 5.0. Useful buffers include sodium citrate-citric acid and sodium phosphate-phosphoric acid, and sodium acetate/acetic acid buffers. The composition in some embodiments does not include oxidizing agents.

Excipients that can be included are, for instance, proteins, such as human serum albumin or plasma preparations. If desired, the pharmaceutical composition may also contain minor amounts of non-toxic auxiliary substances, such as wetting or emulsifying agents, preservatives, and pH buffering agents and the like, for example sodium acetate or sorbitan monolaurate. In some embodiments, excipients, e.g., a pharmaceutically acceptable excipient or a cosmetically acceptable excipient, may comprise an anti-adherent, binder, coat, disintegrant, filler, flavor, color, lubricant, glidant, sorbent, preservative, or sweetener. In some embodiments, the preparation may be substantially free of excipients.

In some embodiments, the preparation may be substantially free of one or more of the compounds or substances listed in the disclosure.

Exemplary compositions for aerosol administration include solutions in saline, which can contain, for example, benzyl alcohol or other suitable preservatives, absorption promoters to enhance bioavailability, and/or other solubilizing or dispersing agents. Conveniently in compositions for aerosol administration the ammonia oxidizing bacteria, e.g., *N. eutropha* is delivered in the form of an aerosol spray presentation from a pump. In other embodiments, compositions for aerosol administration of the ammonia oxidizing bacteria, e.g., *N. eutropha* is delivered in the form of an aerosol spray presentation from a pressurized pack or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin can be formulated to contain a powder mix of the *N. eutropha* and a suitable powder base, for example lactose or starch. In certain embodiments, *N. eutropha* is administered as an aerosol from a metered dose valve, through an aerosol adapter also known as an actuator. Optionally, a stabilizer is also included, and/or porous particles for deep lung delivery are included (e.g., see U.S. Pat. No. 6,447,743). The composition or preparation may be in a form that may be capable of being aerosolized, sprayed or misted, i.e., in the form of a mist. The preparation of ammonia oxidizing bacteria may be ammonia oxidizing bacteria in an aqueous buffer solution comprising, consisting essentially of, or consisting of disodium phosphate and magnesium chloride, for example, 50 mM $Na_2HPO_4$ and 2 mM $MgCl_2$, and which may be referred to as AO+Mist throughout this disclosure. The AO+Mist preparation includes ammonia oxidizing bacteria at a concentration of $1\times10^9$ CFU/mL in an aqueous buffer solution of 50 mM $Na_2HPO_4$ and 2 mM $MgCl_2$.

Formulations may be presented with carriers such as cocoa butter, synthetic glyceride esters or polyethylene glycol. Such carriers are typically solid at ordinary temperatures, but liquefy and/or dissolve at body temperature to release the ammonia oxidizing bacteria, e.g., *N. eutropha*.

Exemplary compositions for topical administration include a topical carrier such as Plastibase (mineral oil gelled with polyethylene). In some aspects, the composition and/or excipient may be in the form of one or more of a liquid, a solid, or a gel. For example, liquid suspensions may include, but are not limited to, water, saline, phosphate-buffered saline, an ammonia oxidizing storage buffer, or an aqueous buffer solution comprising, for example, $Na_2HPO_4$ and $MgCl_2$, e.g., 50 mM $Na_2HPO_4$ and 2 mM $MgCl_2$.

Gel formulations may include, but are not limited to agar, silica, polyacrylic acid (for example Carbopol®), carboxymethyl cellulose, starch, guar gum, alginate or chitosan.

In some embodiments, the formulation may be supplemented with an ammonia source including, but not limited to ammonium chloride or ammonium sulfate.

In some embodiments, an ammonia oxidizing bacteria composition, e.g., *N. eutropha* composition is formulated to improve NO penetration into the skin. A gel-forming material such as KY jelly or various hair gels would present a diffusion barrier to NO loss to ambient air, and so improve the skin's absorption of NO. The NO level in the skin will generally not greatly exceed 20 nM/L because that level activates GC and would cause local vasodilatation and oxidative destruction of excess NO.

It should be understood that in addition to the ingredients particularly mentioned above, the formulations as described herein may include other agents conventional in the art having regard to the type of formulation in question.

The formulation, e.g., preparation, e.g., composition may be provided in a container, delivery system, or delivery device, having a weight, including or not including the contents of the container, that may be less than about 50, 100, 200, 300, 400, 500, 600, 700, 800, 900, 1000, 1500, or 2000 grams.

Suitable unit dosage formulations are those containing an effective dose, as herein before recited, or an appropriate fraction thereof, of ammonia oxidizing bacteria, e.g., *N. eutropha*.

A therapeutically effective amount of ammonia oxidizing bacteria, e.g., *N. eutropha* may be administered as a single pulse dose, as a bolus dose, or as pulse doses administered over time. Thus, in pulse doses, a bolus administration of ammonia oxidizing bacteria, e.g., *N. eutropha* is provided, followed by a time period wherein ammonia oxidizing bacteria, e.g., *N. eutropha* is administered to the subject, followed by a second bolus administration. In specific, non-limiting examples, pulse doses are administered during the course of a day, during the course of a week, or during the course of a month.

A therapeutically effective amount of ammonia oxidizing bacteria, e.g., *N. eutropha* may be administered in the form of an aerosol or mist as a single spray or pump, or multiple sprays or pumps. In a single administration, one or more sprays or pumps may be actuated. A therapeutically effective amount may be the result of a single administration, or multiple administrations, during the course of one or more days, during the course of one or more weeks, during the course of one or more months, or longer.

A therapeutically effective amount may be an amount sufficient to improve any one or more of acne counts, PIH/PIE Lesion Grading, SkinDex16 data, modified Griffiths' 10-point scale, Tolerability Evaluations, Sebumeter Measurements, and Investigator's Global Acne (IGA) scale, at 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, 50, 52 weeks.

In some embodiments, a preparation of ammonia oxidizing bacteria, e.g., a formulation, e.g., a composition, may be applied for a pre-determined number of days. This may be based, for example, at least in part, on the severity of the condition or disease, the response to the treatment, the dosage applied and the frequency of the dose. For example, the preparation may be applied for about 1-3, 3-5, 5-7, 7-9, 5-10, 10-14, 12-18, 12-21, 21-28, 28-35, 35-42, 42-49, 49-56, 46-63, 63-70, 70-77, 77-84, 84-91 days, for about 1 month, for about 2 months, for about 3 months. In some embodiments, the ammonia oxidizing bacteria is administered for an indefinite period of time, e.g., greater than one year, greater than 5 years, greater than 10 years, greater than 15 years, greater than 30 years, greater than 50 years, greater than 75 years. In certain aspects, the preparation may be applied for about 16 days. In certain aspects, the preparation may be applied for about 4 weeks.

In some embodiments, a preparation of ammonia oxidizing bacteria, e.g., a formulation, e.g., a composition, may be applied a pre-determined number of times per day. This may be based, for example, at least in part, on the severity of the condition or disease, the response to the treatment, the dosage applied and the frequency of the dose. For example, the preparation may be applied 1, 2, 3, 4, 5, 6, 7, 8, 9, 10, 11, 12, 13, 14, 15, 16, 17, 18, 19, 20, 21, 22, 23, 24 times per day.

In some embodiments, the preparation may be applied one time per day. In other embodiments, the preparation may be applied two times per day. In some embodiments, the preparation may be applied a first pre-determined amount for a certain number of days, and a second pre-determined amount for a certain subsequent number of days. In some embodiments, the preparation may be applied for about 16 days. In certain aspects, the preparation may be applied for about 4 weeks.

Consumer Products

Ammonia oxidizing bacteria, e.g., *N. eutropha* may be associated with a variety of consumer products, and examples of such products are set out below and be comprised of formulations, compositions, or preparations disclosed throughout this disclosure. In some embodiments, the ammonia oxidizing bacteria, e.g., *N. eutropha* associated with a product is admixed with the product, for example, spread evenly throughout the product, and in some embodiments, ammonia oxidizing bacteria, e.g., the *N. eutropha* associated with a product is layered on the product.

In some embodiments, ammonia oxidizing bacteria, e.g., *N. eutropha* is associated with a powder. Powders are typically small particulate solids that are not attached to each other and that can flow freely when tilted. Exemplary powders for consumer use include talcum powder and some cosmetics (e.g., powder foundation).

In some embodiments, the ammonia oxidizing bacteria is associated with a cosmetic. The cosmetic may be a substance for topical application intended to alter a person's appearance, e.g., a liquid foundation, a powder foundation, blush, or lipstick, and may be referred to as a preparation. The cosmetic may be any substance recited in the Food and Drug Administration regulations, e.g., under 21 C.F.R. § 720.4.

The preparation, e.g., the cosmetic, may be at least one of a baby product, e.g., a baby shampoo, a baby lotion, a baby oil, a baby powder, a baby cream; a bath preparation, e.g., a bath oil, a tablet, a salt, a bubble bath, a bath capsule; an eye makeup preparation, e.g., an eyebrow pencil, an eyeliner, an eye shadow, an eye lotion, an eye makeup remover, a mascara; a fragrance preparation, e.g., a colognes, a toilet water, a perfume, a powder (dusting and talcum), a sachet; hair preparations, e.g., hair conditioners, hair sprays, hair straighteners, permanent waves, rinses, shampoos, tonics, dressings, hair grooming aids, wave sets; hair coloring preparations, e.g., hair dyes and colors, hair tints, coloring hair rinses, coloring hair shampoos, hair lighteners with color, hair bleaches; makeup preparations, e.g., face powders, foundations, leg and body paints, lipstick, makeup bases, rouges, makeup fixatives; manicuring preparations, e.g., basecoats and undercoats, cuticle softeners, nail creams and lotions, nail extenders, nail polish and enamel, nail polish and enamel removers; oral hygiene products, e.g., dentifrices, mouthwashes and breath fresheners; bath soaps and detergents, deodorants, douches, feminine hygiene deodorants; shaving preparations, e.g., aftershave lotions, beard softeners, talcum, preshave lotions, shaving cream, shaving soap; skin care preparations, e.g., cleansing, depilatories, face and neck, body and hand, foot powders and sprays, moisturizing, night preparations, paste masks, skin fresheners; and suntan preparations, e.g., gels, creams, and liquids, and indoor tanning preparations.

In some embodiments, the formulations, compositions, or preparations described herein, may comprise, be provided as, or disposed in at least one of a baby product, e.g., a baby shampoo, a baby lotion, a baby oil, a baby powder, a baby cream; a bath preparation, e.g., a bath oil, a tablet, a salt, a bubble bath, a bath capsule; a powder (dusting and talcum), a sachet; hair preparations, e.g., hair conditioners, rinses, shampoos, tonics, face powders, cuticle softeners, nail creams and lotions, oral hygiene products, mouthwashes, bath soaps, douches, feminine hygiene deodorants; shaving preparations, e.g., aftershave lotions, skin care preparations, e.g., cleansing, face and neck, body and hand, foot powders and sprays, moisturizing, night preparations, paste masks, skin fresheners; and suntan preparations, e.g., gels, creams, and liquids.

In some embodiments, ammonia oxidizing bacteria, e.g., *N. eutropha* is associated with a cosmetic. The cosmetic may be a substance for topical application intended to alter a person's appearance, e.g., a liquid foundation, a powder foundation, blush, or lipstick. Other components may be added to these cosmetic preparations as selected by one skilled in the art of cosmetic formulation such as, for example, water, mineral oil, coloring agent, perfume, aloe, glycerin, sodium chloride, sodium bicarbonate, pH buffers, UV blocking agents, silicone oil, natural oils, vitamin E, herbal concentrates, lactic acid, citric acid, talc, clay, calcium carbonate, magnesium carbonate, zinc oxide, starch, urea, and erythorbic acid, or any other excipient known by one of skill in the art, including those disclosed herein.

In some embodiments, the preparation may be disposed in, or provided as, a powder, cosmetic, cream, stick, aerosol, e.g., mist, salve, wipe, or bandage.

In some embodiments, ammonia oxidizing bacteria, e.g., *N. eutropha* is associated with a cream. The cream may be a fluid comprising a thickening agent, and generally has a consistency that allows it to be spread evenly on the skin. Exemplary creams include moisturizing lotion, face cream, and body lotion.

In some embodiments, ammonia oxidizing bacteria, e.g., the *N. eutropha* is associated with a stick. A stick is typically a solid that, when placed in contact with a surface, transfers some of the stick contents to the surface. Exemplary sticks include deodorant stick, lipstick, lip balm in stick form, and sunscreen applicator sticks.

In some embodiments, ammonia oxidizing bacteria, e.g., the *N. eutropha* is associated with an aerosol. An aerosol is typically a colloid of fine solid particles or fine liquid droplets, in a gas such as air. Aerosols may be created by placing the *N. eutropha* (and optionally carriers) in a vessel under pressure, and then opening a valve to release the contents. The container may be designed to only exert levels of pressure that are compatible with *N. eutropha* viability. For instance, the high pressure may be exerted for only a short time, and/or the pressure may be low enough not to impair viability. Examples of consumer uses of aerosols include for sunscreen, deodorant, perfume, hairspray, and insect repellant. The aerosol may be referred to as a mist.

In some embodiments, ammonia oxidizing bacteria, e.g., the *N. eutropha* is associated with a salve. A salve may be a topically applied agent with a liquid or cream-like consistency, intended to protect the skin or promote healing. Examples of salves include burn ointments and skin moisturizers.

In some embodiments, ammonia oxidizing bacteria, e.g., the N. eutropha is associated with a wipe. A wipe may be a flexible material suitable for topically applying a liquid or cream onto skin. The wipe may be, e.g., paper-based or cloth based. Exemplary wipes include tissues and wet wipes.

The compositions comprising ammonia oxidizing bacteria, e.g., N. eutropha may also comprise one or more of a moisturizing agent, deodorizing agent, scent, colorant, insect repellant, cleansing agent, or UV-blocking agent.

For instance, the moisturizing agent may be an agent that reduces or prevents skin dryness. Exemplary moisturizing agents include humectants (e.g., urea, glycerin, alpha hydroxy acids and dimethicone) and emollients (e.g., lanolin, mineral oil and petrolatum). Moisturizing agents may be included, e.g., in ammonia oxidizing bacteria, e.g., N. eutropha-containing creams, balms, lotions, or sunscreen.

A deodorizing agent may be an agent that reduces unwanted odors. A deodorizing agent may work by directly neutralizing odors, preventing perspiration, or preventing the growth of odor-producing bacteria. Exemplary deodorizing agents include aluminum salts (e.g., aluminum chloride or aluminum chlorohydrate), cyclomethicone, talc, baking soda, essential oils, mineral salts, hops, and witch hazel. Deodorizing agents are typically present in spray or stick deodorants, and can also be found in some soaps and clothing.

An insect repellant may be an agent that can be applied to surfaces (e.g., skin) that discourage insects and other arthropods from lighting on the surface. Insect repellants include DEET (N,N-diethyl-m-toluamide), p-menthane-3,8-diol (PMD), icaridin, nepetalactone, citronella oil, neem oil, bog myrtle, dimethyl carbate, Tricyclodecenyl allyl ether, and IR3535 (3-[N-Butyl-N-acetyl]-aminopropionic acid, ethyl ester).

A cleansing agent may be an agent that removes dirt or unwanted bacteria from a surface like skin. Exemplary cleansing agents include bar soaps, liquid soaps, and shampoos.

A UV-blocking agent may be an agent that can be applied to a surface to reduce the amount of ultraviolet light the surface receives. A UV-blocking agent may block UV-A and/or UV-B rays. A UV blocking agent can function by absorbing, reflecting, or scattering UV. Exemplary UV-blocking agents include absorbers, e.g., homosalate, octisalate (also called octyl salicylate), octinoxate (also called octyl methoxycinnamate or OMC), octocrylene, oxybenzone, and avobenzone, and reflectors (e.g., titanium dioxide and zinc oxide). UV-blocking agents are typically presents in sunscreens, and can also be found in skin creams and some cosmetics.

In some embodiments, ammonia oxidizing bacteria, e.g., N. eutropha is associated with a conditioner. Conditioner generally refers to a substance with cream-like consistency that can be applied to hair to improve its appearance, strength, or manageability.

In some embodiments, ammonia oxidizing bacteria, e.g., N. eutropha is associated with cloth. Cloth generally refers to a flexible material suitable to be made into clothing, e.g., having enough material strength to withstand everyday motion by a wearer. Cloth can be fibrous, woven, or knit; it can be made of a naturally occurring material or a synthetic material. Exemplary cloth materials include cotton, flax, wool, ramie, silk, denim, leather, nylon, polyester, and spandex, and blends thereof.

In some embodiments, ammonia oxidizing bacteria, e.g., N. eutropha is associated with yarn. Yarn generally refers to a long, thin spun flexible material that is suitable for knitting or weaving. Yarn can be made of, e.g., wool, cotton, polyester, and blends thereof.

In some embodiments, ammonia oxidizing bacteria, e.g., N. eutropha is associated with thread. Thread generally refers to a long, thin spun flexible material that is suitable for sewing. Thread generally has a thinner diameter than yarn. Thread can be made of, e.g., cotton, polyester, nylon, silk, and blends thereof.

Articles of clothing such as, for example, shoes, shoe inserts, pajamas, sneakers, belts, hats, shirts, underwear, athletic garments, helmets, towels, gloves, socks, bandages, and the like, may also be treated with ammonia oxidizing bacteria, e.g., N. eutropha. Bedding, including sheets, pillows, pillow cases, and blankets may also be treated with ammonia oxidizing bacteria, e.g., N. eutropha. In some embodiments, areas of skin that cannot be washed for a period of time may also be contacted with ammonia oxidizing bacteria, e.g., N. eutropha. For example, skin enclosed in orthopedic casts which immobilize injured limbs during the healing process, and areas in proximity to injuries that must be kept dry for proper healing such as stitched wounds may benefit from contact with the ammonia oxidizing bacteria, e.g., N. eutropha.

In some aspects, the present disclosure provides a wearable article comprising an N. eutropha strain as described herein. A wearable article may be a light article that can be closely associated with a user's body, in a way that does not impede ambulation. Examples of wearable articles include a wristwatch, wristband, headband, hair elastic, hair nets, shower caps, hats, hairpieces, and jewelry. The wearable article comprising an ammonia oxidizing bacteria, e.g., N. eutropha strain described herein may provide, e.g., at a concentration that provides one or more of a treatment or prevention of a skin disorder, a treatment or prevention of a disease or condition associated with low nitrite levels, a treatment or prevention of body odor, a treatment to supply nitric oxide to a subject, or a treatment to inhibit microbial growth.

In some embodiments, the ammonia oxidizing bacteria, e.g., N. eutropha is associated with a product intended to contact the hair, for example, a brush, comb, shampoo, conditioner, headband, hair elastic, hair nets, shower caps, hats, and hairpieces. Nitric oxide formed on the hair, away from the skin surface, may be captured in a hat, scarf or face mask and directed into inhaled air.

Articles contacting the surface of a human subject, such as a diaper, may be associated with ammonia oxidizing bacteria, e.g., N. eutropha. Because diapers are designed to hold and contain urine and feces produced by incontinent individuals, the urea in urine and feces can be hydrolyzed by skin and fecal bacteria to form free ammonia which is irritating and may cause diaper rash. Incorporation of bacteria that metabolize urea into nitrite or nitrate, such as ammonia oxidizing bacteria, e.g., N. eutropha, may avoid the release of free ammonia and may release nitrite and ultimately NO which may aid in the maintenance of healthy skin for both children and incontinent adults. The release of nitric oxide in diapers may also have antimicrobial effects on disease causing organisms present in human feces. This effect may continue even after disposable diapers are disposed of as waste and may reduce the incidence of transmission of disease through contact with soiled disposable diapers.

In some embodiments, the product comprising ammonia oxidizing bacteria, e.g., *N. eutropha* is packaged. The packaging may serve to compact the product or protect it from damage, dirt, or degradation. The packaging may comprise, e.g., plastic, paper, cardboard, or wood. In some embodiments the packaging is impermeable to bacteria. In some embodiments the packaging is permeable to oxygen and/or carbon dioxide.

4. Methods of Treatment with Ammonia Oxidizing Bacteria, e.g., *N. eutropha*

The present disclosure provides various methods of treating diseases and conditions using ammonia oxidizing bacteria, e.g., *N. eutropha*. The ammonia oxidizing bacteria, e.g., *N. eutropha* that may be used to treat diseases and conditions include all the ammonia oxidizing bacteria, e.g., *N. eutropha* compositions described in this application, e.g. a purified preparation of optimized ammonia oxidizing bacteria, e.g., *N. eutropha*, for instance strain D23.

The ammonia oxidizing bacteria administered to treat a skin condition, e.g., acne, e.g., acne vulgaris may be selected from the group consisting of *Nitrosomonas, Nitrosococcus, Nitrosospira, Nitrosocystis, Nitrosolobus, Nitrosovibrio*, and combinations thereof. In certain aspects, the ammonia oxidizing bacteria may be *Nitrosomonas eutropha* (*N. eutropha*). In certain aspects, the ammonia oxidizing bacteria is *N. eutropha* D23, having ATCC accession number PTA-121157.

The methods may be provided to administer, or deliver, a therapeutic product, or a cosmetic product.

The ammonia oxidizing bacteria, e.g., *N. eutropha* may be used to treat skin conditions such as acne, rosacea, eczema, or psoriasis.

In certain embodiments, the disclosure provides uses for treating a skin condition or disease (e.g., inhibiting microbial growth on a subject's skin), ammonia oxidizing bacteria, e.g., an optionally axenic composition of *N. eutropha* having one or more of: (1) an optimized growth rate, (2) an optimized $NH_4^+$ oxidation rate, (3) an optimized resistance to $NH_3$, (4) an optimized resistance to, $NH_4^+$, and (5) an optimized resistance to, $NO_2^-$. For instance, the axenic *N. eutropha* composition may have properties (1) and (2); (2) and (3); (3) and (4); or (4) and (5) from the list at the beginning of this paragraph. As another example, the axenic *N. eutropha* composition may have properties (1), (2), and (3); (1), (2), and (4); (1), (2), and (5); (1), (3), and (4); (1), (3), and (5); (1), (4), and (5); (2), (3), and (4); (2), (3), and (5), or (3), (4), and (5) from the list at the beginning of this paragraph. As a further example, the optionally axenic *N. eutropha* composition may have properties (1), (2), (3), and (4); (1), (2), (3), and (5); (1), (2), (4), and (5); (1), (3), (4), and (5); or (2), (3), (4), and (5) from the list at the beginning of this paragraph. In some embodiments, the axenic *N. eutropha* composition has properties (1), (2), (3), (4), and (5) from the list at the beginning of this paragraph.

The ammonia oxidizing bacteria may be used to treat a skin condition, e.g., acne, e.g., acne vulgaris.

In some embodiments, ammonia oxidizing bacteria, e.g., *N. eutropha*, e.g., optionally axenic *N. eutropha* (e.g., strain D23) are used to treat a subject. Subjects may include an animal, a mammal, a human, a non-human animal, a livestock animal, or a companion animal.

The subject may be female or male. The subject may be one of the following ethnicity/race: Asian, black or African American, Hispanic or Latino, white, or multi-racial. The subject may be characterized as having at least one of the following skin types: normal, oily, and combination skin. The subject may be characterized as having one of the following Fitzpatrick skin types: I, II, III, IV, V. The acne type of the subject may be one of adolescent acne or adult acne. The age of the subject may be between about 12-15, 16-18, 19-28, or greater than 28.

Adult acne refers acne of a subject that is age 19, or older. Adolescent acne refers to acne of a subject that is less than 19 years old.

In some embodiments, methods of treating a skin disorder, e.g., acne, e.g. acne vulgaris, of a subject are provided comprising administering, e.g., applying, e.g., topically administering, ammonia oxidizing bacteria, e.g., a preparation comprising ammonia oxidizing bacteria, to a surface of the subject.

An amount and/or a frequency of administration, e.g., application, may be sufficient to reduce the amount or concentration of pathogenic bacteria, e.g., *Propionibacterium acnes*, on the surface of the subject. The amount may be a therapeutically effective dose of ammonia oxidizing bacteria.

Administration, e.g., administering, may provide for treatment of inflammatory lesions. The inflammatory lesions may be in the form of any one or more of papules, pustules, and cysts/nodules.

Papules and pustules may be described as pimples caused by irritated pores. Papules are small bumps that appear on the skin and typically have a rough texture and are hard when touched. Papules may occur when the wall of a hair follicle breaks and caves in. Pustules are similar to papules except that yellowish, liquid pus may fill them. White blood cells rise to the surface of the skin of papules to form pustules.

Blocked pores may get more irritated and larger, and penetrate deeper into the skin to provide nodules and cysts. Cysts typically form below the skin surface, and a build up of white blood cells, oils and fluids begin to build up causing the appearance of cysts, or pus filled regions. Nodules are hard and may form when the bottom of a follicle will break off, which may cause the follicle to collapse. This may produce a large, sore bump on the surface of the skin called a nodule. Nodules may extend into deep layers of the skin.

Administration, e.g., administering, may provide for treatment of non-inflammatory lesions. The non-inflammatory lesions may be comedones, e.g., open comedones and/or closed comedones.

Closed comedones, or whiteheads, are small plugged follicles, the contents of which are not exposed to the skin. Open comedones or blackheads are small follicles with dilated openings to the skin allowing oxidation of the debris within the follicle leading to the black color.

Administration, e.g., administering, may provide for treatment or improvement of post-inflammatory hyperpigmentation/post inflammatory erythema (PIH/PIE) lesions. Hyperpigmentation is characterized by a darkening of an area of skin cuased by the overproduction of a pigment in the skin, e.g., melanin. Post-inflammatory refers to localized skin erythema following any type of skin inflammation, e.g., acne-related skin inflammation, including erythema that may result in a scar.

Administration, e.g., administering, may provide for treatment or improvement of one or more of erythema, edema, scaling, stinging, burning, and itching. Erythema may refer to superficial reddening of the skin, typically in patches, as a result of injury or irritation, causing dilatation of the blood capillaries. Edema may refer to a condition characterized by an excess of watery fluid collecting in the cavities or tissues of a subject, e.g., swelling.

Administration, e.g., administering, may provide for treatment or improvement of one or more of oily appearance, pore appearance, radiance, blotchiness, skin tone evenness, visual smoothness, and tactile smoothness.

Administration, e.g., administering, may provide for treatment or improvement in sebumeter measurements. Sebum is an oily secretion of sebaceous glands. Sebum may be found on any area of a body of a subject, for example, Administration may provide for one or more of the following: reduces inflammation of lesions, reduces the frequency of lesions, and decreases the presence of pathogenic bacteria, e.g., *Propionibacterium acnes*.

Administration may provide for the decrease of the presence of pathogenic bacteria, e.g., *Propionibacterium acnes*. Administration may provide for an improvement in the subject's emotional assessment of their disease as measured by Skindex16 Quality of Life Survey. Administration may provide for an improvement in one or more of the following: skin condition hurting in the subject, persistence/reoccurrence of skin condition in the subject, and appearance of skin condition in the subject. Administration may provide for an improvement (decrease) in one or more of the following, according to clinical grading: grading scores for visual and tactile smoothness, and blotchiness.

Administration, e.g., administering of the ammonia oxidizing bacteria, e.g. preparation of ammonia oxidizing bacteria may comprise pre-treating the subject with ammonia oxidizing bacteria. For example, pre-treating may involve administration of the ammonia oxidizing bacteria prior to an acne or acne related outbreak, for example prior to emergence of an acne-related symptom or condition. Administration may comprise topically administering prior to occurrence of the skin disorder, e.g., acne, e.g., acne vulgaris.

Administration, e.g, topically administering may comprise topically administering to the subject an effective dose of ammonia oxidizing bacteria. The effective does may be any one or more of about $0.1 \times 10^9$, $0.2 \times 10^9$, $0.3 \times 10^9$, $0.4 \times 10^9$, $0.5 \times 10^9$, $0.6 \times 10^9$, $0.7 \times 10^9$, $0.8 \times 10^9$, $0.9 \times 10^9$, $1.0 \times 10^9$, $1.2 \times 10^9$, $1.4 \times 10^9$, $1.5 \times 10^9$, $1.6 \times 10^9$, $1.8 \times 10^9$, $2.0 \times 10^9$, $2.2 \times 10^9$, $2.4 \times 10^9$, $2.6 \times 10^9$, $2.8 \times 10^9$, $3.0 \times 10^9$, $3.2 \times 10^9$, $3.4 \times 10^9$, $3.6 \times 10^9$, $3.8 \times 10^9$, $4.0 \times 10^9$, $4.2 \times 10^9$, $4.4 \times 10^9$, $4.6 \times 10^9$, $4.8 \times 10^9$, $5.0 \times 10^9$, $5.5 \times 10^9$, $6.0 \times 10^9$, $6.5 \times 10^9$, $7.0 \times 10^9$, $7.5 \times 10^9$, $8.0 \times 10^9$, $8.5 \times 10^9$, $9.0 \times 10^9$, $9.5 \times 10^9$, $10.0 \times 10^9$, $12 \times 10^9$, $14 \times 10^9$, $16 \times 10^9$, $18 \times 10^9$, $20 \times 10^9$, $25 \times 10^9$, $30 \times 10^9$, $40 \times 10^9$, $50 \times 10^9$ CFU.

The effective dose may also comprise an ammonia oxidizing bacteria having a dose as described herein, in combination with ammonia, for example, an ammonia concentration of between about 0.01 mM to about 100 mM. For example, the ammonia concentration may be about 0.01, 0.05, 0.1, 0.2, 0.4, 0.5, 0.6, 0.8, 1.0, 1.2-1.4, 1.6, 1.8, 2.0, 2.2, 2.4, 2.5, 2.6, 2.8, 3.0, 3.2, 3.4, 3.6, 3.8, 4.0, 4.2, 4.4, 4.5, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 10.0, 15.0, 20.0, 25.0, 30.0, 35.0, 40.0, 45.0, 50.0, 55.0, 60.0, 65.0, 70.0, 75.0, 80.0, 85.0, 90.0, 95.0, 100.0 mM.

The skin disorder, e.g., acne, e.g., acne vulgaris may be present at a target site of the subject, which may comprise one or more undesirable bacteria, e.g., pathogenic bacteria. The target site may comprise *Propionibacterium acnes*.

The method of treating may further comprise determining whether the subject is in need of treating the skin disorder. This may involve determining whether the subject is in need of treating acne, e.g., acne vulgaris. The method may further comprise selecting the subject in need of treating the skin disorder.

In certain embodiments, the method may comprise selecting the subject on the basis of the subject being in need of a reduction of the amount or concentration of pathogenic bacteria, e.g., *Propionibacterium acnes*, on the surface of the subject.

Administration may comprise self-administration of the ammonia oxidizing bacteria by the subject. Administration may comprise administration of the ammonia oxidizing bacteria by one who is not the subject. The ammonia oxidizing bacteria may be administered, e.g., applied to any part of the body of the subject, for example, head, shoulder, arm, leg, underarm, torso, feet, knee, ankle, or buttocks. In certain aspects, the ammonia oxidizing bacteria may be applied to any one or more of the face, neck, and scalp of the subject.

In some embodiments, administration may comprise administering, e.g., applying the ammonia oxidizing bacteria, e.g., the preparation of ammonia oxidizing bacteria, a suitable number of times to provide an effective treatment of acne as described by improvement in any one or more of the measurement techniques described herein. For example, administration may occur about 1, 2, 3, 4, 5, 6, 7, 8, 9, 10, 11, 12, 13, 14, 15, 16, 17, 18, 19, 20, 21, 22, 23, or 24 times per day. Administration may comprise administering, e.g., applying the ammonia oxidizing bacteria, e.g., the preparation of ammonia oxidizing bacteria, one time per day. Administration may comprise administering, e.g., applying the ammonia oxidizing bacteria, e.g., the preparation of ammonia oxidizing bacteria, two times per day.

In some embodiments, administration of the preparation may comprise administering, e.g., applying the ammonia oxidizing bacteria, e.g., the preparation of ammonia oxidizing bacteria, for a suitable time period to provide an effective treatment of acne as described by improvement in any one or more of the measurement techniques described herein. Administration of the preparation may comprise administering, e.g., applying the ammonia oxidizing bacteria, e.g., the preparation of ammonia oxidizing bacteria for about 1-3, 3-5, 5-7, 7-9, 5-10, 10-14, 12-18, 12-21, 21-28, 28-35, 35-42, 42-49, 49-56, 46-63, 63-70, 70-77, 77-84, or 84-91 days. The preparation, for example, may be applied for about 7 days. The preparation, for example, may be applied for about 14 days. The preparation, for example, may be applied for about 21 days. The preparation, for example, may be applied for about 28 days.

The ammonia oxidizing bacteria, e.g., preparation of ammonia oxidizing bacteria, may be in a form, e.g., medium, that may be capable of being aerosolized, sprayed or misted, i.e., in the form of a mist. The ammonia oxidizing bacteria, e.g., preparation of ammonia oxidizing bacteria, may be administered, e.g., applied, e.g., topically applied, as an aerosol or mist. The aerosol or mist may comprise an aqueous medium. The preparation of ammonia oxidizing bacteria may be in a preparation that maintains or promotes viability of the ammonia oxidizing bacteria. The preparation may be in a buffer solution, e.g., an aqueous buffer solution. The buffer solution, e.g., aqueous buffer solution. The aqueous buffer may comprises disodium phosphate and magnesium chloride. The aqueous buffer may comprise 50 mM $Na_2HPO_4$ and 2 mM $MgCl_2$ in water. The concentration of ammonia oxidizing bacteria may be any concentration of AOBs disclosed herein. In certain aspects, the aqueous buffer may comprise 50 mM $Na_2HPO_4$ and 2 mM $MgCl_2$ in water, and further comprise ammonia oxidizing bacteria, e.g., D23 *N. eutropha* at a concentration of $1\times10^9$ CFU/mL.

The aqueous buffer solution, prior to addition of the ammonia oxidizing bacteria, may comprise, consist essentially of or consist of disodium phosphate and magnesium chloride, for example, 50 mM $Na_2HPO_4$ and 2 mM $MgCl_2$ in water.

In some embodiments, the preparation may comprise at least one of ammonia, ammonium salts, and urea. The preparation may comprise a controlled release material. For example, the controlled release material may be a slow release material. The preparation of ammonia oxidizing bacteria may comprise an excipient. The excipient may be a pharmaceutically acceptable excipient or a cosmetically acceptable excipient, as disclosed throughout this disclosure. The excipient may be a surfactant, for example, a surfactant that is disclosed throughout this disclosure. In some embodiments, the excipient, e.g., the pharmaceutically acceptable excipient or the cosmetically acceptable excipient, comprises an anti-adherent, binder, coat, disintegrant, filler, flavor, color, lubricant, glidant, sorbent preservative, or sweetener.

The preparation may be substantially free of other organisms. The preparation may comprise a second organism, e.g., an organism selected from the group consisting of *Lactobacillus, Streptococcus, Bifidobacter*, and combinations thereof.

In some embodiments, the preparation for treatment of a skin condition, e.g., acne, e.g., acne vulgaris, may be disposed in or provided as a powder, cosmetic, cream, stick, aerosol, e.g., mist, salve, wipe, or bandage. In some embodiments, the preparation for treatment of a skin condition, e.g., acne, e.g., acne vulgaris may comprise a moisturizing agent, deodorizing agent, cent, colorant, insect repellant, cleansing agent, or UV-blocking agent.

In some embodiments, the preparation for treatment of a skin condition, e.g., acne, e.g., acne vulgaris, may comprise ammonia oxidizing bacteria having a concentration of about $10^8$ to about $10^{14}$ CFU/mL of ammonia oxidizing bacteria. In certain aspects, the preparation may comprise between about $1\times10^9$ CFU/mL to about $10\times10^9$ CFU/mL ammonia oxidizing bacteria. In some embodiments, the preparation may comprise ammonia oxidizing bacteria comprises between about 50 milligrams (mg) and about 1000 mg of ammonia oxidizing bacteria. In some embodiments, the mass ratio of ammonia oxidizing bacteria to the excipient, e.g., the pharmaceutically acceptable excipient or the cosmetically acceptable excipient is in a range of about 0.1 grams to about 1 gram per liter.

The preparation of ammonia oxidizing bacteria that may be used to treat acne may be provided in a container, the preparation and the container having a weight of less than about 50, 100, 200, 300, 400, 500, 600, 700, 800, 900, 1000, 1500, or 2000 grams.

The method may further comprise obtaining a sample from the surface of the skin. The sample may be taken any time prior to administration of the ammonia oxidizing bacteria, or any time subsequent to administration of the ammonia oxidizing bacteria. For example, the sample may be taken about 1 minute, 5 minutes, 10, 15, 20, 25, 30, 45, 60, 90, 120 minutes prior to administration, or 3 hours, 4, 5, 6, 7, 8, 12, 18, 24 hours prior to administration, or 1 week, 2, 3, 4, 5, 6, 7, 8, 9, 10, 11, 12 weeks prior to administration. Alternatively, or in addition to, the sample may be taken about 1 minute, 5 minutes, 10, 15, 20, 25, 30, 45, 60, 90, 120 minutes subsequent to administration, or 3 hours, 4, 5, 6, 7, 8, 12, 18, 24 hours subsequent to administration, or 1 week, 2, 3, 4, 5, 6, 7, 8, 9, 10, 11, 12 weeks subsequent to administration.

The method may further comprise isolating DNA of bacteria in the sample. The bacteria may be *Propionibacterium acnes*. The administration of ammonia oxidizing bacteria provides for a decrease in *Propionibacterium acnes*. The decrease in *Propionibacterium acnes* may occur after about 1, 2, 3, 4, 5, 6, 7, 8, 9, 10, 11, 12, 13, 14, 15, 16, 17, 18, 19, 20, 21, 22, 23, 24, 25, 26, 27, 28, 35, 42, 49, 56, 63, 70, 77, 84, 91, 98, 105, or more days.

Use of cosmetic products, e.g., microbiome-compatible cosmetic products, e.g., shampoos, conditioners, and cleansers as described herein may be used in conjunction with the treatment of a skin condition, e.g., acne, e.g., acne vulgaris. These cosmetic products may be used in conjunction with administration of the ammonia oxidizing bacteria. For example, throughout the treatment period of time of administering the ammonia oxidizing bacteria to a subject, the cosmetic products may be used. The cosmetic products may be used for a period of time prior to commencement of treatment of the skin condition through administration of ammonia oxidizing bacteria to a subject. The cosmetic products may be used for a period of time subsequent to commencement of treatment of the skin condition through administration of ammonia oxidizing bacteria to a subject. The cosmetic products may be used for a period of time subsequent to discontinuation of treatment of the skin condition through administration of ammonia oxidizing bacteria to a subject.

In some embodiments, the subject may apply one or more cosmetic product, and wait a period of time before administration of the ammonia oxidizing bacteria. In other embodiments, the subject may administer the ammonia oxidizing bacteria, and wait a period of time before applying one or more cosmetic products.

The period of time the subject may wait may be about 1 minute, 5 minutes, 10, 15, 20, 25, 30, 45, 60, 90, 120 minutes, or 3 hours, 4, 5, 6, 7, 8, 12, 18, 24 hours after applying one or more cosmetic product and prior to administration of ammonia oxidizing bacteria.

The period of time the subject may wait may be about 1 minute, 5 minutes, 10, 15, 20, 25, 30, 45, 60, 90, 120 minutes, or 3 hours, 4, 5, 6, 7, 8, 12, 18, 24 hours after administering the ammonia oxidizing bacteria and prior to applying one or more cosmetic products.

The subject may be evaluated prior to beginning treatment, e.g., administering ammonia oxidizing bacteria. The subject may be evaluated subsequent to beginning treatment, e.g, subsequent to a first administration, e.g., application of ammonia oxidizing bacteria.

The subject may be evaluated 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 days; or 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 weeks; or 2.3 years, 4, or 5 years prior to beginning treatment, e.g., administering the ammonia oxidizing bacteria.

The subject may be evaluated 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 days; or 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52 weeks; or 2.3 years, 4, or 5 years subsequent to beginning treatment, e.g., a first administration, e.g, application of ammonia oxidizing bacteria.

Administration may occur at a time period before or after the subject cleanses, baths, or showers. For example, administration may occur at a time period that is 30, 60, 90, 120, 150, 180 minutes before or after the subject cleanses, baths, or showers.

In some embodiments, ammonia oxidizing bacteria, e.g., *N. eutropha*, e.g., optionally axenic *N. eutropha* described herein (e.g., the *N. eutropha* described throughout the disclosure, e.g., strain D23) are used to inhibit the growth of other organisms. For instance, *N. eutropha* D23 is well-adapted for long-term colonization of human skin, and in some embodiments it out-competes other bacteria that are undesirable on the skin. Undesirable skin bacteria include, e.g., those that can infect wounds, raise the risk or severity of a disease, or produce odors. Certain undesirable skin bacteria include *S. aureus, P. aeruginosa, S. pyogenes*, and *A. baumannii*. The *N. eutropha* described herein may outcompete other organisms by, e.g., consuming scarce nutrients, or generating byproducts that are harmful to other organisms, e.g., changing the pH of the skin to a level that is not conducive to the undesirable organism's growth.

Accordingly, the present disclosure provides, inter alia, a method of inhibiting microbial growth on a subject's skin, comprising topically administering to a human in need thereof an effective dose of ammonia oxidizing bacteria, e.g., *N. eutropha*, e.g., optionally axenic *N. eutropha* described herein as described herein (e.g., strain D23). Similarly, the present disclosure provides ammonia oxidizing bacteria, e.g., *N. eutropha*, e.g., optionally axenic *N. eutropha* described herein for use in inhibiting microbial growth on a subject's skin. Likewise, the present disclosure provides a use of ammonia oxidizing bacteria, e.g., *N. eutropha*, e.g., optionally axenic *N. eutropha* described herein in the manufacture of a medicament for inhibiting microbial growth on a subject's skin.

Accordingly, the present disclosure provides, inter alia, a method of treating a skin condition, e.g., acne, e.g., acne vulgaris, comprising topically administering to a human in need thereof an effective dose of ammonia oxidizing bacteria, e.g., *N. eutropha*, e.g., optionally axenic *N. eutropha* as described herein (e.g., strain D23). Similarly, the present disclosure provides ammonia oxidizing bacteria, e.g., *N. eutropha*, e.g., optionally axenic *N. eutropha* described herein (e.g., strain D23) for use in treating a skin condition, e.g., acne, e.g., acne vulgaris, on subject's skin. Likewise, the present disclosure provides a use of ammonia oxidizing bacteria, e.g., *N. eutropha*, e.g., optionally axenic *N. eutropha* described herein in the manufacture of a medicament for treating a skin condition, e.g., acne, e.g., acne vulgaris, on a subject's skin.

The present disclosure also provides a method of supplying nitric oxide to a subject, comprising positioning an effective dose of ammonia oxidizing bacteria, e.g., *N. eutropha*, e.g., optionally axenic *N. eutropha* described herein (e.g., strain D23) in close proximity to the subject. Similarly, the present disclosure provides ammonia oxidizing bacteria, e.g., *N. eutropha*, e.g., optionally axenic *N. eutropha* described herein (e.g., strain D23) for use in supplying nitric oxide to a subject. Likewise, the present disclosure provides a use of ammonia oxidizing bacteria, e.g., *N. eutropha*, e.g., optionally axenic *N. eutropha* described herein (e.g., strain D23) in the manufacture of a medicament or composition suitable for position in close proximity to a subject.

The present disclosure also provides a method of reducing body odor, comprising topically administering to a subject in need thereof an effective dose of ammonia oxidizing bacteria, e.g., *N. eutropha*, e.g., optionally axenic *N. eutropha* described herein (e.g., strain D23). Similarly, the present disclosure provides ammonia oxidizing bacteria, e.g., *N. eutropha*, e.g., optionally axenic *N. eutropha* described herein (e.g., strain D23) for use in reducing body odor in a subject. Likewise, the present disclosure provides a use of ammonia oxidizing bacteria, e.g., *N. eutropha*, e.g., optionally axenic *N. eutropha* described herein (e.g., strain D23) in the manufacture of a medicament or composition for reducing body odor.

The present disclosure also provides a method of treating or preventing a disease associated with low nitrite levels, comprising topically administering to a subject in need thereof a therapeutically effective dose of ammonia oxidizing bacteria, e.g., *N. eutropha*, e.g., optionally axenic *N. eutropha* described herein (e.g., strain D23). Similarly, the present disclosure provides a topical formulation of ammonia oxidizing bacteria, e.g., *N. eutropha*, e.g., optionally axenic *N. eutropha* described herein (e.g., strain D23) for use in treating a disease associated with low nitrite levels. Likewise, the present disclosure provides a use of ammonia oxidizing bacteria, e.g., *N. eutropha*, e.g., optionally axenic *N. eutropha* described herein (e.g., strain D23) in the manufacture of a topical medicament for treating a disease associated with low nitrite levels.

The present disclosure also provides a method of treating or preventing a skin disorder or skin infection, comprising topically administering to a subject in need thereof a therapeutically effective dose of ammonia oxidizing bacteria, e.g., *N. eutropha*, e.g., optionally axenic *N. eutropha* described herein (e.g., strain D23). Similarly, the present disclosure provides ammonia oxidizing bacteria, e.g., *N. eutropha*, e.g., optionally axenic *N. eutropha* described herein (e.g., strain D23) for use in treating a skin disorder in a subject. Likewise, the present disclosure provides a use of ammonia oxidizing bacteria, e.g., *N. eutropha*, e.g., optionally axenic *N. eutropha* described herein (e.g., strain D23) in the manufacture of a medicament for treating skin disorder. In embodiments, the skin disorder is acne, rosacea, eczema, psoriasis, or urticaria; the skin infection is impetigo.

While not wishing to be bound by theory, it is proposed that treatment of acne with a therapeutically effective dose of optionally axenic *N. eutropha* bacteria as described herein (e.g., strain D23) may involve the downregulation of inflammation due to NO generation; and/or limiting and/or inhibiting the spread and proliferation of *Propionibacterium acnes* associated with acne vulgaris through acidified nitrite and NO production.

For instance, the disclosure provides uses, for treating a condition or disease (e.g., inhibiting microbial growth on a subject's skin), a composition of ammonia oxidizing bacteria. In embodiments, the ammonia oxidizing bacteria may be used to treat, e.g., chronic wounds, acne, rosacea, eczema, psoriasis, uticaria, or skin infections.

The systems and methods of the present disclosure may provide for, or contain contents, to be useful for treating or preventing a skin disorder, treating or preventing a disease or condition associated with low nitrite levels, a treating or preventing body odor, treating to supply nitric oxide to a subject, or treating to inhibit microbial growth.

The systems and methods of the present disclosure may provide for reducing an amount of undesirable bacteria from an environment, e.g., a surface of a subject.

The systems and methods of the present disclosure may provide for, or contain contents, to be useful in a treatment of at least one of acne, eczema, psoriasis, uticaria, rosacea, skin infections and wounds, e.g., an infected wound.

In some embodiments, ammonia oxidizing bacteria may be used to treat a subject. Subjects may include an animal, a mammal, a human, a non-human animal, a livestock animal, or a companion animal.

In some embodiments, ammonia oxidizing bacteria described herein are used to inhibit the growth of other organisms. For instance, ammonia oxidizing bacteria may be well-adapted for long-term colonization of human skin, and in some embodiments it out-competes other bacteria that are undesirable on the skin. Undesirable skin bacteria include, e.g., those that can infect wounds, raise the risk or severity of a disease, or produce odors. Undesirable bacteria may be referred to as pathogenic bacteria. Certain undesirable skin bacteria include *Staphylococcus aureus* (*S. aureus*), e.g., methicillin resistant *Staphylococcus aureus Pseudomonas aeruginosa* (*P. aeruginosa*), *Streptococcus pyogenes* (*S. pyogenes*), *Acinetobacter baumannii* (*A. baumannii*), Propionibacteria, and *Stenotrophomonas*. The ammonia oxidizing bacteria described herein may out-compete other organisms by, e.g., consuming scarce nutrients, or generating byproducts that are harmful to other organisms, e.g., changing the pH of the skin to a level that is not conducive to the undesirable organism's growth.

Accordingly, the present disclosure provides, inter alia, a method of inhibiting microbial growth on a subject's skin, comprising topically administering to a human in need thereof an effective dose of ammonia oxidizing bacteria as described herein. Similarly, the present disclosure provides ammonia oxidizing bacteria as described herein for use in inhibiting microbial growth on a subject's skin. Likewise, the present disclosure provides a use of ammonia oxidizing bacteria in the manufacture of a medicament for inhibiting microbial growth on a subject's skin.

The present disclosure provides, inter alia, a method of changing a composition of a skin microbiome, e.g., modulating a composition of a skin microbiome, e.g., modulating or changing the proportions of the skin microbiome, in an environment, e.g., a surface, e.g., a surface of a subject. The method may comprise administering, e.g., applying, a preparation comprising ammonia oxidizing bacteria to an environment, e.g., a surface, e.g., a surface of a subject. In some embodiments, the amount and frequency of administration, e.g., application, may be sufficient to reduce the proportion of pathogenic bacteria on the surface of the skin. In some embodiments, the subject may be selected on the basis of the subject being in need of a reduction in the proportion of pathogenic bacteria on the surface of the skin.

The present disclosure may further provide obtaining a sample from the surface of the skin, and isolating DNA of bacteria in the sample. Sequencing of the DNA of bacteria in the sample may also be performed to determine or monitor the amount or proportion of bacteria in a sample of a subject.

The present disclosure may also provide for increasing the proportion of non-pathogenic bacteria on the surface. In some embodiments, the non-pathogenic bacteria may be commensal non-pathogenic bacteria. In some embodiments, the non-pathogenic bacteria may be of the *Staphylococcus* genus. In some embodiments, the non-pathogenic bacteria may be *Staphylococcus epidermidis*. In some embodiments, the non-pathogenic bacteria that is increased in proportion may be of the *Staphylococcus* genus, comprising at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% *Staphylococcus epidermidis*.

The increase in the proportion of non-pathogenic bacteria may occur with a pre-determined period of time, e.g., in less than 1 day, 2 days, 3 days, 4 days, 5 days, 1 week, 2 weeks, 3 weeks, or 4 weeks, or in less than 1-3, 3-5, 5-7, 7-9, 5-10, 10-14, 12-18, 12-21, 21-28, 28-35, 35-42, 42-49, 49-56, 46-63, 63-70, 70-77, 77-84, 84-91 days.

The increase in the proportion of *Staphylococcus* bacteria, e.g., *Staphylococcus epidermidis*, may be observed in less than about 3 weeks, e.g., about 16 days, e.g., about 2 weeks.

The present disclosure may provide for decreasing the proportion of pathogenic bacteria, e.g., potentially pathogenic bacteria, e.g., disease-associated bacteria on the surface. In some embodiments, the pathogenic bacteria may be Propionibacteria. In some embodiments, the pathogenic bacteria may be *Stenotrophomonas*.

The decrease in the proportion of pathogenic bacteria may occur with a pre-determined period of time, e.g., in less than 1 day, 2 days, 3 days, 4 days, 5 days, 1 week, 2 weeks, 3 weeks, or 4 weeks, or in less than 1-3, 3-5, 5-7, 7-9, 5-10, 10-14, 12-18, 12-21, 21-28, 28-35, 35-42, 42-49, 49-56, 46-63, 63-70, 70-77, 77-84, 84-91 days.

The decrease in the proportion of Propionibacteria bacteria and/or *Stenotrophomonas* may be observed in less than about 3 weeks, e.g., about 16 days, e.g., about 2 weeks.

The present disclosure also provides a method of supplying nitric oxide to a subject, comprising positioning an effective dose of ammonia oxidizing bacteria described herein in close proximity to the subject. Similarly, the present disclosure provides ammonia oxidizing bacteria as described herein for use in supplying nitric oxide to a subject. Likewise, the present disclosure provides a use of in the manufacture of a medicament or composition suitable for position in close proximity to a subject.

The present disclosure also provides a method of reducing body odor, comprising topically administering to a subject in need thereof an effective dose of ammonia oxidizing bacteria described herein. Similarly, the present disclosure provides ammonia oxidizing bacteria as described herein for use in reducing body odor in a subject. Likewise, the present disclosure provides a use of ammonia oxidizing bacteria as described herein in the manufacture of a medicament or composition for reducing body odor.

The present disclosure also provides a method of treating or preventing a disease associated with low nitrite levels, comprising topically administering to a subject in need thereof a therapeutically effective dose of ammonia oxidizing bacteria described herein. Similarly, the present disclosure provides a topical formulation of ammonia oxidizing bacteria as described herein for use in treating a disease associated with low nitrite levels. Likewise, the present disclosure provides a use of ammonia oxidizing bacteria as described herein in the manufacture of a topical medicament for treating a disease associated with low nitrite levels.

The present disclosure also provides a method of treating or preventing a skin disorder or skin infection, comprising topically administering to a subject in need thereof a therapeutically effective dose of ammonia oxidizing bacteria as described herein. Similarly, the present disclosure provides ammonia oxidizing bacteria as described herein for use in treating a skin disorder in a subject. Likewise, the present disclosure provides a use of ammonia oxidizing bacteria as described herein in the manufacture of a medicament for treating skin disorder. In embodiments, the skin disorder is acne, rosacea, eczema, psoriasis, or urticaria; the skin infection is impetigo.

While not wishing to be bound by theory, it is proposed that treatment of rosacea with a therapeutically effective dose of a therapeutically effective dose of ammonia oxidizing bacteria, e.g., optionally axenic *N. eutropha* bacteria as described herein (e.g., strain D23) may involve downregulation due to NO generation. This may be due to expression of Kazal-type KLK5/KLK7 inhibitor(s) that may reduce formation of the human cathelicidin peptide LL-37 from its precursor propeptide hCAP18.

While not wishing to be bound by theory, it is proposed that treatment of eczema and/or atopic dermatitis with a therapeutically effective dose of ammonia oxidizing bacteria, e.g., optionally axenic *N. eutropha* bacteria as described herein (e.g., strain D23) may involve downregulation of inflammation due to NO generation; and/or limiting and/or inhibiting the spread and proliferation of *S. aureus* and other skin pathogens often associated with very high colonization rates and skin loads in atopic dermatitis through acidified nitrite and NO production.

While not wishing to be bound by theory, it is proposed that treatment of psoriasis with a therapeutically effective dose of ammonia oxidizing bacteria, e.g., optionally axenic *N. eutropha* bacteria as described herein (e.g., strain D23) may involve downregulation of inflammation due to NO generation and reduction in formation of human cathelicidin peptide LL-37.

While not wishing to be bound by theory, it is proposed that treatment of psoriasis with a therapeutically effective dose of ammonia oxidizing bacteria, e.g., optionally axenic *N. eutropha* bacteria as described herein (e.g., strain D23) may involve downregulation of inflammation due to NO generation.

While not wishing to be bound by theory, it is proposed that treatment of impetigo or other skin and soft tissue infections with a therapeutically effective dose of ammonia oxidizing bacteria, e.g., optionally axenic *N. eutropha* bacteria as described herein (e.g., strain D23) may involve limiting and/or inhibiting the spread and proliferation of *S. aureus* and *S. pyogenes*.

The present disclosure also provides a method of promoting wound healing, comprising administering to a wound an effective dose of ammonia oxidizing bacteria, e.g., optionally axenic *N. eutropha* bacteria as described herein (e.g., strain D23). Similarly, the present disclosure provides ammonia oxidizing bacteria, e.g., optionally axenic *N. eutropha* as described herein (e.g., strain D23) for use in treating a wound. Likewise, the present disclosure provides a use of ammonia oxidizing bacteria, e.g., optionally axenic *N. eutropha* as described herein (e.g., strain D23) in the manufacture of a medicament or a composition for treating a wound.

Ammonia oxidizing bacteria, e.g., optionally axenic *N. eutropha* as described herein (e.g., strain D23) may be used to promote wound healing in a patient that has an impaired healing ability, e.g., a diabetic patient.

In some embodiments, this disclosure provides methods of using ammonia oxidizing bacteria, e.g., optionally axenic *N. eutropha* as described herein (e.g., strain D23) to prevent a disease or disorder, e.g., a skin disorder. Prevention, in certain embodiments, means reducing the risk of a subject developing a disease, compared to a similar untreated subject. The risk need not be reduced to zero.

In some embodiments, the present disclosure provides a method of treating a wound by applying a bandage comprising *N. eutropha* to the wound. Also provided are methods of producing such a bandage. The bandage may comprise, for example, an adhesive portion to affix the bandage to undamaged skin near the wound and a soft, flexible portion to cover or overlay the wound. In some embodiments, the bandage contains no other organisms but *N. eutropha*. The bandage may be made of a permeable material that allows gasses like oxygen and carbon dioxide to reach the *N. eutropha* when the bandage is applied to the wound. In certain embodiments, the bandage comprises nutrients for *N. eutropha* such as ammonium, ammonia, urea, or trace minerals. In certain embodiments, the bandage comprises an antibiotic to which the *N. eutropha* is resistant. The antibiotic resistance may arise from one or more endogenous resistance gene or from one or more transgenic.

In some embodiments, the ammonia oxidizing bacteria, e.g., *N. eutropha* is administered at a dose of about $10^8$-$10^9$ CFU, $10^9$-$10^{10}$ CFU, $10^{10}$-$10^{11}$ CFU, or $10^{11}$-$10^{12}$ CFU per application. In some embodiments, the ammonia oxidizing bacteria, e.g., *N. eutropha* is administered topically at a dose of about $10^{10}$-$10^{11}$ CFU, e.g., about $1\times10^{10}$-$5\times10^{10}$, $1\times10^{10}$-$3\times10^{10}$, or $1\times10^{10}$-$2\times10^{10}$ CFU. In some embodiments, the ammonia oxidizing bacteria, e.g., *N. eutropha* is administered topically at a dose of about $2\times10^9$, $4\times10^9$ or $8\times10^9$ CFU.

In some embodiments, the ammonia oxidizing bacteria, e.g., *N. eutropha* is administered in a volume of about 1-2, 2-5, 5-10, 10-15, 12-18, 15-20, 20-25, or 25-50 ml per dose. In some embodiments, the solution is at a concentration of about $10^8$-$10^9$, $10^9$-$10^{10}$, or $10^{10}$-$10^{11}$ CFUs/ml. In some embodiments, the ammonia oxidizing bacteria, e.g., *N. eutropha* is administered as two 15 ml doses per day, where each dose is at a concentration of $10^9$ CFU/ml. In some embodiments, the ammonia oxidizing bacteria, e.g., *N. eutropha* is administered at a concentration of $2\times10^9$, $4\times10^9$ or $8\times10^9$ CFU/L. In some embodiments, the ammonia oxidizing bacteria, e.g., *N. eutropha* is administered at a concentration of $2\times10^9$, $4\times10^9$ or $8\times10^9$ CFU/mL.

In some embodiments, the preparation of ammonia oxidizing bacteria may comprise an ammonia oxidizing bacteria having a dose as described herein, in combination with ammonia, for example, an ammonia concentration of between about 0.01 mM to about 100 mM. For example, the ammonia concentration may be about 0.01, 0.05, 0.1, 0.2, 0.4, 0.5, 0.6, 0.8, 1.0, 1.2, 1.4, 1.6, 1.8, 2.0, 2.2, 2.4, 2.5, 2.6, 2.8, 3.0, 3.2, 3.4, 3.6, 3.8, 4.0, 4.2, 4.4, 4.5, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 10.0, 15.0, 20.0, 25.0, 30.0, 35.0, 40.0, 45.0, 50.0, 55.0, 60.0, 65.0, 70.0, 75.0, 80.0, 85.0, 90.0, 95.0, 100.0 mM.

In some embodiments, ammonia oxidizing bacteria, e.g., the *N. eutropha* is administered once, twice, three, or four times per day. In some embodiments, ammonia oxidizing bacteria, e.g., the *N. eutropha* is administered once, twice, three, four, five, or six times per week. In some embodiments, ammonia oxidizing bacteria, e.g., the *N. eutropha* is administered shortly after bathing. In some embodiments, ammonia oxidizing bacteria, e.g., the *N. eutropha* is administered shortly before sleep.

In certain aspects, the present disclosure provides combination therapies comprising ammonia oxidizing bacteria, e.g., a *N. eutropha* and a second therapeutic. For instance, the disclosure provides physical admixtures of the two (or more) therapies are physically admixed. In other embodiments, the two (or more) therapies are administered in combination as separate formulation. The second therapy may be, e.g., a pharmaceutical agent, surgery, or any other medical approach that treats the relevant disease or disorder. The following paragraphs describe combination therapies capable of chronic wounds, acne, rosacea, eczema, and psoriasis.

In a combination therapy capable of treating chronic wounds, the second therapy may comprise, e.g., an antibiotic (e.g., topical or systemic, and bacteriocidal or bacteriostatic) such as Penicillins, cephalosporins, polymyxins, rifamycins, lipiarmycins, quinolones, sulfonamides, macrolides, lincosamides, tetracyclines, cyclic lipopeptides, glycylcyclines, oxazolidinones, and lipiarmycins; angiotensin, angiotensin analogues; debridement; drainage; wound irrigation; negative pressure wound therapy; application of heat; arterial revascularization; hyperbaric oxygen therapy; antioxidants such as ascorbic acid, glutathione, lipoic acid, carotenes, α-tocopherol, or ubiquinol; low level laser therapy; gastrocnemius recession; growth factors such as vascular endothelial growth factor, insulin-like growth factor 1-2, platelet derived growth factor, transforming growth factor-β, or epidermal growth factor; application of autologous platelets such as those that secrete one or more growth factors such as vascular endothelial growth factor, insulin-like growth factor 1-2, platelet derived growth factor, transforming growth factor-β, or epidermal growth factor; implantation of cultured keratinocytes; allograft; collagen, for instance a dressing comprising collagen; or protease inhibitors such as SLPI. The combination therapy may comprise one or more of the above-mentioned treatments.

In a combination therapy capable of treating acne, the second therapy may comprise, e.g., a medication (e.g., systemic or topical) such as Benzoyl peroxide, antibiotics (such as erythromycin, clindamycin, or a tetracycline), Salicylic acid, hormones (e.g., comprising a progestin such as desogestrel, norgestimate or drospirenone), retinoids such as tretinoin, adapalene, tazarotene, or isotretinoin. The second therapy may also be a procedure such as comedo extraction, corticosteroid injection, or surgical lancing. The combination therapy may comprise one or more of the above-mentioned treatments. The combination therapy may comprise one or more of the therapies described in Table 1, above, for example an acne treatment selected from the group consisting of a topical retinoid, azaelaic acid, salicylic acid, a topical antimicrobial, an oral antibiotic, benzoyl peroxide, an oral anti-androgen, an oral isotretinoin, and combinations thereof.

For instance, the disclosure provides physical admixtures of the two (or more) therapies are physically admixed. In other embodiments, the two (or more) therapies are administered in combination as separate formulation. The therapies may be administered as "simultaneous" or "concomitant" or "concurrent delivery". In other embodiments, the delivery of one treatment ends before the delivery of the other treatment begins. This is sometimes referred to herein as "successive" or "sequential delivery." The beginning of the treatments or therapies may begin before or after diagnosis of a subject as having a skin condition or disorder. The beginning of treatment with ammonia oxidizing bacteria may begin where there has been insufficient response to another treatment. The method may comprise discontinuing use of the other treatment, and/or continuing use of the other treatment, in conjunction with beginning administration of ammonia oxidizing bacteria.

The therapy, e.g., acne treatment such as those listed in Table 1, above, may be administered for a period of time prior to commencing administration of the ammonia oxidizing bacteria. The therapy, e.g., acne treatment such as those listed in Table 1, above may be continued throughout a time period for administration of the ammonia oxidizing bacteria. In certain embodiments, the therapy, e.g., acne treatment such as those listed in Table 1, above, may be ceased during the administration of the ammonia oxidizing bacteria. The therapy, e.g., acne treatment such as those listed in Table 1, above, may be continued throughout administration of the ammonia oxidizing bacteria. The therapy, e.g., acne treatment such as those listed in Table 1, above, may be commenced subsequent to ceasing administration of ammonia oxidizing bacteria.

In a combination therapy capable of treating rosacea, the second therapy may comprise, e.g., an antibiotic, e.g., an oral tetracycline antibiotic such as tetracycline, doxycycline, or minocycline, or a topical antibiotic such as metronidazole; azelaic acid; alpha-hydroxy acid; isotretinoin can be prescribed; sandalwood oil; clonidine; beta-blockers such as nadolol and propranolol; antihistamines (such as loratadine); mirtazapine; methylsulfonylmethane or silymarin, optionally in combination with each other; lasers such as dermatological vascular laser or $CO_2$ laser; or light therapies such as intense pulsed light, low-level light therapy or photorejuvenation. The combination therapy may comprise one or more of the above-mentioned treatments.

In a combination therapy capable of treating eczema, the second therapy may comprise, e.g., a corticosteroid such as hydrocortisone or clobetasol propionate, immunosuppressants (topical or systemic) such as pimecrolimus, tacrolimus, ciclosporin, azathioprine or methotrexate, or light therapy such as with ultraviolet light. The combination therapy may comprise one or more of the above-mentioned treatments.

In a combination therapy capable of treating psoriasis, the second therapy may comprise, e.g., a corticosteroid such as desoximetasone; a retinoid; coal tar; Vitamin D or an analogue thereof such as paricalcitol or calcipotriol; moisturizers and emollients such as mineral oil, vaseline, calcipotriol, decubal, or coconut oil; dithranol; or fluocinonide. The combination therapy may comprise one or more of the above-mentioned treatments.

While not wishing to be bound by theory, it is proposed that treatment of psoriasis with a therapeutically effective dose of ammonia oxidizing bacteria described herein may involve downregulation of inflammation due to NO generation and reduction in formation of human cathelicidin peptide LL-37.

While not wishing to be bound by theory, it is proposed that treatment of psoriasis with a therapeutically effective dose of ammonia oxidizing bacteria as described herein may involve downregulation of inflammation due to NO generation.

While not wishing to be bound by theory, it is proposed that treatment of impetigo or other skin and soft tissue infections with a therapeutically effective dose of ammonia oxidizing bacteria as described herein may involve limiting and/or inhibiting the spread and proliferation of *Staphylococcus aureus* (*S. aureus*), e.g., methicillin resistant *Staphylococcus aureus*, *Pseudomonas aeruginosa* (*P. aeruginosa*), *Streptococcus pyogenes* (*S. pyogenes*), *Acinetobacter baumannii* (*A. baumannii*), Propionibacteria, and *Stenotrophomonas*.

The present disclosure also provides a method of promoting wound healing, comprising administering to a wound an effective dose of ammonia oxidizing bacteria as described herein. Similarly, the present disclosure provides ammonia oxidizing bacteria as described herein for use in treating a wound. Likewise, the present disclosure provides a use of ammonia oxidizing bacteria as described herein in the manufacture of a medicament or a composition for treating a wound.

In some embodiments, this disclosure provides methods of using ammonia oxidizing bacteria as described herein to prevent a disease or disorder, e.g., a skin disorder. Prevention, in certain embodiments, means reducing the risk of a subject developing a disease, compared to a similar untreated subject. The risk need not be reduced to zero.

Individuals having a reduced bathing frequency, such as astronauts, submarine crew members, military personnel during a campaign, civilian workers in remote locations, refugees, bedridden individuals and many others may maintain healthier skin by maintaining ammonia oxidizing bacteria on the skin. With regard to bedridden individuals, the ammonia oxidizing bacteria in some embodiments reduces the frequency or severity of bed sores by augmenting inadequate circulation.

It is appreciated that many modern degenerative diseases may be caused by a lack of NO species, and that ammonia oxidizing bacteria on the external skin can supply those species by diffusion, and that application of ammonia oxidizing bacteria to the skin resolves long standing medical conditions. In certain embodiments, ammonia oxidizing bacteria are applied to a subject to offset modern bathing practices, especially with anionic detergents remove ammonia oxidizing bacteria from the external skin.

One suitable method of topical application to apply sufficient ammonia oxidizing bacteria and then wear sufficient clothing so as to induce sweating. However, many people will want to derive the benefits of ammonia oxidizing bacteria while maintaining their current bathing habits, in which case, a culture of the bacteria can be applied along with sufficient substrate for them to produce NO. A nutrient solution approximating the inorganic composition of human sweat can be used for this purpose. Using bacteria adapted to media approximating human sweat minimizes the time for them to adapt when applied. Since sweat evaporates once excreted onto the skin surface, using a culture media that has a higher ionic strength is desirable. A concentration approximately twice that of human sweat is suitable, but other conditions are also contemplated. Ammonia oxidizing bacteria's nutritional needs are typically met with $NH_3$ or urea, $O_2$, $CO_2$, and minerals. In some embodiments, the substrate comprises trace minerals including iron, copper, zinc, cobalt, molybdenum, manganese, sodium, potassium, calcium, magnesium, chloride, phosphate, sulfate, or any combination thereof.

In some embodiments, the present disclosure provides a method of treating a wound by applying a bandage comprising ammonia oxidizing bacteria to the wound. Also provided are methods of producing such a bandage. The bandage may comprise, for example, an adhesive portion to affix the bandage to undamaged skin near the wound and a soft, flexible portion to cover or overlay the wound. In some embodiments, the bandage contains no other organisms but ammonia oxidizing bacteria. The bandage may made of a permeable material that allows gasses like oxygen and carbon dioxide to reach the ammonia oxidizing bacteria when the bandage is applied to the wound. In certain embodiments, the bandage comprises nutrients for ammonia oxidizing bacteria such as ammonium, ammonia, urea, or trace minerals. In certain embodiments, the bandage comprises an antibiotic to which the ammonia oxidizing bacteria is resistant. The antibiotic resistance may arise from one or more endogenous resistance gene or from one or more transgenes.

In some embodiments, the ammonia oxidizing bacteria, e.g., a preparation of ammonia oxidizing bacteria, is administered at a dose of about $10^8$-$10^9$ CFU, $10^9$-$10^{10}$ CFU, $10^{10}$-$10^{11}$ CFU, or $10^{11}$-$10^{12}$ CFU per application or per day. In some embodiments, the ammonia oxidizing bacteria is administered topically at a dose of about $10^9$-$10^{10}$ CFU, e.g., about $1\times10^9$-$5\times10^9$, $1\times10^9$-$3\times10^9$, or $1\times10^9$-$10\times10^9$ CFU.

In some embodiments, the ammonia oxidizing bacteria is administered in a volume of about 1-2, 2-5, 5-10, 10-15, 12-18, 15-20, 20-25, or 25-50 ml per dose. In some embodiments, the solution is at a concentration of about $10^8$-$10^9$, $10^9$-$10^{10}$, or $10^{10}$-$10^{11}$ CFU/ml. In some embodiments, the ammonia oxidizing bacteria is administered as two 15 ml doses per day, where each dose is at a concentration of $10^9$ CFU/ml.

In some embodiments, the ammonia oxidizing bacteria is administered once, twice, three, or four times per day. In some embodiments, the ammonia oxidizing bacteria is administered once, twice, three, four, five, or six times per week. In some embodiments, the ammonia oxidizing bacteria is administered shortly after bathing. In some embodiments, the ammonia oxidizing bacteria is administered shortly before sleep.

In some embodiments, the ammonia oxidizing bacteria is administered for about 1-3, 3-5, 5-7, 7-9, 5-10, 10-14, 12-18, 12-21, 21-28, 28-35, 35-42, 42-49, 49-56, 46-63, 63-70, 70-77, 77-84, 84-91 days, e.g., for about 1 month, for about 2 months, for about 3 months. In some embodiments, the ammonia oxidizing bacteria is administered for an indefinite period of time, e.g., greater than one year, greater than 5 years, greater than 10 years, greater than 15 years, greater than 30 years, greater than 50 years, greater than 75 years.

5. Use of Microbiome Compatible Cosmetics, e.g, Cleanser, Shampoo, and/or Conditioner, with Administration of Ammonia Oxidizing Bacteria The systems and methods of the disclosure provide, inter alia, cosmetic products, e.g., finished cosmetic products that may be considered to be "biome-friendly" or "biome-compatible." The systems and methods of the disclosure may provide for use of cosmetic products, e.g., finished cosmetic products, that may be used in combination with bacteria, e.g., non-pathogenic bacteria, e.g., ammonia oxidizing bacteria, which may be used in the form of a preparation or composition to be applied to a subject. Table 4 provides for a list of components, one or more of which may be provided in a preparation or composition and that may provide for a biome-friendly or biome compatible product.

TABLE 4

Potential components of a biome-friendly product.

| Component | Category |
|---|---|
| Decyl glucoside | Surfactant/Cleanser |
| cocamidopropyl betaine (ColaTeric COAB) | Surfactant/Cleanser |
| polyethylene sorbitol ester (e.g., Tween 80) | Surfactant/Cleanser |
| ethoxylated lauryl alcohol (RhodaSurf 6 NAT) | Surfactant/Cleanser |
| sodium laureth sulfate/lauryl glucoside/ cocamidopropyl betaine (Plantapon 611 L UP) | Surfactant/Cleanser |
| sodium laureth sulfate (e.g., RhodaPex ESB 70 NAT) | Surfactant/Cleanser |
| alkyl polyglucoside (e.g., Plantaren 2000 N UP) | Surfactant/Cleanser |
| sodium laureth sulfate (Plantaren 200) | Surfactant/Cleanser |
| Dr. Bronner's Castile soap | Surfactant/Cleanser |
| Dr. Bronner's baby soap | Surfactant/Cleanser |
| Lauramine oxide (ColaLux Lo) | Surfactant/Cleanser |
| sodium dodecyl sulfate (SDS) | Surfactant/Cleanser |
| polysulfonate alkyl polyglucoside (PolySufanate 160 P) | Surfactant/Cleanser |
| sodium lauryl sulfate (Stepanol-WA Extra K) | Surfactant/Cleanser |
| Sodium Laurylglucosides Hydroxypropylsulfonate (Suga ®nate 160NC) | Surfactant/Cleanser (bio-based) |
| lauramidopropyl betaine (Cola ®Teric LMB) | Surfactant/Cleanser |
| Cocamidopropyl hydroxysultaine (Cola ®Teric CBS) | Surfactant/Cleanser |

TABLE 4-continued

Potential components of a biome-friendly product.

| Component | Category |
|---|---|
| disodium cocoamphodiacetate (Cola ®Teric CDCX-LV) | Surfactant/Cleanser |
| sodium laurylglucosides hydroxypropyl phosphate (Suga ®Fax D12). | Surfactant/Cleanser |
| sodium lauroyl methyl isethionate (Iselux ® LQ-CLR-SB) | Surfactant/Cleanser |
| sodium methyl cocoyl taurate (Pureact WS Conc.) | Surfactant/Cleanser |
| Aqua (and) Sodium Lauroyl Methyl Isethionate (and) Cocamidopropyl Betaine (and) Sodium Cocoyl Isethionate (and) Sodium Methyl Oleoyl Taurate (Iselux ©SFS-SB) | Surfactant/Cleanser |
| Coco glucoside (Plantacare 818) | Surfactant/Cleanser (bio-based) |
| Sodium cocoyl-glycinate | Surfactant/Cleanser (bio-based) |
| Caprylic/Capric triglyceride (Myritol) | Conditioner |
| Cationic guar (N-Hance) | Conditioning/ de-tangling |
| Coconut oil | Conditioning |
| Apple saccharides, e.g., *plyrus malus* (apple) fruit extract e.g., *plyrus malus* (apple) fruit extract and glycerin (Botanimoist AMS); | Humectant |
| Hydrolyzed *quinoa* | Moisture binding |
| Hydrolyzed *adansonia digitata* (Baobab) Seed Protein | Softener |
| Hydroxyethylcellulose (Natrosol) | Viscosity modifier |
| Hydroxypropylcellulose (Klucel MCS) | Viscosity modifier/ film former |
| Hydrolyzed soy protein (Soy Tein NPNF) | |
| Natural Rose Hydrosol | Fragrance |
| Natural Rose Water | Fragrance |
| *Damascena* flower water | Fragrance |
| Coco-glucoside and glyceryl oleate (Lamisoft ® PO 65) | Lipid layer enhancer |
| Polysorbate 80 | Emulsifier |
| Citric acid | pH stabilizer |

The cosmetic products that may be used with the present disclosure may be, or include, or be disposed in any one or more of a baby product, e.g., a baby shampoo, a baby lotion, a baby oil, a baby powder, a baby cream; a bath preparation, e.g., a bath oil, a tablet, a salt, a bubble bath, a bath capsule; an eye makeup preparation, e.g., an eyebrow pencil, an eyeliner, an eye shadow, an eye lotion, an eye makeup remover, a mascara; a fragrance preparation, e.g., a colognes, a toilet water, a perfume, a powder (dusting and talcum), a sachet; hair preparations, e.g., hair conditioners, hair sprays, hair straighteners, permanent waves, rinses, shampoos, tonics, dressings, hair grooming aids, wave sets; hair coloring preparations, e.g., hair dyes and colors, hair tints, coloring hair rinses, coloring hair shampoos, hair lighteners with color, hair bleaches; makeup preparations, e.g., face powders, foundations, leg and body paints, lipstick, makeup bases, rouges, makeup fixatives; manicuring preparations, e.g., basecoats and undercoats, cuticle softeners, nail creams and lotions, nail extenders, nail polish and enamel, nail polish and enamel removers; oral hygiene products, e.g., dentrifices, mouthwashes and breath fresheners; bath soaps, e.g., foaming body cleansers, and detergents, deodorants, douches, feminine hygiene deodorants; shaving preparations, e.g., aftershave lotions, beard softeners, talcum, preshave lotions, shaving cream, shaving soap; skin care preparations, e.g., cleansing, depilatories, face and neck, body and hand, foot powders and sprays, moisturizing, night preparations, paste masks, skin fresheners; and suntan preparations, e.g., gels, creams, and liquids, and indoor tanning preparations.

The cosmetic products may comprise any one or more of the ingredients disclosed herein, e.g., the ingredients disclosed in Table 4.

The cosmetic product or finished cosmetic product may comprise, consist essentially or consist of the following composition(s), as shown in Table 5, below:

TABLE 5

| Component | Preferred Concentration | Preferred Concentration Range | Description |
|---|---|---|---|
| Klucel MCS (Hydroxypropyl Cellulose) | 1.5% | 1.0-2.0% | Viscosity Modifier |
| Cocamidopropyl Betaine | 20.0% | 15.0%-30.0% | Cleanser/Surfactant |
| Decyl Glucoside | 7.5% | 0.0-10.0% | Cleanser/Surfactant |
| Botanimoist AMG (Glycerine + Apple extract) | 3.0% | 0.0-4.0% | Humectant |
| Hydrolyzed Baobab Protein | 2.0% | 0.0-4.0% | Skin Conditioner |
| Natural Rose Hydrosol | 10.0% | 0.0-15.0% | Fragrance |

This product may be used as a cosmetic product, e.g., for a shampoo, e.g., for a body wash. The product includes water to make 100%. In some embodiments, the cosmetic product, e.g., shampoo, may or may not contain citric acid, and the citric acid may be needed in cases where pH stabilization is required or desired.

The cosmetic product or finished cosmetic product may comprise, consist essentially or consist of the following composition(s), as shown in Table 6, below:

TABLE 6

| Component | Preferred Concentration | Preferred Concentration Range | Description |
|---|---|---|---|
| Klucel MCS (Hydroxypropyl Cellulose) | 0.25% | 0.10-0.50% | Viscosity modifier |
| Cocamidopropyl betaine | 8.00% | 5.0-12.0% | Cleanser/Surfactant |
| Decyl Glucoside | 4.0% | 0.0-6.0% | Cleanser/Surfactant |
| Botanimoist AMG (Glycerine + Apple extract) | 2.0% | 0.0%-4.0% | Humectant |
| Hydrolyzed *Quinoa* Protein conditioner | 1.0% | 0.0-3.0% | Skin Conditioner |
| Natural Rose Hydrosol | 7.5% | 0.0%-10.0% | Fragrance |
| Citric Acid | Added as needed, usually in very small amounts, for pH stabilization | As needed, usually in very small amounts, for pH stabilization | pH stabilizer |

This product may be used as a cosmetic product, e.g., for a cleanser, e.g., for a body, hands, or face. The product includes water to make 100%. In some embodiments, the cosmetic product, e.g., cleanser, may or may not contain citric acid, and the citric acid may be needed in cases where pH stabilization is required or desired.

Other hydrolyzed protein may be used, and may include, but is not limited to rice, soy baobab, and oat. Other fragrance alternatives may be contemplated.

The finished cosmetic product may have one or more, or all the properties described herein.

Other products are contemplated, including hair and/or skin conditioners that may comprise, consist essentially of, or consist of the following, as shown in Table 7, below:

TABLE 7

| Component | Preferred Concentration | Preferred Concentration Range | Description |
|---|---|---|---|
| Hydroxypropyl cellulose (Klucel MCS) | 1.5% | 0.50-2.50% | Viscosity modifier/film former |
| Cationic guar (N-Hance) | 0.5% | 0.10-1.5% | Conditioning and detangling |
| Coconut oil | 1.0% | 0.0-3.0% | Conditioning |
| Fragrance | As desired | As desired | |

The product includes water to make 100%. In some embodiments, the cosmetic product, e.g., conditioner, may or may not contain citric acid, and may be needed in cases where pH stabilization is required or desired.

6. Mechanism of Therapeutic Benefit

While not wishing to be bound by theory, it is believed that one or more of the following mechanisms contributes to the beneficial effect of ammonia oxidizing bacteria, e.g., *N. eutropha* in treating the diseases and conditions discussed herein. Additional mechanistic details are found in International Application WO/2005/030147, which is herein incorporated by reference in its entirety.

In order to understand the beneficial aspects of these bacteria, it is helpful to understand angiogenesis. All body cells, except those within a few hundred microns of the external air, receive all metabolic oxygen from the blood supply. The oxygen is absorbed by the blood in the lung, is carried by red blood cells as oxygenated hemoglobin to the peripheral tissues, where it is exchanged for carbon dioxide, which is carried back and exhaled from the lung. Oxygen must diffuse from the erythrocyte, through the plasma, through the endothelium and through the various tissues until it reached the mitochondria in the cell which consumes it. The human body contains about 5 liters of blood, so the volume of the circulatory system is small compared to that of the body. Oxygen is not actively transported. It passively diffuses down a concentration gradient from the air to the erythrocyte, from the erythrocyte to the cell, and from the cell to cytochrome oxidase where it is consumed. The concentration of oxygen at the site of consumption is the lowest in the body, and the $O_2$ flux is determined by the diffusion resistance and the concentration gradient. Achieving sufficient oxygen supply to all the peripheral tissues requires exquisite control of capillary size and location. If the spacing between capillaries were increased, achieving the same flux of oxygen would require a larger concentration difference and hence a lower $O_2$ concentration at cytochrome oxidase. With more cells between capillaries, the $O_2$ demand would be greater. If the spacing between capillaries were decreased, there would be less space available for the cells that perform the metabolic function of the organ.

In certain aspects, it is appreciated that NO from ammonia oxidizing bacteria is readily absorbed by the outer skin and converted into S-nitrosothiols since the outer skin is free from hemoglobin. M. Stucker et al. have shown that the external skin receives all of its oxygen from the external air in "The cutaneous uptake of atmospheric oxygen contributes significantly to the oxygen supply of human dermis and epidermis. (Journal of Physiology (2002), 538.3, pp. 985-994.) This is readily apparent, because the external skin can be seen to be essentially erythrocyte free. There is circulation of plasma through these layers because they are living and do require the other nutrients in blood, just not the oxygen. S-nitrosothiols formed are stable, can diffuse throughout the body, and constitute a volume source of authentic NO and a source of NO to transnitrosate protein thiols.

In some aspects, it is appreciated that capillary rarefaction may be one of the first indications of insufficient levels of NO. F. T. Tarek et al. have shown that sparse capillaries, or capillary rarefaction, is commonly seen in people with essential hypertension. (Structural Skin Capillary Rarefaction in Essential Hypertension. Hypertension. 1999; 33:998-1001

A great many conditions are associated with the capillary density becoming sparser. Hypertension is one, and researchers reported that sparse capillaries are also seen in the children of people with essential hypertension, and also in people with diabetes. Significant complications of diabetes are hypertension, diabetic nephropathy, diabetic retinopathy, and diabetic neuropathy. R. Candido et al. have found that the last two conditions are characterized by a reduction in blood flow to the affected areas prior to observed symptoms. (Haemodynamics in microvascular complications in type 1 diabetes. Diabetes Metab Res Rev 2002; 18: 286-304.) Reduced capillary density is associated with obesity, and simple weight loss increases capillary density as shown by A Philip et al. in "Effect of Weight Loss on Muscle Fiber Type, Fiber Size, Capilarity, and Succinate Dehydrogenase Activity in Humans. The Journal of Clinical Endocrinology & Metabolism Vol. 84, No. 11 4185-4190, 1999.

Researchers have shown that in primary Raynaud's phenomena (PRP), the nailfold capillaries are sparser (slightly) than in normal controls, and more abundant than in patients that have progressed to systemic sclerosis (SSc). M. Bukhari, Increased Nailfold Capillary Dimensions In Primary Raynaud's Phenomenon And Systemic Sclerosis. British Journal of Rheumatology, Vol. 24 No 35: 1127-1131, 1996. They found that the capillary density decreased from 35 loops/mm$^2$ (normal controls) to 33 (PRP), to 17 (SSc). The average distance between capillary limbs was 18µ, 18µ, and 30µ for controls, PRP and SSc, respectively.

In certain aspects, it is appreciated that the mechanism that the body normally uses to sense "hypoxia" may affect the body's system that regulates capillary density. According to this aspect of the invention, a significant component of "hypoxia" is sensed, not by a decrease in O2 levels, but rather by an increase in NO levels. Lowering of basal NO levels interferes with this "hypoxia" sensing, and so affects many bodily functions regulated through "hypoxia." For Example, anemia is commonly defined as "not enough hemoglobin," and one consequence of not enough hemoglobin is "hypoxia", which is defined as "not enough oxygen." According to some aspects, these common definitions do not account for the nitric oxide mediated aspects of both conditions.

At rest, acute isovolemic anemia is well tolerated. A ⅔ reduction in hematocrit has minimal effect on venous return PvO2, indicating no reduction in either $O_2$ tension or delivery throughout the entire body. Weiskopf et al. Human cardiovascular and metabolic response to acute, severe isovolemic anemia. JAMA 1998, vol 279, No. 3, 217-221. At 50% reduction (from 140 to 70 g Hb/L), the average PvO2 (over 32 subjects) declined from about 77% to about 74%

(of saturation). The reduction in $O_2$ capacity of the blood is compensated for by vasodilatation and tachycardia with the heart rate increasing from 63 to 85 bpm. That the compensation is effective is readily apparent, however, the mechanism is not. A typical explanation is that "hypoxia" sensors detected "hypoxia" and compensated with vasodilatation and tachycardia. However, there was no "hypoxia" to detect. There was a slight decrease in blood lactate (a marker for anaerobic respiration) from 0.77 to 0.62 mM/L indicating less anaerobic respiration and less "hypoxia." The 3% reduction in venous return PvO2 is the same level of "hypoxia" one would get by ascending 300 meters in altitude (which typically does not produce tachycardia). With the $O_2$ concentration in the venous return staying the same, and the $O_2$ consumption staying the same, there is no place in the body where there is a reduction in $O_2$ concentration. Compensation during isovolemic anemia may not occur because of $O_2$ sensing.

Thus the vasodilatation that is observed in acute isovolemic anemia may be due to the increased NO concentration at the vessel wall. NO mediates dilatation of vessels in response to shear stress and other factors. No change in levels of NO metabolites would be observed, because the production rate of NO is unchanged and continues to equal the destruction rate. The observation of no "hypoxic" compensation with metHb substitution can be understood because metHb binds NO just as Hb does, so there is no NO concentration increase with metHb substitution as there is with Hb withdrawal.

Nitric oxide plays a role in many metabolic pathways. It has been suggested that a basal level of NO exerts a tonal inhibitory response, and that reduction of this basal level leads to a dis-inhibition of those pathways. Zanzinger et al. have reported that NO has been shown to inhibit basal sympathetic tone and attenuate excitatory reflexes. (Inhibition of basal and reflex-mediated sympathetic activity in the RVLM by nitric oxide. Am. J. Physiol. 268 (Regulatory Integrative Comp. Physiol. 37): R958-R962, 1995.)

In some aspects, it is appreciated that one component of a volume source of NO is low molecular weight S-nitrosothiols produced in the erythrocyte free skin from NO produced on the external skin by ammonia oxidizing bacteria. These low molecular weight S-nitrosothiols are stable for long periods, and can diffuse and circulate freely in the plasma. Various enzymes can cleave the NO from various S-nitrosothiols liberating NO at the enzyme site. It is the loss of this volume source of NO from AOB on the skin that leads to disruptions in normal physiology. The advantage to the body of using S-nitrosothiols to generate NO far from a capillary is that $O_2$ is not required for NO production from S-nitrosothiols. Production of NO from nitric oxide synthase (NOS) does require $O_2$. With a sufficient background of S-nitrosothiols, NO can be generated even in anoxic regions. Free NO is not needed either since NO only exerts effects when attached to another molecule, such as the thiol of a cysteine residue or the iron in a heme, so the effects of NO can be mediated by transnitrosation reactions even in the absence of free NO provided that S-nitrosothiols and transnitrosation enzymes are present.

Frank et al. have shown that the angiogenesis that accompanies normal wound healing is produced in part by elevated VEGF which is induced by increased nitric oxide. (Nitric oxide triggers enhanced induction of vascular endothelial growth factor expression in cultured keratinocytes (HaCaT) and during cutaneous wound repair. FASEB J. 13, 2002-2014 (1999).)

NO has a role in the development of cancer, indicating that the bacteria described herein may be used in methods of cancer treatment and prevention. According to certain aspects, it is appreciated that the presence of NO during hypoxia may prevent cells from dividing while under hypoxic stress, when cells are at greater risk for errors in copying DNA. One relevant cell function is the regulation of the cell cycle. This is the regulatory program which controls how and when the cell replicates DNA, assembles it into duplicate chromosomes, and divides. The regulation of the cell cycle is extremely complex, and is not fully understood. However, it is known that there are many points along the path of the cell cycle where the cycle can be arrested and division halted until conditions for doing so have improved. The p53 tumor suppressor protein is a key protein in the regulation of the cell cycle, and it serves to initiate both cell arrest and apoptosis from diverse cell stress signals including DNA damage and p53 is mutated in over half of human cancers as reported by Ashcroft et al. in "Stress Signals Utilize Multiple Pathways To Stabilize p53." (Molecular And Cellular Biology, May 2000, p. 3224-3233.) Hypoxia does initiate accumulation of p53, and while hypoxia is important in regulating the cell cycle, hypoxia alone fails to induce the downstream expression of p53 mRNA effector proteins and so fails to cause arrest of the cell cycle. Goda et al. have reported that hypoxic induction of cell arrest requires hypoxia-inducing factor-1 (HIF-1α). (Hypoxia-Inducible Factor 1α Is Essential for Cell Cycle Arrest during Hypoxia. Molecular And Cellular Biology, January 2003, p. 359-369.) Britta et al. have reported that NO is one of the main stimuli for HIF-1α. (Accumulation of HIF-1a under the influence of nitric oxide. Blood, 15 Feb. 2001, Volume 97, Number 4.) In contrast, NO does cause the accumulation of transcriptionally active p53 and does cause arrest of the cell cycle and does cause apoptosis. Wang et al., P53 Activation By Nitric Oxide Involves Down-Regulation Of Mdm2. THE JOURNAL OF BIOLOGICAL CHEMISTRY Vol. 277, No. 18, Issue Of May 3, Pp. 15697-15702, 2002.

In certain aspect of the invention, it is appreciated that preventing the necrotic death of cells by preventing the capillary rarefaction that leads to their hypoxic death may prevent autoimmune disorders. When cells are exposed to chronic hypoxia, the production of reactive oxygen species (ROS) is increased, and there is increased damage to the cells metabolic machinery and ultimately to the cells' DNA. Decreased metabolic capacity will decrease capacity for repair of damage due to ROS and due to exogenous carcinogen exposure. Over time, the damage accumulates and increases the chance of three events: the cell will undergo deletion of cancer-preventing genes and the cell will become cancerous, the cell will die through necrosis, or the cell will die through apoptosis. When cells die, either through necrosis or apoptosis, the cell debris must be cleared from the site. Dead cells are phagocytosed by immune cells, including dendritic cells and macrophages. When these cells phagocytose a body, it is digested by various proteolytic enzymes into antigenic fragments, and then these antigens are attached to the major histocompatability complex (MHC1, MHC2) and the antigen-MHC complex is moved to the surface of the cell where it can interact with T cells and activate the T cells in various ways. Any cell injury releases adjuvants which stimulate the immune system in various ways. In general, cells that undergo necrosis stimulate a greater immune response than cells that undergo apoptosis. Chronic exposure of immune cells to dead and dying cells is therefore likely to lead to autoimmune disorders.

In certain aspects, it is appreciated that low basal NO leads to fibrotic hypertrophy. Once a dead cell has been cleared, a new cell cannot easily take its place, because there is insufficient $O_2$ to support it. Any such new cell would suffer the same fate. The space can remain empty, in which case the organ shrinks, the capillaries draw closer together, new cells are now deprived of the VEGF formerly produced by the now-missing cell, so capillaries ablate and the hypoxic zone reforms. This could result in a general shrinkage of the affected tissues. In tissues that support fibrosis, relatively inert collagen fibers can fill the space. Since the metabolic requirements of the body for the particular organ in question are not reduced, the organ may attempt to grow larger, but now with a significant fibrous content. This may result in fibrotic hypertrophy, such as of the heart and liver. Some organs, such as the brain, cannot grow larger or smaller because the three-dimensional connectivity of nerves and blood vessels are important, and cannot be continuously and simultaneously mapped onto an asymmetrically shrinking brain. The space must be filled with something, and β-amyloid might be the (not so inert) space filler. The kidney cannot grow larger because of the renal capsule, so the number of living cells becomes smaller and they are replaced with fibrotic tissue. If the dead cells are cleared, the tissue shrinks, and the ratio of $NO/O_2$ goes down again, and the capillaries again become sparser. This may set up the vicious circle of end stage renal disease, congestive heart failure/cardiac hypertrophy, primary biliary cirrhosis, Alzheimer's disease, atherosclerosis, inflammatory bowel disease, hypertrophic scar formation, and the multiple connective tissue diseases starting with Raynaud's phenomena and ending with Systemic Sclerosis and primary Sjogren's syndrome where capillary rarefaction is also observed. Ferrini et al, have shown that a reduction in basal NO levels through chronic inhibition of NOS with L-NAME leads to generalized fibrosis of the heart and kidneys. (Antifibrotic Role of Inducible Nitric Oxide Synthase. Nitirc Oxide: Biology and Chemistry Vol. 6, No. 3, pp. 283-294 (2002).) It may be that low basal NO leads to fibrotic hypertrophy.

In certain aspects, it is appreciated that capillary rarefaction affects a subject's ability to control their appetite. Capillary rarefaction is observed in the brains of aged humans and animals. Capillary rarefaction is associated with declines in circulating growth factors including insulin like growth factor-1. Neurogenesis in the adult brain is coordinated with angiogenesis. Since the brain regulates many homeostatic functions, increased diffusion lengths between capillaries to control elements of the brain might be "interpreted" as inadequate blood concentrations of those species. The flux of glucose in the brain is quite close to normal metabolic needs, where glucose flux is only 50 to 75% greater than glucose consumption and the glucose transporters across the blood brain barrier are saturable, steriospecific and independent of energy or ion gradients. A large part of the regulation of appetite is mediated through the brain, and capillary rarefaction may cause an adequate blood concentration of "nutrients" (or marker compounds proportional to "nutrients") to be interpreted as insufficient. This may be one cause of obesity.

According to certain aspects, it is appreciated that capillary rarefaction may be a cause of non-insulin dependent diabetes. Non-insulin dependent diabetes (NIDDM) is also known as the Metabolic Syndrome or Diabetes type 2, and is characterized by insulin resistance. The sensitivity of the body to insulin is reduced, and insulin levels increase People with NIDDM have high blood glucose, high blood triglycerides, are typically obese, hypertensive, and typically have significant visceral fat.

Other symptoms accompany NIDDM, which may point to capillary rarefaction as the cause. In a study of 40 men, with and without NIDDM, obese (BMI 29) and lean (BMI 24) (10 of each), Konrad et al. report that blood lactate levels at rest were 1.78, 2.26, 2.42, and 2.76 (mM/L) for lean men without, obese men without, lean men with NIDDM, obese men with NIDDM respectively. (A-Lipoic acid treatment decreases serum lactate and pyruvate concentrations and improves glucose effectiveness in lean and obese patients with type 2 diabetes. Diabetes Care 22:280-287, 1999.) Lactate is a measure of anaerobic glycolysis. When $O_2$ is insufficient to generate ATP through oxidative phosphorylation, cells can produce ATP through anaerobic glycolysis. One of the products of anaerobic glycolysis is lactate, which must be exported from the cells, otherwise the pH drops and function is compromised. Blood lactate is commonly measured in exercise studies, where an increase indicates the work load at which maximum oxidative work can be done. Higher levels of lactate at rest would indicate increased anaerobic glycolysis at rest, which is consistent with capillary rarefaction.

Primary biliary cirrhosis is associated with Raynaud's phenomena, pruritus, sicca syndrome, osteoporosis, portal hypertension, neuropathy, and pancreatic insufficiency, and liver abnormalities are associated with rheumatic diseases. Elevated liver enzymes are a symptom of liver inflammation, and elevated liver enzymes are observed as an early symptom of "asymptomatic" primary biliary cirrhosis. Accordingly, the bacteria described herein may be used to treat liver inflammation.

Torre et al have reported that Alzheimer's disease (AD) is a microvascular disorder with neurological degeneration secondary to hypoperfusion, resulting in part from insufficient nitric oxide. (Review: Evidence that Alzheimer's disease is a microvascular disorder: the role of constitutive nitric oxide, Brain Research Reviews 34 (2000) 119-136.) Accordingly, the bacteria described herein may be used to treat AD.

Adverse health effects that are associated with hypertension may also be consequences of low basal NO. The decreased response to vasodilatation is also consistent with low basal NO. NO is a diffusible molecule that diffuses from a source to a sensor site where it has the signaling effect. With low NO levels, every NO source must produce more NO to generate an equivalent NO signal of a certain intensity a certain distance away. NO diffuses in three dimensions and the whole volume within that diffusion range must be raised to the level that will give the proper signal at the sensor location. This may result in higher NO levels at the source and between the source and the sensor. Adverse local effects of elevated NO near a source may then arise from too low a NO background. There is some evidence that this scenario actual occurs. In rat pancreatic islets, Hennings son et al have reported that inhibition of NOS with L-NAME increases total NO production through the induction of iNOS. (Chronic blockade of NO synthase paradoxically increases islet NO production and modulates islet hormone release. Am J Physiol Endocrinol Metab 279: E95-E107, 2000.) Increasing NO by increasing NOS activity will only work up to some limit. When NOS is activated but is not supplied with sufficient tetrahydrobiopterin (BH4) or L-arginine, it becomes "uncoupled" and generates superoxide (O2-) instead of NO. This $O_2^-$ may then destroy NO. Attempting to produce NO at a rate that exceeds the supply of BH4 or L-arginine may instead decrease NO levels. This may result in positive feedback where low NO levels are made worse by stimulation of NOS, and uncoupled NOS generates significant $O_2^-$ which causes local reactive oxygen species (ROS) damage such as is observed in atherosclerosis, end stage renal disease, Alzheimer's, and diabetes.

The bacteria described herein may also be used to delay the signs of aging. Caloric restriction extends lifespan, and Holloszy reported that restricting food intake to 70% of ad lib controls, prolongs life in sedentary rats from 858 to 1,051 days, almost 25%. (Mortality rate and longevity of food restricted exercising male rats: a reevaluation. J. Appl. Physiol. 82(2): 399-403, 1997.) The link between calorie restriction and prolonged life is well established, however, the causal mechanism is not. Lopez-Torres et al. reported that the examination of liver mitochondrial enzymes in rats indicates a reduction in $H_2O_2$ production due to reduced complex I activity associated with calorie restriction. (Influence Of Aging And Long-Term Caloric Restriction On Oxygen Radical Generation And Oxidative DNA Damage In Rat Liver Mitochondria. Free Radical Biology & Medicine Vol. 32 No 9 pp 882-8899, 2002.) $H_2O_2$ is produced by dismutation of $O_2^-$, which is a major ROS produced by the mitochondria during respiration. The main source of $O_2^-$ has been suggested by Kushareva et al. and others to be complex I which catalyzes the NAD/NADH redox couple by reverse flow of electrons from complex III, the site of succinate reduction. The free radical theory, proposed by Beckman, of aging postulates, that free radical damage to cellular DNA, antioxidant systems and DNA repair systems accumulates with age and when critical systems are damaged beyond repair, death ensues. (The Free Radical Theory of Aging Matures. Physiol. Rev. 78: 547-581, 1998.)

As an additional mechanism, NO has been demonstrated by Vasa et al. to activate telomerase and to delay senescence of endothelial cells. (Nitric Oxide Activates Telomerase and Delays Endothelial Cell Senescence. Circ Res. 2000; 87:540-542.) Low basal NO will increase basal metabolic rate by disinhibition of cytochrome oxidase. Increased basal metabolism will also increase cell turn-over and growth rate. Capillary rarefaction, by inducing chronic hypoxia may increase free radical damage and may also increase cell turn-over, and so accelerate aging by both mechanisms.

In some aspects, it is appreciated that autotrophic ammonia-oxidizing bacteria may produce protective aspects for allergies and autoimmune disorders. The best known autoimmune disease is perhaps Diabetes Type 1, which results from the destruction of the insulin producing cells in the pancreas by the immune system. Recurrent pregnancy loss is also associated with autoimmune disorders where the number of positive autoimmune antibodies correlated positively with numbers recurrent pregnancy losses. Systemic Sclerosis, Primary Biliary Cirrhosis, autoimmune hepatitis, and the various rheumatic disorders are other examples of autoimmune disorders. Application of AOB was observed to reduce an allergy, hay fever, as described in WO/2005/030147.

One mechanism by which AOB may exert their protective effect on allergies and autoimmune disorders is through the production of nitric oxide, primarily through the regulatory inhibition of NF-κB and the prevention of activation of immune cells and the induction of inflammatory reactions. NF-κB is a transcription factor that up-regulates gene expression and many of these genes are associated with inflammation and the immune response including genes which cause the release of cytokines, chemokines, and various adhesion factors. These various immune factors cause the migration of immune cells to the site of their release resulting in the inflammation response. Constitutive NO production has been shown to inhibit NF-κB by stabilizing IκBα (an inhibitor of NF-κB) by preventing IκBα degradation.

Administration of an NO donor has been shown by Xu et al. to prevent the development of experimental allergic encephalomyelitis in rats. (SIN-1, a Nitric Oxide Donor, Ameliorates Experimental Allergic Encephalomyelitis in Lewis Rats in the Incipient Phase: The Importance of the Time Window. The Journal of Immunology, 2001, 166: 5810-5816.) In this study, it was demonstrated that administering an NO donor, reduced the infiltration of macrophages into the central nervous system, reduced the proliferation of blood mononuclear cells, and increased apoptosis of blood mononuclear cells. All of these results are expected to reduce the extent and severity of the induced autoimmune response.

Low basal NO may lead to autism via the mechanism that new connections in the brain are insufficiently formed as a result of insufficient basal nitric oxide. While not wishing to be bound in theory, in some embodiments, formation of neural connections is modulated by NO. In these cases, any condition that lowers the range of NO diffusion may decrease the volume size of brain elements that can undergo connections. A brain which developed under conditions of low basal NO levels may be arranged in smaller volume elements because the reduced effective range of NO.

Additional symptoms exhibited in autistic individuals may also point to low NO as a cause, including increased pitch discrimination, gut disturbances, immune system dysfunction, reduced cerebral blood flow, increased glucose consumption of the brain, increased plasma lactate, attachment disorders, and humming. Each of these symptoms may be attributed to a low basal NO level.

Takashi Ohnishi et al. have reported that autistic individuals show decreased blood flow. Takashi Ohnishi et al., Abnormal regional cerebral blood flow in childhood autism. Brain (2000), 123, 1838-1844. J. M. Rumsey et al. have reported that autistic individuals have increased glucose consumption. Rumsey J M, Duara R, Grady C, Rapoport J L, Margolin R A, Rapoport S I, Cutler N R. Brain metabolism in autism. Resting cerebral glucose utilization rates as measured with positron emission tomography. Arch Gen Psychiatry, 1985 May; 42(5):448-55 (abstract). D. C. Chugani has reported that autistic individuals have an increased plasma lactate levels. Chugani D C, et al., Evidence of altered energy metabolism in autistic children. Prog Neuropsychopharmacol Biol Psychiatry. 1999 May; 23(4): 635-41. The occurrence of these effects may be a result of capillary rarefaction in the brain, which may reduce blood flow and $O_2$ supply, such that some of the metabolic load of the brain may be produced through glycolysis instead of oxidative phosphorylation.

Nitric oxide has been demonstrated by B. A. Klyachko et al. to increase the excitability of neurons by increasing the after hyperpolarization through cGMP modification of ion channels. Vitaly A. Klyachko et al., cGMP-mediated facilitation in nerve terminals by enhancement of the spike after hyperpolarization. Neuron, Vol. 31, 1015-1025, Sep. 27, 2001. C. Sandie et al. have shown that inhibition of NOS reduces startle. Carmen Sandi et al., Decreased spontaneous motor activity and startle response in nitric oxide synthase inhibitor-treated rats. European journal of pharmacology 277 (1995) 89-97. Attention-Deficit Hyperactivity Disorder (ADHD) has been modeled using the spontaneously hypertensive rat (SHR) and the Naples high-excitability (NHE)

rat. Both of these models have been shown by Raffaele Aspide et al, to show increased attention deficits during periods of acute NOS inhibition. Raffaele Aspide et al., Non-selective attention and nitric oxide in putative animal models of attention-deficit hyperactivity disorder. Behavioral Brain Research 95 (1998) 123-133. Accordingly, the bacteria herein may be used in the treatment of ADHD.

Inhibition of NOS has also been shown by M. R. Dzoljic to inhibit sleep. M. R. Dzoljic, R. de Vries, R. van Leeuwen. Sleep and nitric oxide: effects of 7-nitro indazole, inhibitor of brain nitric oxide synthase. Brain Research 718 (1996) 145-150. G. Zoccoli has reported that a number of the physiological effects seen during sleep are altered when NOS is inhibited, including rapid eye movement and sleep-wake differences in cerebral circulation. G. Zoccoli, et al., Nitric oxide inhibition abolishes sleep-wake differences in cerebral circulation. Am. J. Physiol. Heart Circ Physiol 280: H2598-2606, 2001. NO donors have been shown by L. Kapas et al. to promote non-REM sleep, however, these increases persisted much longer than the persistence of the NO donor, suggesting perhaps a rebound effect. Levente Kapas et al. Nitric oxide donors SIN-1 and SNAP promote nonrapid-eye-movement sleep in rats. Brain Research Bullitin, vol 41, No 5, pp. 293-298, 1996. M. Rosaria et al., Central NO facilitates both penile erection and yawning. Maria *Rosaria Melis* and Antonio Argiolas. Role of central nitric oxide in the control of penile erection and yawning. Prog Neuro-Psychopharmacol & Biol. Phychiat. 1997, vol 21, pp 899-922. P. Tani et al, have reported that insomnia is a frequent finding in adults with Asperger's. Pekka Tani et al., Insomnia is a frequent finding in adults with Asperger's syndrome. BMC Psychiatry 2003, 3:12. Y. Hoshino has also observed sleep disturbances in autistic children. Hoshino Y, Watanabe H, Yashima Y, Kaneko M, Kumashiro H. An investigation on sleep disturbance of autistic children. Folia Psychiatr Neurol Jpn. 1984; 38(1):45-51. (abstract) K. A. Schreck et al. has observed that the severity of sleep disturbances correlates with severity of autistic symptoms. Schreck K A, et al., Sleep problems as possible predictors of intensified symptoms of autism. Res Dev Disabil. 2004 January-February; 25(1):57-66. (abstract). Accordingly, the bacteria herein may be used in the treatment of insomnia.

W. D. Ratnasooriya et al reported that inhibition of NOS in male rats reduces pre-coital activity, reduces libido, and reduces fertility. W. D. Ratnasooriya et al., Reduction in libido and fertility of male rats by administration of the nitric oxide (NO) synthase inhibitor N-nitro-L-arginine methyl ester. International journal of andrology, 23: 187-191 (2000).

It may be that a number of seemingly disparate disorders, characterized by ATP depletion and eventual organ failure are actually "caused" by nitropenia, caused by a global deficiency in basal nitric oxide. When this occurs in the heart, the result is dilative cardiomyopathy. When this occurs in the brain, the result is white matter hyperintensity, Alzheimer's, vascular depression, vascular dementia, Parkinson's, and the Lewy body dementias. When this occurs in the kidney, the result is end stage renal disease, when this occurs in the liver, the result is primary biliary cirrhosis. When this occurs in muscle, the consequence is fibromyalgia, Gulf War Syndrome, or chronic fatigue syndrome. When this occurs in the bowel, the consequence is ischemic bowel disease. When this occurs in the pancreas, the consequence is first type 2 diabetes, followed by chronic inflammation of the pancreas, followed by autoimmune attack of the pancreas (or pancreatic cancer), followed by type 1 diabetes. When this occurs in the connective tissue, the consequence is systemic sclerosis.

In the remnant kidney model of end stage renal disease, part of the kidney is removed, (either surgically or with a toxin) which increases the metabolic load on the remainder. Superoxide is generated to decrease NO and increase $O_2$ diffusion to the kidney mitochondria. Chronic overload results in progressive kidney capillary rarefaction and progressive kidney failure. In acute kidney failure, putting people in dialysis can give the kidney a "rest", and allows it to recover. In acute renal failure induced by rhabdomyolysis (muscle damage which releases myoglobin into the blood stream) kidney damage is characterized by ischemic damage. Myoglobin scavenges NO, just as hemoglobin does, and would cause vasoconstriction in the kidney leading to ischemia. Myoglobin would also induce local nitropenia and the cascade of events leading to further ATP depletion.

In some aspects, low NO levels lead to reduced mitochondrial biogenesis. Producing the same ATP at a reduced mitochondria density will result in an increase in $O_2$ consumption, or an accelerated basal metabolic rate. An accelerated basal metabolic rate is observed in a number of conditions, including: Sickle cell anemia, Congestive heart failure, Diabetes, Liver Cirrhosis, Crohn's disease, Amyotrophic lateral sclerosis, Obesity, End stage renal disease, Alzheimer's, and chronic obstructive pulmonary disease.

While some increased $O_2$ consumption might be productively used, in many of these conditions uncoupling protein is also up-regulated, indicating that at least part of the increased metabolic rate is due to inefficiency. Conditions where uncoupling protein is known to be up-regulated include obesity and diabetes.

With fewer mitochondria consuming $O_2$ to a lower $O_2$ concentration, the $O_2$ gradient driving $O_2$ diffusion is greater, so the $O_2$ diffusion path length can increase resulting in capillary rarefaction, which is observed in dilative cardiomyopathy, hypertension, diabetes type 2, and renal hypertension.

Copper, either as Cu2+ or as ceruloplasmin (CP) (the main Cu containing serum protein which is present at 0.38 g/L in adult sera and which is 0.32% Cu and contains 94% of the serum copper) catalyzes the formation of S—NO-thiols from NO and thiol containing groups (RSH). The Cu content of plasma is variable and is increased under conditions of infection. Berger et al. reported that the Cu and Zn content of burn-wound exudates is considerable with patients with ⅓ of their skin burned, losing 20 to 40% of normal body Cu and 5 to 10% of Zn content in 7 days. (Cutaneous copper and zinc losses in burns. Burns. 1992 October; 18(5):373-80.) If the patients skin were colonized by AOB, wound exudates which contains urea and Fe, Cu, and Zn that AOB need, would be converted into NO and nitrite, greatly supplementing the local production of NO by iNOS, without consuming resources (such as $O_2$ and L-arginine) in the metabolically challenged wound. A high production of NO and nitrite by AOB on the surface of a wound would be expected to inhibit infection, especially by anaerobic bacteria such as the Clostridia which cause tetanus, gas gangrene, and botulism.

The practice of the present invention may employ, unless otherwise indicated, conventional methods of immunology, molecular biology, and recombinant DNA techniques within the skill of the art. Such techniques are explained fully in the literature. See, e.g., Sambrook, et al. Molecular Cloning: A Laboratory Manual (Current Edition); and Current Protocols in Molecular Biology (F. M. Ausubel, et al. eds., current edition).

7. Adjusting the Skin Microbiome with Ammonia Oxidizing Bacteria

The present disclosure provides for systems and methods for changing the skin microbiome, e.g., the human skin microbiome. The systems and methods may provide treatment of infections or conditions, e.g., related to the skin, e.g., skin infections and/or skin conditions.

Ammonia-oxidizing bacteria (AOB) of the genus *Nitrosomonas* are Gram-negative obligate autotrophic bacteria with a unique capacity to generate nitrite and nitric oxide exclusively from ammonia as an energy source. They are widely present both in soil and water environments and are essential components of environmental nitrification processes. Due to the roles of nitrite and nitric oxide on human skin as important components of several physiological functions, such as vasodilation, skin inflammation and wound healing, these bacteria may have beneficial properties for both healthy and immunopathological skin conditions. These bacteria may be safe for use in humans because they are slow-growing, cannot grow on organic carbon sources, may be sensitive to soaps and antibiotics, and have never been associated with any disease or infection in animals or humans.

Topical application of ammonia oxidizing bacteria to a subject, e.g., a human subject may lead to unexpected changes in the skin microbiome, and more specifically it may lead to increases in the proportion of normal commensal non-pathogenic species and reductions in the proportion of potentially pathogenic, pathogenic, or disease causing organisms.

EXAMPLES

Example 1

Studies with Ammonia-oxidizing Bacteria for the Human Skin: Cosmetic Effects, Safety, Detection and Skin Metagenomics A blinded, placebo-controlled 24 human volunteer study randomized 4:1 AOB to placebo control was performed. Subjects applied a *Nitrosomonas* suspension ($10^9$ CFU/ml, 2 times per day, for a total of $3 \times 10^{10}$ CFU per day) to their face and scalp twice daily for one week and were followed for two additional weeks post-application. Volunteers were instructed to refrain from using hair products during the one-week AOB application as well as the week following application, then returned to regular shampoo use for the third week. Scalp swabs were obtained on Day 0 as baseline controls and on Day 1, 3, 8, 14 and 21 to assess presence/absence of AOB by PCR and 16S rRNA sequencing analyses.

No serious adverse events were associated with AOB application for one week and the product was deemed safe. AOB users reported a clear improvement in skin condition and quality, as indicated by self-assessment reports completed after the seven-day application period. Using AOB-specific PCR analyses of the skin samples, we could demonstrate presence of the bacteria in 83-100% of AOB users during the application period, whereas no AOB were detected in the placebo control samples. All subjects lacked AOB from baseline swabs obtained prior to study initiation, consistent with the predicted sensitivity of these bacteria to soaps and other commercial products. Amplification of the 16S rRNA gene and sequencing of a subset of samples confirmed presence of AOB in corresponding samples and suggested potential trends in modulating the skin microbiome by topical AOB application. In summary, live AOB-based products are safe and could hold great promise as novel self-regulating topical delivery agents of nitrite and nitric oxide to the human skin.

As shown in Table 8, below, the proportion of *Nitrosomonas* (AOB) went up when comparing Day 0 versus Day 8. The proportion of other bacteria, *Propionibacterium*, *Enterobacter*, and *Citrobacter* went down, when comparing Day 0 versus Day 8. The p-values indicated in Table 8 demonstrate that the most significant change between Day 0 and Day 8 was observed with *Nitrosomonas* (AOB) followed by *Propionibacterium*. *Enterobacter* and *Citrobacter* also showed changes between Day 0 and Day 8 to a lesser degree.

TABLE 8

Trends in microbiome composition following AOB application (Day 0 versus Day 8)

| Genus | P-value (unadjusted) | Fold Change | Trend |
|---|---|---|---|
| *Nitrosomonas* (AOB) | 0.0039 | 10.0 | Up |
| *Propionibacterium* | 0.0078 | 0.4 | Down |
| *Enterobacter* | 0.0346 | 0.8 | Down |
| *Citrobacter* | 0.036 | 0.6 | Down |

Example 2

Placebo-Controlled, Double-Blind, Randomized, Multi-Site Cosmetic Trial to Evaluate the Performance and Tolerability of a Cosmetic Product to Improve the Appearance of Oily Skin, Facial Pores, and Other Cosmetic Parameters in Acne Prone Subjects Phase 2b Study:

AO+Mist (preparation of D23 *N. eutropha*) treatment demonstrated strong efficacy signals in both Skindex, Investigator Global Assessment, and inflammatory lesion count (adult cohort).

The AO+Mist preparation used in the Example 2 testing includes ammonia oxidizing bacteria at a concentration of $1 \times 10^9$ CFU/mL in an aqueous buffer solution of 50 mM $Na_2HPO_4$ and 2 mM $MgCl_2$.

In a four week (two weeks treatment, two weeks wash out) randomized (1:1:1:1) double-blinded placebo controlled dose ranging (2, 4, $8 \times 10^9$ CFU) study of B244 (D23 *N. eutropha*) in 36 adults (age 18+) with acne vulgaris. The study is 80% powered to detect a 30% net improvement in IGA (% subjects improving) at week 2 (pooled B244 vs. placebo). The study is also 80% powered to detect a 30% difference ($p<0.05$) in the mean change in lesion count from baseline between the pooled treatment groups and placebo.

A brief summary of the treatment protocol is as follows. Subjects administered ammonia oxidizing bacteria to the face, neck and scalp for a total of four weeks. After the four week time period, discontinuation of application of ammonia oxidizing bacteria occurred for one week. Use of the biome-compatible shampoo and conditioner occurred for the full five weeks. Clinical evaluations were performed at baseline (time 0), week 4 and week 5.

Purpose

This multi-site, double-blind, randomized, 4-week, placebo-controlled cosmetic trial was conducted to assess the overall cosmetic efficacy on skin appearance and tolerance of the AO+Mist mist when used by men and women ages 12-45 with mild to moderate acne prone skin.

Summary

A total of 83 subjects completed the study, with 42 subjects using AO+Mist (*Nitrosomonas eutropha* preparation) and 41 subjects using Placebo. During the course of the study, subjects were assigned to use AO+Mist (*Nitrosomonas eutropha* preparation) or the Placebo according to a predetermined randomization. Subjects applied the test material to the hair, scalp, and face twice per day as directed. Subjects used ("biome-compatible") standardized soap and shampoo as supporting materials, Shampoo (Lot 293178; shown as the "preferred concentration" in Table 5) and Cleanser (Lot 293162; shown as the "preferred concentration" in Table 6), once per day throughout the course of the study. After the 4-week usage phase, subjects discontinued test material use (while still using supporting materials) and participated in a 1-week regression phase. Clinical evaluations were conducted at visit 1 (baseline), visit 2 (week 4), and visit 3 (week 5). Subjects participated in the following procedures at each time point (unless otherwise indicated):

Clinical Grading of Acne

An expert clinical grader evaluated each subject's VISIA and self-photographs for acne conditions post-study.

Acne Counts

An expert clinical grader counted inflammatory lesions (papules, pustules, and cysts/nodules) and non-inflammatory lesions (open and closed comedones) on each subject's forehead, left cheek, chin, and right cheek (separately).

Investigator's Global Improvement Assessment (IGIA)

The Investigator or designee performed a global acne assessment of the face at week 4 and week 5. A description of IGA may be found through the U.S. Food and Drug Administration, e.g., at http://www.fda.gov/downloads/Drugs/ . . . /Guidances/UCM071292.pdf: Guidance for Industry; Acne Vulgaris: Developing Drugs for Treatment (U.S. Department of Health and Human Services; Food and Drug Administration; Center for Drug Evaluation and Research (CDER); September 2005, Clinical/Medical PIH/PIE Lesion Grading Post-inflammatory hyperpigmentation/post-inflammatory erythema (PIH/PIE) lesions were selected for each subject and an expert clinical grader graded selected PIH/PIE lesions for darkness and size.

Imaging Procedures

Digital images were taken of each subject's face (right side, left side, and center view) using the VISTA CR photo-station (Canfield Imaging Systems, Fairfield, N.J.) with a Canon Mark II 5D digital SLR camera (Canon Incorporated, Tokyo, Japan) using standard 1 and 2, cross-polarized, parallel polarized, and UV-NF lighting conditions. The digital images using cross-polarized lighting were analyzed for pores.

Survey and Self-Photographs

Subjects took weekly standardized self-photographs ("selfies") using their smart phone and completed questionnaires.

Tolerability Evaluations

An expert clinical grader evaluated each subject's global face for objective irritation parameters (erythema, edema, and scaling) and subjects reported the degree of subjective irritation parameters (stinging, burning, and itching).

Clinical Grading of Cosmetic Efficacy Parameters

An expert clinical grader evaluated each subject's face for oily appearance (shine and feel), pore appearance, radiance, blotchiness, skin tone (color) evenness, visual smoothness, and tactile smoothness.

Sebumeter Measurements

Triplicate Sebumeter SM 815 (Courage+Khazaka, Germany) measurements were taken on the forehead to measure sebum quantity on the skin using a photometric method.

Microbiome Sample Collections

Microbiome samples were collected on the back of the neck, behind the right ear, and right cheek (1 from each location).

Overall Conclusions

Overall results from this multi-site, double-blind, randomized, 4-week, placebo-controlled cosmetic trial indicate that use of the test material, AO+Mist (*Nitrosomonas eutropha* preparation), was demonstrated to be safe and effective in subjects with mild and moderate acne conditions. The severity of disease and the count of inflammatory lesions in adults were shown to have improved with AO+Mist treatment. The use of AO+Mist (*Nitrosomonas eutropha* preparation), was very well tolerated by subjects with no statistically significant increase (worsening) in clinical grading scores for erythema, scaling, edema, burning, stinging, and itching at weeks 4 when compared with baseline scores.

The study used the standard FDA Investigator's Global Acne (IGA) scale[1] to assess acne conditions using VISIA images under completely blinded condition. Subjects who used AO+Mist (*Nitrosomonas eutropha* preparation) showed a statistically significant decrease (improvement) in IGA scores at weeks 4 and 5 when compared with baseline scores. Comparisons between the test materials based on the change from baseline indicated a statistically significant difference for acne grading at week 4, in favor of AO+Mist (*Nitrosomonas eutropha* preparation).

Figure 4:
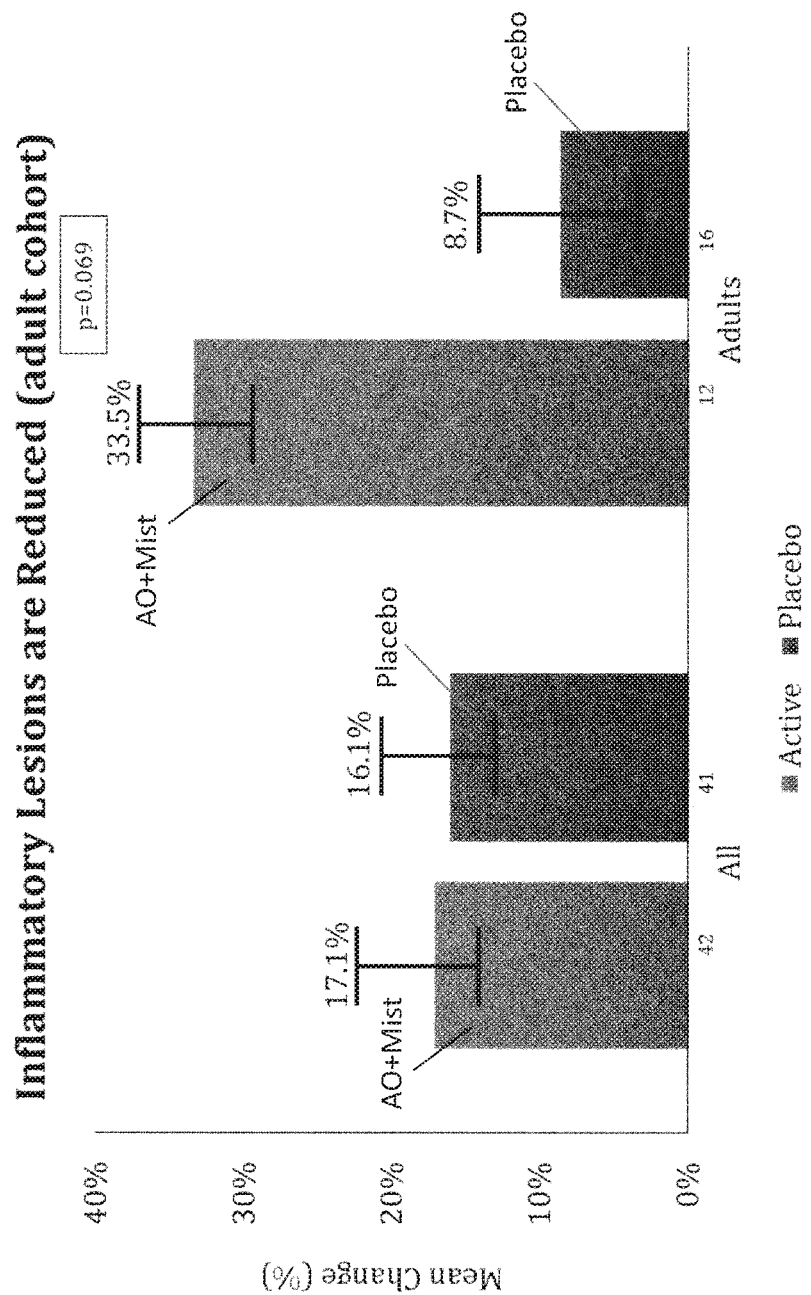
FIG. 4 shows reduction in inflammatory lesions. Mean change (%) is plotted for all test subjects and adult test subjects for ammonia oxidizing bacteria (AO+Mist) and Placebo.

Results of the acne counts for use of AO+Mist (*Nitrosomonas eutropha* preparation) showed a statistically significant decrease (improvement) in papules and inflammatory lesion counts at weeks 4 and 5, and global lesion counts at week 4 when compared with baseline counts. Although no statistically significant difference was observed between AO+Mist (*Nitrosomonas eutropha* preparation) and placebo, the data indicated a greater and more sustained reduction in inflammatory lesion count in adult subjects who used AO+Mist (*Nitrosomonas eutropha* preparation), as shown in FIG. 4. The AO+Mist bars depicted on the graph are the first (from the left) and third (from the left). The Placebo bars depicted on the graph are the second (from the left) and fourth (from the left).

Subject-reported outcomes were measured using the Skindex16 Quality-of-Life survey. AO+Mist was associated with changes (improvements) in the group of questions that captured the subjects' emotional assessment of their disease. Specifically, statistically significant improvements were observed, in favor of AO+Mist (*Nitrosomonas eutropha* preparation), for skin condition hurting (week 2), persistence/reoccurrence of skin condition (week 4), worry about skin condition (week 5), and appearance of skin condition (weeks 2, 4, and 5).

Results of clinical grading for use of AO+Mist (*Nitrosomonas eutropha* preparation) showed a statistically significant decrease (improvement) in clinical grading scores for visual and tactile smoothness at weeks 4 and 5, and for blotchiness at week 5, when compared with baseline scores.

Test Material Descriptions

Table 9 and Table 10 present the descriptions of each test material and supporting material.

TABLE 9

TEST MATERIAL DESCRIPTIONS

| TMIN | ID | Physical Properties | Frequency |
|---|---|---|---|
| 0052-15C | AO + Mist (*Nitrosomonas eutropha* preparation) | Clear, transparent liquid | Twice per day (morning and evening) |
| 0053-15C | Placebo | Clear, transparent liquid | Twice per day (morning and evening) |

TABLE 10

SUPPORTING MATERIAL DESCRIPTIONS

| TMIN | ID | Physical Properties | Frequency |
|---|---|---|---|
| 0099-15C | Cleanser (Lot 293162) | Pale yellow, transparent liquid | Once per day |
| 0100-15C | Shampoo (Lot 293178) | Pale yellow, transparent liquid | Once per day |

Subject Disposition and Demographics

A summary of subject disposition information is included in Table 11. The demographic information for the per-protocol (PP) population is presented in Table 12. For applicable parameters, the number of subjects in each category is listed with the percentage of total subjects in parentheses.

TABLE 11

SUBJECT DISPOSITION

| | All Subjects n | AO + Mist n | Placebo n |
|---|---|---|---|
| Enrolled Subjects | 98 | 49 | 49 |
| Completed Subjects (PP Population) | 83 | 42 | 41 |
| Discontinued Subjects | 15 | 7 | 8 |
| Reason for Discontinuation | | | |
| Subject Requested withdrawal | 7 | 5 | 2 |
| Non-compliance | 3 | 0 | 3 |
| Lost to follow-up | 5 | 2 | 3 |

TABLE 12

SUMMARY OF DEMOGRAPHIC INFORMATION - PP POPULATION

| | All Subjects | AO + Mist | Placebo |
|---|---|---|---|
| N | 83 | 42 | 41 |
| Age (Years) | | | |
| Mean | 19.8 | 18.9 | 20.8 |
| Standard Deviation | 8.5 | 7.6 | 9.3 |
| Minimum | 12 | 12 | 12 |
| Median | 17.0 | 16.0 | 17.0 |
| Maximum | 44 | 40 | 44 |
| | n (%) | n (%) | n (%) |
| Sex | | | |
| Female | 50 (60.2) | 23 (54.8) | 27 (65.9) |
| Male | 33 (39.8) | 19 (45.2) | 14 (34.1) |
| Ethnicity/Race | | | |
| Asian | 8 (9.6) | 4 (9.5) | 4 (9.8) |
| Black or African American | 9 (10.8) | 5 (11.9) | 4 (9.8) |
| Hispanic or Latino | 6 (7.2) | 2 (4.8) | 4 (9.8) |
| White | 50 (60.2) | 24 (57.1) | 26 (63.4) |
| Multi-Racial | 10 (12.0) | 7 (16.7) | 3 (7.3) |
| Skin Type | | | |
| Combination | 49 (59.0) | 22 (52.4) | 27 (65.9) |
| Normal | 15 (18.1) | 7 (16.7) | 8 (19.5) |
| Oily | 19 (22.9) | 13 (31.0) | 6 (14.6) |
| Fitzpatrick Skin Type | | | |
| I | 2 (2.4) | 2 (4.8) | 0 (0.0) |
| II | 6 (7.2) | 5 (11.9) | 1 (2.4) |
| III | 49 (59.0) | 21 (50.0) | 28 (68.3) |
| IV | 19 (22.9) | 10 (23.8) | 9 (22.0) |
| V | 7 (8.4) | 4 (9.5) | 3 (7.3) |
| Acne Type | | | |
| Adolescent Acne | 55 (66.3) | 30 (71.4) | 25 (61.0) |
| Adult Acne | 28 (33.7) | 12 (28.6) | 16 (39.0) |
| Age Group (Years) | | | |
| 12-15 | 33 (39.8) | 16 (38.1) | 17 (41.5) |
| 16-18 | 22 (26.5) | 14 (33.3) | 8 (19.5) |
| 19-28 | 12 (14.5) | 5 (11.9) | 7 (17.1) |
| >28 | 16 (19.3) | 7 (16.7) | 9 (22.0) |

Procedures and Methods

Prior to the start of the study, potential subjects were screened over the telephone through the use of an IRB-approved script for eligibility criteria. Male and female adolescents and adults, between the ages of 12 and 45 years, with self-perceived normal, oily, and combination skin types were scheduled for eligibility screening at the clinic. Prospective subjects were instructed to remove all makeup at least 3 hours prior to each scheduled visit.

At visit 1 (baseline), prospective subjects 18 years of age or older or the parent/legal guardian of any minor subject under the age of 18 years, read and signed an informed consent form after the nature of the study was explained and any study-related questions were answered. Prospective minor subjects read and signed an assent form. Prospective subjects that signed this initial paperwork were assigned a screening number and evaluated for the following eligibility criteria:

Fitzpatrick Skin Classification: Types I-V qualified

The Fitzpatrick Skin Classification is based on the skin's unprotected response to the first 30 to 45 minutes of sun exposure after a winter season without sun exposure. The categories of skin types are as follows in Table 13:

TABLE 13

| Type | Physical Characteristics | Skin Reaction to UV |
|---|---|---|
| I | White; very fair; red or blonde hair; blue eyes; freckles | Always burns easily; never tans |
| II | White; fair; red or blonde hair; blue, hazel, or green eyes | Always burns easily; tans minimally |
| III | Cream white; fair with any eye or hair color; very common | Burns moderately; tans gradually |
| IV | Brown; typical Mediterranean white skin | Burns minimally; always tans well |
| V | Dark Brown; mid-eastern skin types, black hair, olive skin | Rarely burns; tans profusely |

TABLE 13-continued

| Type | Physical Characteristics | Skin Reaction to UV |
|---|---|---|
| VI | Black; black hair, black eyes, black skin | Never burns; deeply pigmented |

Clinically determined mild to moderately acne combined acne severity scale (minimum of 5-50 inflammatory lesions and 5-100 inflammatory lesions to qualify.

At least 1 target PIH/PIE lesion on the face

Prospective subjects completed an eligibility and health questionnaire. Screened subjects who passed eligibility requirements were enrolled into the study and assigned a subject number. Subjects participated in the following procedures:

Clinical Grading of Cosmetic Efficacy Parameters

Subjects were clinically graded by an expert blinded clinical grader for the following cosmetic efficacy parameters globally on the face using a modified Griffiths' 10-point scale[3] according to the following numerical definitions (with half-point scores assigned as necessary to accurately describe the skin condition):

0=none (best possible condition)

1 to 3=mild 4 to 6=moderate 7 to 9=severe (worst possible condition)

The following parameters (Table 14) were graded according to the listed scale anchors:

TABLE 14

| Parameter | 0 = | 9 = |
|---|---|---|
| Oily appearance (shine and feel) | No shine, flat/matte appearance | Strong shiny/oily appearance |
| Pore appearance | Small, tight, barely perceptible pores | Large, noticeable pores |
| Radiance | Radiant, luminous appearance | Dull/matte and or/sallow appearance |
| Blotchiness | No blotchiness/clear | Blotchy skin appearance |
| Skin tone (color) evenness | Even, healthy skin color | Uneven, discolored appearance |
| Visual smoothness | Smooth, even looking skin texture | Rough, uneven looking skin texture |
| Tactile smoothness | Smooth, even feeling skin texture | Rough, uneven feeling skin texture |

PIH/PIE Lesion Grading

An expert blinded clinical grader selected post-inflammatory hyperpigmentation/post-inflammatory erythema (PIH/PIE) lesions on the face of each subject and graded the lesions for darkness and size using the following grading scales:

Darkness

1 Slightly lighter than tone/color of surrounding skin

2 Equal to tone/color of surrounding skin (no visible PIH/PIE)

3 Slightly darker/redder than tone/color of surrounding skin

4 Moderately darker/redder than tone/color of surrounding skin

5 Markedly darker/redder than tone/color of surrounding skin

6 Extremely darker/redder than tone/color of surrounding skin

Size

0 Not visible 1 0.5 mm or less in diameter

2 Greater than 0.5 mm to 1.5 mm in diameter

3 Greater than 1.5 mm to 2.5 mm in diameter

4 Greater than 2.5 mm in diameter

Acne Counts

An expert blinded clinical grader counted and recorded the number of inflammatory acne lesions (papules, pustules, and cysts/nodules) and non-inflammatory acne lesions (open comedones and closed comedones) on each subject's forehead, left cheek, chin, and right cheek, separately (excluding lesions on the nose, under the jawline or along the hairline, including eye brows).

Tolerability Evaluations

Local cutaneous tolerability was evaluated by assessing the signs and symptoms of objective and subjective irritation globally on each subject's face (cosmetic treatment area). The following irritation parameters were evaluated:

Objective Irritation (clinically graded): erythema, edema, and scaling

Subjective Irritation (assessed by subjects): stinging, burning, and itching

Results of the irritation evaluations were recorded using the following scales (with half-point scores assigned as necessary to better describe the clinical condition):

| Erythema | |
|---|---|
| 0 = None | No erythema of the cosmetic treatment area |
| 1 = Mild | Slight, but definite redness of the cosmetic treatment area |
| 2 = Moderate | Definite redness of the cosmetic treatment area |
| 3 = Severe | Marked redness of the cosmetic treatment area |
| Edema | |
| 0 = None | No edema/swelling of the cosmetic treatment area |
| 1 = Mild | Slight, but definite edema of the cosmetic treatment area |
| 2 = Moderate | Definite edema of the cosmetic treatment area |
| 3 = Severe | Marked edema of the cosmetic treatment area |
| Scaling | |
| 0 = None | No scaling of the cosmetic treatment area |
| 1 = Mild | Barely perceptible, fine scales in limited areas of the cosmetic treatment area |
| 2 = Moderate | Fine scaling generalized to all areas of the cosmetic treatment area |
| 3 = Severe | Scaling and peeling of skin over all areas of the cosmetic treatment area |
| Stinging | |
| 0 = None | No stinging of the cosmetic treatment area |
| 1 = Mild | Slight stinging sensation of the cosmetic treatment area; not really bothersome |
| 2 = Moderate | Definite stinging of the cosmetic treatment area that is somewhat bothersome |
| 3 = Severe | Marked stinging sensation of the cosmetic treatment area that causes definite discomfort and may interrupt daily activities and/or sleep |
| Burning | |
| 0 = None | No burning of the cosmetic treatment area |
| 1 = Mild | Slight burning sensation of the cosmetic treatment area; not really bothersome |
| 2 = Moderate | Definite warm, burning of the cosmetic treatment area that is somewhat bothersome |
| 3 = Severe | Hot burning sensation of the cosmetic treatment area that causes definite discomfort and may interrupt daily activities and/or sleep |

| Itching | |
|---|---|
| 0 = None | No itching of the cosmetic treatment area |
| 1 = Mild | Slight itching sensation of the cosmetic treatment area; not really bothersome |
| 2 = Moderate | Definite itching of the cosmetic treatment area that is somewhat bothersome |
| 3 = Severe | Marked itching sensation of the cosmetic treatment area that causes definite discomfort and may interrupt daily activities and/or sleep |

Subjects acclimated to ambient temperature and humidity conditions for at least 15 minutes prior to participating in bioinstrumentation/imaging/microbiome sampling procedures. During the course of the study, applicable waiting/instrumentation rooms were maintained at a temperature of 68° F. to 75° F. and the relative humidity ranged from 35% to 65%.

After acclimation, subjects participated in the following procedures:

Sebumeter Measurements

Triplicate Sebumeter SM 815 (Courage+Khazaka, Germany) measurements were taken on the forehead to measure sebum quantity on the skin using a photometric method, independent of moisture. The measurement is the transmission of light through sebutape, a synthetic material that becomes transparent upon contact with sebum. A microprocessor in the Sebumeter calculates the amount (μg sebum/cm$^2$) on the skin surface based on the transparency of the sebutape.

Imaging Procedures

Prior to photography procedures, clinic personnel ensured subjects had a clean face with no makeup and subjects removed any jewelry from the area(s) to be photographed. Subjects were provided with a black or gray matte headband to keep hair away from the face and a black matte shirt or a black or gray matte cloth was draped over subjects' clothing. Subjects were instructed to adopt neutral, nonsmiling expressions with their eyes gently closed, and were carefully positioned for each photograph.

Full-face images were taken of each subject (center, right side, and left side views) using the VISTA CR photo-station (Canfield Imaging Systems, Fairfield, N.J.) with a Canon Mark II 5D digital SLR camera (Canon Incorporated, Tokyo, Japan) under standard lighting 1 (visible), standard lighting 2 (visible/bright), cross-polarized, parallel polarized, and UV-NF lighting conditions.

Microbiome Procedures

Microbiome samples were collected on the back of the neck, behind the right ear, and right cheek (1 from each location) of each subject. The swab was removed from its sterile wrapping, held from the stem away from the swab, rubbed vigorously about 20 times and rotated over a 3 inch area of the site being sampled. The swab was then placed into a tube (labeled with the time point) and the stem was clipped to ensure that the tube could close. The skin swabs were collected and frozen at −80° C. for subsequent DNA extraction and microbiome profiling. Subjects were instructed on how to take weekly standardized self-photographs ("selfies") using their smart phones and to complete questionnaires.

Subjects were distributed units of the supporting materials, and instructed to apply Shampoo (Lot 293178) once per day to the hair and scalp and use Cleanser (Lot 293162) once per day on the face for the duration of the study. Subjects were distributed a pre-weighed unit of the test material, AO+Mist (*Nitrosomonas eutropha* preparation), or Placebo according to a predetermined randomization.

Subjects were given the following verbal and written usage instructions:

Usage Instructions

Apply the test material (at least 6 pumps each time) to the hair, scalp, and face twice per day (each morning and evening) after cleansing and before bed and never directly before showering. Do not apply any makeup (foundation, eye shadow, et.) for 1 hour after product application and use the minimal amount.

Subjects were provided with written usage instructions, study instructions, a calendar of study visits, and a daily diary to record product application times.

Subjects returned to the clinic for visit 2 (week 4) and participated in the following procedures:

Clinic personnel recorded concomitant medications and questioned subjects regarding changes in their health. Adverse events were recorded if applicable.

Daily diaries were collected, reviewed for compliance, and retained by the clinic. New diaries were distributed.

Test material units were collected, visually inspected, weighed for compliance, and retained by the clinic. Supporting materials were visually inspected for compliance and returned to subjects.

Subjects participated in the following procedures as described for baseline:
Clinical grading of cosmetic efficacy parameters
PIH/PIE lesion grading
Acne counts
Tolerability evaluations Subjects participated in the following procedure:
Investigator's global improvement assessment (IGA) was performed using the following scale and numerical definitions:
1=Worse
2=No Improvement
3=Mildly Improved
4=Moderately Improved
5=Markedly Improved Subjects acclimated for at least 15 minutes and then participated in the following procedures as described for baseline:
Sebumeter measurements
Imaging procedures
Microbiome sampling After completion of the week 4 assessments, subjects participated in a 1-week regression period where test material use was discontinued (supporting materials were still used). Subjects returned to the clinic for visit 3 (week 5) and participated in the following procedures:

Clinic personnel recorded concomitant medications and questioned subjects regarding changes in their health. Adverse events were recorded if applicable.

Daily diaries were collected, reviewed for compliance, and retained by the clinic.

Supporting material units were collected, visually inspected for compliance, and retained by the clinic.

Subjects participated in the following procedures as described for baseline and week 4:
Clinical grading of cosmetic efficacy parameters
PIH/PIE lesion grading
Acne counts
Investigator's global improvement assessment
Tolerability evaluations Subjects acclimated for at least 15 minutes and then participated in the following procedures as described for baseline:
  Sebumeter measurements
  Imaging procedures
  Microbiome sampling After completion of week 5 study procedures, the following procedure was performed by a blinded clinical grader:
  Acne Grading Clinical grading of acne was performed using a modified Griffiths' 10-point scale[3] (where 0=no acne and 9=severe acne) on VISIA images taken in the clinic at baseline, week 4, and week 5 and from subjects' self-photographs taken at baseline and weeks 1, 2, 3, 4, and 5 to screen for any exacerbation of subject's underlying acne.

In addition, the VISIA images were clinically graded for acne using the FDA IGA scale[1] (0-4):

| | |
|---|---|
| 0 = Clear | No inflammatory or non-inflammatory lesions |
| 1 = Almost clear | Rare non-inflammatory lesions with no more than one small inflammatory lesion |
| 2 = Mild | Greater than Grade 1, some non-inflammatory lesions with no more than a few inflammatory lesion (papules/pustules only, no nodular lesions) |
| 3 = Moderate | Greater than Grade 2, up to many non-inflammatory lesions and may have some inflammatory lesions, but no more than one small nodular lesion |
| 4 = Severe | Greater than Grade 3, up to many non-inflammatory and inflammatory lesions, but no more than a few nodular lesions |

Biostatistics and Data Management

The per-protocol (PP) population was the primary population for all statistical analyses testing. The PP population included all subjects who were deemed eligible for study participation and completed the study according to protocol. Only the data of completing subjects were analyzed. Subjects may have been removed from the analysis in the case of an AE, an SAE, non-compliance, or Investigator discretion.

Triplicate Sebumeter measurements for each subject and time point were averaged prior to statistical analysis.

The digital images taken using cross-polarized lighting conditions were analyzed for pores using Macroversion "Pore_20121207" developed by Stephens & Associates using Image Pro Plus v7 software (MediaCybernetics, Inc., Rockville, Md.). An irregularly shaped area of interest was selected on the cheek area for the analysis. Pore analysis reported values for the number of pores (count), total area covered by pores, and the average depth of pores.

Acne count data was analyzed as follows for each grading location and for the total of the 4 graded areas (forehead, right cheek, left cheek, and chin):
  Papules, pustules, cysts/nodules, open comedones and closed comedones separately.
  Inflammatory acne lesions (combining papules, pustules and cysts/nodules) and noninflammatory acne lesions (combining open comedones and closed comedones) separately
  Global lesions (total of all 5 types of acne)

For the cosmetic efficacy grading data, acne grading data, PIH/PIE lesion grading data, acne counts, tolerability evaluation data, Sebumeter measurements, and pore image analysis parameters, a descriptive statistical summary is provided, including the number of observations (N), mean, median, standard deviation (SD), minimum (MIN) and maximum (MAX) at all visits.

Mean of the change from baseline (defined as the post-baseline value minus the baseline value) was estimated at each applicable postbaseline time point. The null hypothesis that the mean change from baseline is zero was estimated at week 4 and tested using a Wilcoxon signed-rank test for cosmetic efficacy grading parameters, acne grading, acne counts, image analysis for number of pores (count), and tolerability evaluations, and a paired t-test for Sebumeter measurements and image analysis for pores (total area covered by pores, and average depth of pores). For the regression phase, a similar analysis was performed for the change from week 4 at the week 5 time point, including testing the Investigator's global improvement assessment using a Wilcoxon signed-rank test.

Percent mean change from baseline/week 4 and percentage of subjects showing improvement or worsening was calculated using the following formulas:

Percent mean change from baseline=(visit mean score−baseline mean score)×100 baseline mean score Percent of subjects improved/worsened=(number of subjects improved/worsened from baseline)×100 total number of subjects Comparisons between the treatment cells were made at week 4 in terms of changes from baseline. The null hypothesis, that the mean change from baseline is equal between the 2 treatment cells, was tested for all parameters (except Investigator's global improvement assessment) at each applicable post-baseline time point using a Wilcoxon rank-sum test for cosmetic efficacy grading parameters, acne grading, acne counts, image analysis for number of pores (count), and tolerability evaluations, and a two sample t-test for Sebumeter measurements and image analysis for pores (total area covered and average depth of pores).

For the regression phase, a similar analysis was performed at week 5 in terms of changes from week 4 including testing the Investigator's global improvement assessment using a Wilcoxon rank-sum test.

Overall statistical results, as well as statistical results stratified by age (12-15, 16-18, 19-28, 29 and above), sex (male/female), adult acne (age 19 and above) and adolescent acne (age less than 19), and Fitzpatrick skin type (III, IV, and V [no analysis was run on I and II due to the small sample size]) are presented for clinical grading of cosmetic efficacy parameters, PIH/PIE lesion grading, acne grading, acne counts, Investigator's global improvement assessment, Sebumeter measurements, and image analysis of pore size. In addition demographic tabulation by treatment is presented for age, sex, adult and adolescent acne, and Fitzpatrick skin type.

For acne grading, Spearman's rank correlation coefficients for scores using the 2 scales (Griffiths' scale[3] and FDA scale[1]) were calculated for each applicable time point and treatment.

A statistical test was provided for the null hypothesis that the correlation coefficient is equal to 0. No treatment comparison was made. Similar correlation coefficients were calculated for the modified Griffiths' scores from VISIA and selfie images.

The SkinDex data, a subject-reported outcome that assesses Quality-of-Life, was provided from, which contained the responses to the 16 questions from each subject at baseline and weeks 2, 4, and 5. A frequency table, including count and percentage, is provided for the SkinDex data. A similar analysis is provided as for the clinical grading data, including analysis of data according to age, sex, adult and adolescent acne, and Fitzpatrick type.

Information on Skindex may be found through:
http://www.researchgate.net/publication/51646907_Using_the_Skindex-16_and_Common_Terminology_Criteria_for_Adverse_Events_to_assess_rash_symptoms_results_of_a_pooled-analysis_(N0993)

The survey was provided, containing the responses to 37 questions answered by subjects at weeks 1, 2, 3, 4, and 5.

For questions 1 through 19, responses ranged from 0 (worsened) to 6 (improved). For the remainder of the questions, response ranged from −1 (no/no change) to 1 (yes/positive change).

A frequency table, including count and percentage of subjects that selected each response option, is provided for the survey data. In addition, a binomial (sign) test was performed to test if the proportion of the combined designated favorable/positive responses is equal to the combined designated unfavorable/negative responses for each question at each time point. Treatment comparison was performed using a Fisher's exact test. For the questions #1 to #19, the test null hypothesis is that the proportion of favorable/unfavorable/neutral responses is equal between treatments. For the rest of the questions, the test null hypothesis is that the proportion of positive/negative responses is equal between treatments. Analysis of data was also performed according to age, sex, adult and adolescent acne, and Fitzpatrick type.

All statistical tests were 2-sided at significance level alpha=0.05. P-values are reported to 3 decimal places (0.000). No multiple testing corrections were considered in the study. Statistical analyses were performed using SAS software version 9.30 series (SAS Statistical Institute). Clinical grading and bioinstrumentation measurements were recorded using Stephens electronic data capture (EDC) system. The Stephens EDC is a computerized system designed for the collection of clinical data in electronic format. The 3 major aspects of EDC consist of a graphical user interface for data entry, a validation component to check for user data, and a reporting tool for analysis of the collected data.

Results
Clinical Grading of Acne from Images

For subjects that used AO+Mist (*Nitrosomonas eutropha* preparation), there was a statistically significant decrease (improvement) in acne grading scores on VISIA images using the FDA scale[1] at weeks 4 and 5 and using the Griffiths' scale[3] at week 5 when compared with baseline scores. Comparisons between the test materials based on the change from baseline for acne grading scores indicated a statistically significant difference VISIA image acne grading using the FDA scale[1] at week 4, in favor of AO+Mist (*Nitrosomonas eutropha* preparation).

Analysis of correlation coefficient from image grading results indicated a statistically significant positive correlation between acne grading scores on VISIA images at baseline, week 4 and week 5 (correlation coefficients ranging from 0.495-0.847), suggesting that self-photos may be a viable approach for documentation of progress during clinical trials.

Acne Counts
All Subjects

Subjects that used AO+Mist (*Nitrosomonas eutropha* preparation) had a statistically significant decrease (improvement) in counts for the total of the 4 graded areas (forehead, left cheek, chin, and right cheek) for papules and inflammatory acne at weeks 4 and 5 and for global lesions at week 4 when compared with baseline counts. Subjects that used Placebo had a statistically significant decrease (improvement) in counts for the total of the 4 graded areas for open comedones, closed comedones, non-inflammatory acne, and global lesions at weeks 4 and 5 and for papules and inflammatory acne at week 4 when compared with baseline counts. Comparisons between the test materials based on the change from baseline for acne counts for the total of the 4 graded areas indicated a statistically significant difference for closed comedones at week 4, in favor of Placebo.

Adult Acne Subjects

Subjects that used AO+Mist (*Nitrosomonas eutropha* preparation) had a statistically significant decrease (improvement) in acne counts for the total of the 4 graded areas (forehead, left cheek, chin, and right cheek) for papules, inflammatory acne, and global lesions at weeks 4 and 5 when compared with baseline counts. Subjects that used Placebo had a statistically significant decrease (improvement) in acne counts for the total of the 4 graded areas for closed comedones, non-inflammatory acne, and global lesions at weeks 4 and 5 and for open comedones at week 5 when compared with baseline counts. Comparisons between the test materials based on the change from baseline for acne counts for total of the 4 areas indicated a statistically significant difference for papules at week 4 in favor of AO+Mist (*Nitrosomonas eutropha* preparation) and for non-inflammatory acne at week 5 in favor of Placebo.

PIH/PIE Lesion Grading
All Subjects

Subjects that used AO+Mist (*Nitrosomonas eutropha* preparation) or Placebo had a statistically significant decrease (improvement) in PIH/PIE lesion grading scores for darkness and size of lesion 1 and lesion 2 at weeks 4 and 5 when compared with baseline scores. Comparisons between the test materials based on the change from baseline for PIH/PIE lesion grading scores indicated a statistically significant difference for size of lesion 1 at week 4, in favor of Placebo.

Adult Acne Subjects

Subjects that used AO+Mist (*Nitrosomonas eutropha* preparation) or Placebo had a statistically significant decrease (improvement) in PIH/PIE lesion grading scores for darkness of lesion 1 at weeks 4 and 5 and size of lesion 1 at week 5, and in the size of lesion 1 at week 4 for Placebo when compared with baseline scores. Comparisons between the test materials based on the change from baseline for PIH/PIE grading scores indicated no statistically significant differences.

SkinDex16

Results from the SkinDex16 data for subjects who used AO+Mist (*Nitrosomonas eutropha* preparation) indicated a statistically significant decrease (improvement) in response scores for the following inquiries and time points when compared with baseline scores:

Worry about your skin condition—week 2
The appearance of your skin condition—weeks 2, 4, and 5
Frustration about your skin condition—weeks 2 and 4
Embarrassment about your skin condition—weeks 2 and 5
Being annoyed about your skin condition—weeks 2 and 4

Figures 2A, 2B:
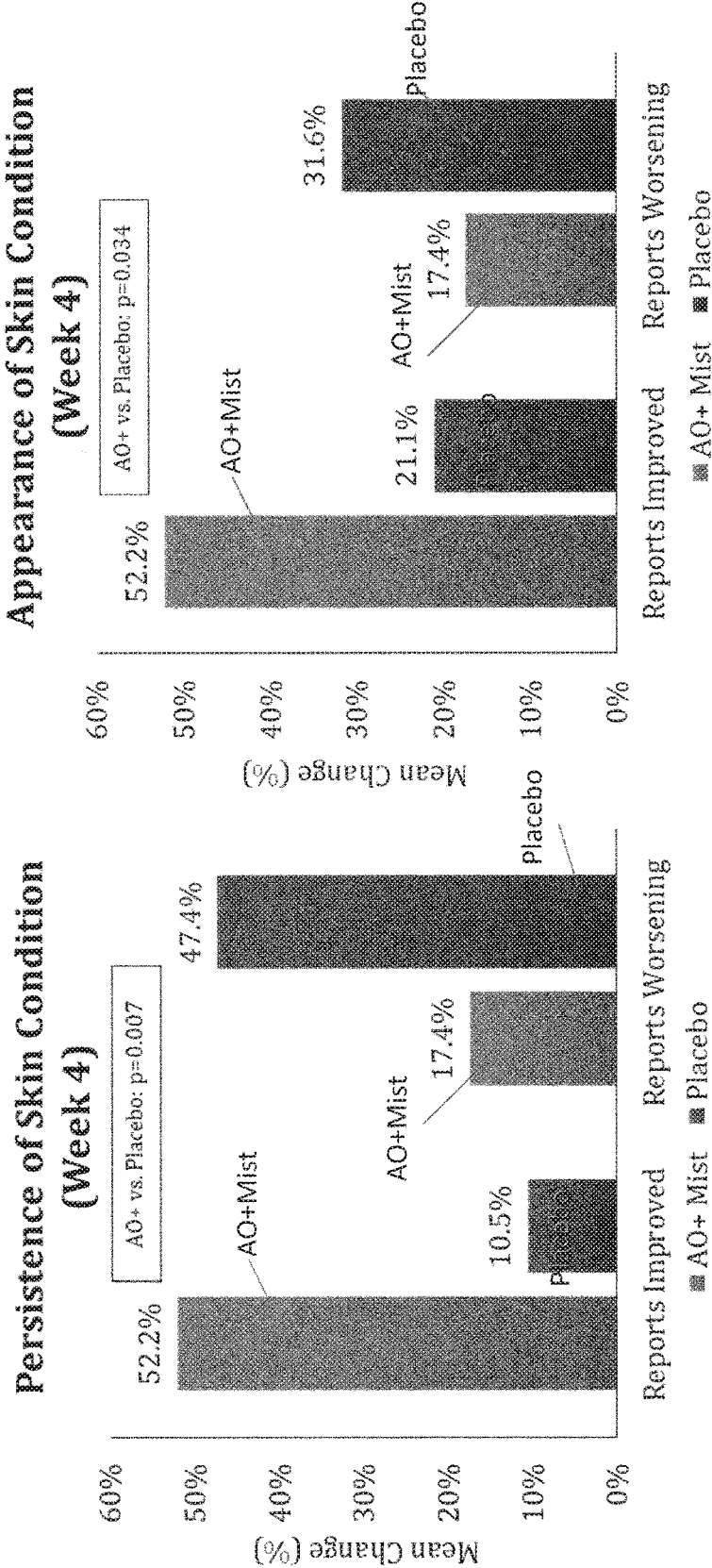
FIG. 2A shows the improvement of persistence of skin condition using ammonia oxidizing bacteria (AO+Mist) at Week 4. Mean change (%) is plotted versus report of improvement and report of worsening in AO+Mist and Placebo.
FIG. 2B shows the improvement of appearance of skin condition using ammonia oxidizing bacteria (AO+Mist) at Week 4. Mean change (%) is plotted versus report of improvement and report of worsening in AO+Mist and Placebo.
Figures 3A, 3B:
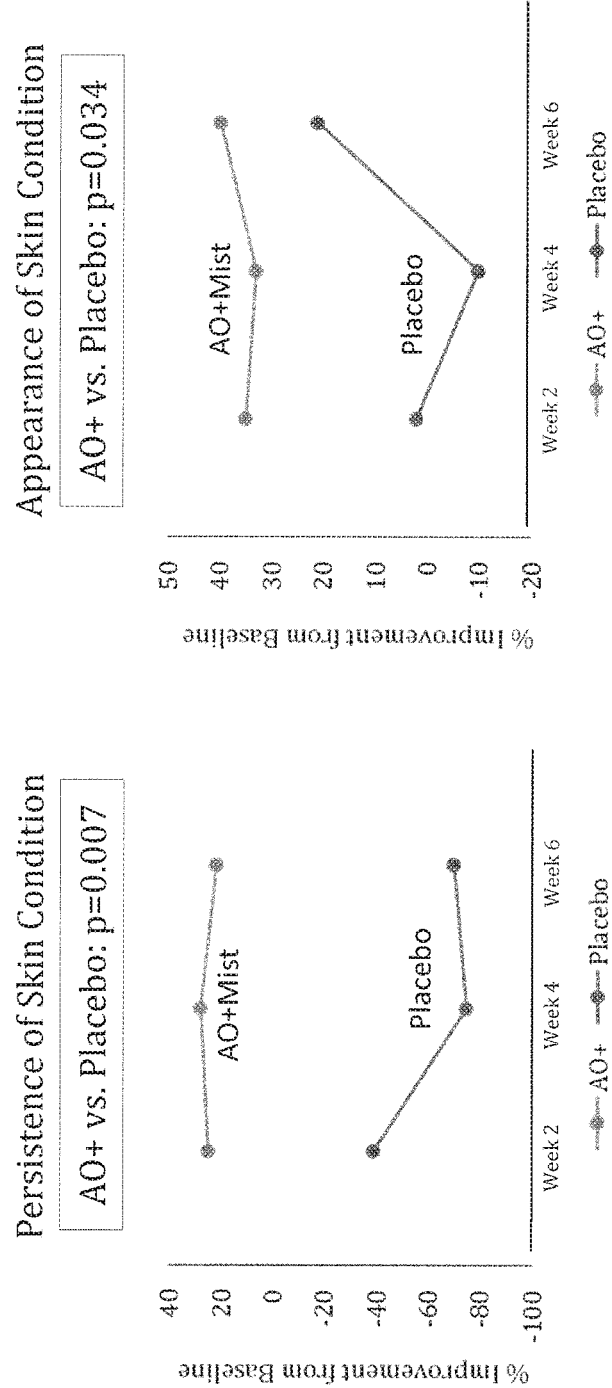
FIG. 3A shows the improvement of persistence of skin condition using ammonia oxidizing bacteria (AO+Mist) at Weeks 2, 4, and 6. Percent Improvement from Baseline (%) is plotted versus Week for AO+Mist and Placebo.
FIG. 3B shows the improvement in appearance of skin condition using ammonia oxidizing bacteria (AO+Mist) at Weeks 2, 4, and 6. Percent Improvement from Baseline (%) is plotted versus Week for AO+Mist and Placebo.

Results for subjects who used Placebo indicated a statistically significant increase (worsening) in response scores for the inquiry "the persistence/reoccurrence of your skin condition" at week 4 when compared with baseline scores. This is shown in FIG. 2A. The AO+Mist bars depicted on the graph are the first (from the left) and third (from the left). The Placebo bars depicted on the graph are the second (from the left) and fourth (from the left). FIG. 3A, also shows improvement in persistence in skin condition at week 2, week 4, and week 6 using AO+Mist. The line depicting the AO+Mist data resides above the line depicting Placebo data.

Comparisons between the test materials based on the change from baseline for SkinDex response scores indicated a statistically significant difference for the following inquiries at the indicated time points, in favor of AO+Mist (*Nitrosomonas eutropha* preparation):

Your skin condition hurting—week 2

The persistence/reoccurrence of your skin condition—week 4

Worry about your skin condition—week 5

The appearance of your skin condition—weeks 2, 4, and 5

Tolerability Evaluations

All Subjects and Adult Acne

Use of AO+Mist (*Nitrosomonas eutropha* preparation) or Placebo did not produce any statistically significant increase (worsening) in tolerability evaluation scores for erythema, scaling, edema, burning, stinging, and itching at weeks 4 and 5 when compared with baseline scores or during the regression phase when week 5 was compared with week 4.

Comparisons between the test materials based on the change from baseline for tolerability evaluation scores indicated no statistically significant differences at weeks 4 and 5.

Clinical Grading of Cosmetic Efficacy Parameters

All Subjects

Subjects that used the test material, AO+Mist (*Nitrosomonas eutropha* preparation), for 4 weeks had a statistically significant decrease (improvement) in clinical grading scores for blotchiness at week 5 (regression), and visual and tactile smoothness at weeks 4 and 5 (regression) when compared with baseline scores.

Subjects that used Placebo had a statistically significant decrease (improvement) in clinical grading scores for oily appearance (shine and feel) at week 4 when compared with baseline scores. Comparisons between the test materials based on the change from baseline for clinical grading scores indicated a statistically significant difference for blotchiness at week 5, in favor of AO+Mist (*Nitrosomonas eutropha* preparation).

Adult Acne Subjects

Subjects that used AO+Mist (*Nitrosomonas eutropha* preparation) had a statistically significant decrease (improvement) in clinical grading scores for blotchiness at week 5 and tactile smoothness at week 4 when compared with baseline scores. Comparisons between the test materials based on the change from baseline for clinical grading scores indicated a statistically significant difference for blotchiness and skin tone (color) evenness at week 5, in favor of AO+Mist (*Nitrosomonas eutropha* preparation).

Sebumeter Measurements

All Subjects and Adult Acne

Tables 15, 16, and 17 are related to the Sebumeter measurements and show that AOB application reduced sebum levels on the face of acne patients. Excess sebum is thought to contribute to acne.

TABLE 15

C15-CD035 Descriptive Statistics for Sebumeter Measurements

| Parameter | Treatment | Time Point | N (Total Available) | Mean | Standard Deviation | Minimum | Median | Maximum |
|---|---|---|---|---|---|---|---|---|
| Sebumeter measurements | AO + Mist | Baseline | 18 | 151.69 | 39.76 | 109.33 | 153.52 | 222.33 |
| | | Week 4 | 18 | 117.17 | 54.98 | 56.67 | 99.17 | 217.67 |
| | | Week 5 | 18 | 128.94 | 63.61 | 45.67 | 108.17 | 240.33 |
| | Placebo | Baseline | 18 | 154.50 | 47.68 | 100.67 | 142.67 | 249.33 |
| | | Week 4 | 18 | 148.89 | 62.53 | 42.00 | 143.33 | 248.33 |
| | | Week 5 | 18 | 120.56 | 67.96 | 38.67 | 112.00 | 299.00 |

TABLE 16

C15-CD035 Change from Baseline Statistics for Sebumeter Measurements

| Parameter | Treatment | Time Point | N (Total Available) | Subject Improved, % | Subject Worsened, % | Mean Change | Standard Deviation for Change | Mean Change, % | Paired T-test P-value [a] |
|---|---|---|---|---|---|---|---|---|---|
| Sebumeter measurements | AO + Mist | Week 4 | 18 | 77.8 | 22.2 | −34.52 | 39.96 | −22.8 | 0.002 |
| | | Week 5 | 18 | 61.1 | 38.9 | −22.74 | 46.27 | −15.0 | 0.052 |
| | Placebo | Week 4 | 18 | 50.0 | 50.0 | −5.61 | 46.91 | −3.6 | 0.619 |
| | | Week 5 | 18 | 77.8 | 22.2 | −33.94 | 54.56 | −22.0 | 0.017 |

[a] Calculated from Paired t-test
The testing hypothesis is that the mean change from baseline is equal to zero.

TABLE 17

C15-CD035 Comparisons Between Treatments for Sebumeter Measurements

| Parameter | Time Point | Comparison | Estimated Difference (SE) | Pairwise P-value[a] |
|---|---|---|---|---|
| Sebumeter measurements | Week 4 | AO + Mist vs Placebo | −28.91 (14.52) | 0.055 |
| | Week 5 | AO + Mist vs Placebo | 11.20 (16.86) | 0.511 |

[a] Calculated from Two sample t-test.
Testing hypothesis is that the mean change from baseline is equal between treatments.

Image Analysis of Pore Parameters

There were no statistically significant changes in image analysis data for number of pores, total area covered by pores, and average depth of pores at week 4 when compared with baseline values for either test material.

Comparisons between the test materials based on the change from baseline for image analysis data indicated a statistically significant difference for average depth of pores at week 4, in favor of Placebo.

Discussion and Conclusions

Overall results from this multi-site, double-blind, randomized, 4-week, placebo-controlled cosmetic trial indicate that use of the test material, AO+Mist (*Nitrosomonas eutropha* preparation), demonstrated safety and efficacy for the treatment of mild to moderate acne. The severity of disease, subjects' reported quality of life, and the number of inflammatory lesion counts all showed improvement in the AO+ treated group with a course of 4-week treatment. AO+ treatment appeared to have particularly beneficial effects in adult acne condition.

The study used the standard FDA Investigator's Global Acne (IGA) scale[1] to assess acne conditions using VISIA images under completely blinded condition. Results from acne grading of VISIA images indicate that subjects who used the AO+Mist (*Nitrosomonas eutropha* preparation) had a statistically significant decrease (improvement) in IGA scores using the FDA scale[1] at weeks 4 and 5 and in scores using the Griffiths' scale[3] at week 5 when compared with baseline scores. Comparisons between the test materials based on the change from baseline indicated a statistically significant difference for acne grading using the FDA scale[1] at week 4, in favor of AO+Mist (*Nitrosomonas eutropha* preparation). (See FIG. 1.)

Results of the acne counts showed that use of AO+Mist (*Nitrosomonas eutropha* preparation) resulted in a statistically significant decrease (improvement) in papules and inflammatory lesion counts at weeks 4 and 5, and global lesion counts at week 4, when compared with baseline counts. Although no statistically significant difference was observed between AO+Mist (*Nitrosomonas eutropha* preparation) and placebo, the data indicated a better and more sustained reduction in acne count in adult subjects who used AO+Mist (*Nitrosomonas eutropha* preparation).

The test product of the study, AO+Mist containing live *Nitrosomonas eutropha*, converts ammonia in sweat to acidified nitrite and nitric oxide locally. This mechanism is expected to potentially alleviate the main causes of acne by reducing local inflammation and reducing proliferation of pathogenic bacteria. The reduction in papules and inflammatory lesions and VISIA grading of IGA in a relatively short 4-week period are consistent with the expected mechanism of AO+Mist. FIG. 1 shows the improved IGA results at Week 4, through use of AO+Mist as compared to Placebo. The AO+Mist bars depicted on the graph are the first (from the left) and third (from the left). The Placebo bars depicted on the graph are the second (from the left) and fourth (from the left).

In preclinical studies higher concentrations of *Nitrosomonas eutropha* show enhanced antimicrobial effects against the acne-causing organism *Propionibacterium* acne, and accelerated skin healing. Subject-reported outcomes were measured using the Skindex16 Quality-of-Life survey. AO+Mist was associated with changes (improvements) in the group of questions that captured the subjects' emotional assessment of their disease. Specifically, statistically significant improvements were observed, in favor of AO+Mist (*Nitrosomonas eutropha* preparation), for skin condition hurting (week 2), persistence/reoccurrence of skin condition (week 4) (see FIG. 2A), worry about skin condition (week 5), and appearance of skin condition (weeks 2, 4, and 5). The appearance in skin condition improved significantly, as can be seen in FIG. 2B. The AO+Mist bars depicted on the graph are the first (from the left) and third (from the left). The Placebo bars depicted on the graph are the second (from the left) and fourth (from the left). FIG. 3B, also shows improvement in appearance of skin condition at week 2, week 4, and week 6 using AO+Mist. The line depicting the AO+Mist data resides above the line depicting Placebo data.

Results of clinical grading for use of AO+Mist (*Nitrosomonas eutropha* preparation) showed a statistically significant decrease (improvement) in clinical grading scores for visual and tactile smoothness at weeks 4 and 5 when compared with baseline scores and for blotchiness at week 5 when compared with baseline scores and to Placebo.

The use of the test material, AO+Mist (*Nitrosomonas eutropha* preparation), was very well tolerated by subjects with no statistically significant increase (worsening) in clinical grading scores for erythema, scaling, edema, burning, stinging, and itching at weeks 4 when compared with baseline scores.

The incidence of AEs was at about 2% and is consistent with the spontaneously reported incidence from approximately 3,000 users of AO+Mist. This safety tolerability profile would be attractive for many populations including women and adolescents.

This clinical trial is among one of the first to use self-photographs ("selfies") to capture facial acne conditions during the course of the trial. In order to determine if the self-photos are of sufficient quality for clinical assessment, the photos taken by subjects and the VISIA-CR images taken in the clinic were evaluated by a blinded trained grader. Analysis of correlation coefficient from grading results indicated a statistically significant positive correlation between acne grading scores from VISIA images (using the Griffiths' scale[3]) and from selfie images (using the Griffiths' scale[3]) at week 4 and week 5 (correlation coefficients ranging from 0.692-0.847), suggesting that self-photos by subjects may be a viable approach for documentation of progress during clinical trials.

REFERENCES

1. U.S. Food and Drug Administration. Guidance for industry: acne vulgaris: developing drugs for treatment. September 2005. http://www.fda.gov.
2. Shai, A., Maibach, H I, Baran, R. Baran. Acne in Handbook of Cosmetic skin Care. Publisher Martin Duntiz Ltd., Chapter 9, 81-100, 2001.
3. Griffiths C E, Wang T S, Hamilton T A, Voorhees J J, Ellis C N. A photonumeric scale for the assessment of cutaneous photodamage. *Arch Dermatol*. 1992; 128(3):347-351.

4. Rizer, R L, Mills, O H, Trookman, N S. The assessment of acne: a re-evaluation of grading strategies. Scientific Poster, Annual Meeting of the Am. Acad. Dermatol (2001).

Incorporation By Reference

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

Certain embodiments are within the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10017731B2). An electronic copy of the "Sequence Listing" will also be available from the USPTO upon request and payment of the fee set forth in 37 CFR 1.19(b)(3).

The invention claimed is:

1. A method of treating eczema in a subject, comprising: administering, as a spray, aerosol or mist, a preparation comprising live ammonia oxidizing bacteria, to the skin of the subject, in an amount effective to treat eczema.

2. The method of claim 1, wherein the spread or proliferation of a skin pathogen associated with eczema is limited or inhibited.

3. The method of claim 1, wherein administering the preparation reduces inflammation.

4. The method of claim 1, wherein administering provides for treatment or improvement of one or more of erythema, edema, scaling, stinging, burning, and itching.

5. The method of claim 1, wherein administering provides for treatment or improvement of one or more of oily appearance, pore appearance, radiance, blotchiness, skin tone evenness, visual smoothness, and tactile smoothness.

6. The method of claim 1, further comprising determining whether the subject is in need of treating eczema or reducing the severity or frequency of at least one symptom of eczema.

7. The method of claim 1, wherein the preparation of ammonia oxidizing bacteria comprises a suspension of the ammonia oxidizing bacteria in a buffer solution.

8. The method of claim 7, wherein the buffer solution is an aqueous buffer solution consisting essentially of disodium phosphate and magnesium chloride.

9. The method of claim 1, wherein the preparation is applied to any one or more of a face, neck, scalp, head, shoulder, arm, leg, underarm, torso, feet, knee, ankle, and buttocks of the subject.

10. The method of claim 1, wherein the preparation further comprises an excipient.

11. The method of claim 1, wherein the ammonia oxidizing bacteria is selected from the group consisting of *Nitrosomonas, Nitrosococcus, Nitrosospira, Nitrosocystis, Nitrosolobus, Nitrosovibrio*, and combinations thereof.

12. The method of claim 11, wherein the ammonia oxidizing bacteria is *Nitrosomonas eutropha* (*N. eutropha*).

13. The method of claim 12, wherein the ammonia oxidizing bacteria is *N. eutropha* D23, having ATCC accession number PTA-121157.

14. The method of claim 1, wherein an eczema treatment selected from the group of:
a corticosteroid, a topical or systemic immunosuppressant, a light therapy, and combinations thereof
is further administered to the subject.

15. The method of claim 1, wherein the preparation comprises viable ammonia oxidizing bacteria capable of converting ammonia or ammonium to nitrite at a rate of at least about 50 micromoles nitrite per minute.

\* \* \* \* \*